US012612468B2

(12) United States Patent
Garces et al.

(10) Patent No.: US 12,612,468 B2
(45) Date of Patent: Apr. 28, 2026

(54) ENGINEERING THE HINGE REGION TO DRIVE ANTIBODY DIMERIZATION

(71) Applicant: AMGEN INC., Thousand Oaks, CA (US)

(72) Inventors: Fernando Garces, Thousand Oaks, CA (US); Zhulun Wang, Thousand Oaks, CA (US)

(73) Assignee: AMGEN INC., Thousand Oaks, CA (US)

( * ) Notice: Subject to any disclaimer, the term of this patent is extended or adjusted under 35 U.S.C. 154(b) by 1049 days.

(21) Appl. No.: 17/615,555

(22) PCT Filed: May 29, 2020

(86) PCT No.: PCT/US2020/035196
§ 371 (c)(1),
(2) Date: Nov. 30, 2021

(87) PCT Pub. No.: WO2020/243477
PCT Pub. Date: Dec. 3, 2020

(65) Prior Publication Data
US 2022/0235148 A1     Jul. 28, 2022

Related U.S. Application Data

(60) Provisional application No. 62/854,907, filed on May 30, 2019.

(51) Int. Cl.
*C07K 16/46*        (2006.01)
*C07K 16/18*        (2006.01)
(52) U.S. Cl.
CPC ............ *C07K 16/468* (2013.01); *C07K 16/18* (2013.01); *C07K 2317/31* (2013.01); *C07K 2317/526* (2013.01); *C07K 2317/53* (2013.01); *C07K 2317/55* (2013.01); *C07K 2317/94* (2013.01)
(58) Field of Classification Search
None
See application file for complete search history.

(56) References Cited

U.S. PATENT DOCUMENTS

| RE30,985 | E | 6/1982 | Cartaya |
|---|---|---|---|
| 4,560,655 | A | 12/1985 | Baker |
| 4,657,866 | A | 4/1987 | Kumar |
| 4,767,704 | A | 8/1988 | Cleveland |
| 4,927,762 | A | 5/1990 | Darfler |
| 4,965,195 | A | 10/1990 | Namen |
| 4,968,607 | A | 11/1990 | Dower |
| 5,122,469 | A | 6/1992 | Mather |
| 5,545,806 | A | 8/1996 | Lonberg |
| 5,545,807 | A | 8/1996 | Surani |
| 5,569,825 | A | 10/1996 | Lonberg |
| 5,585,089 | A | 12/1996 | Queen |
| 5,625,126 | A | 4/1997 | Lonberg |
| 5,633,425 | A | 5/1997 | Lonberg |
| 5,661,016 | A | 8/1997 | Lonberg |
| 5,693,762 | A | 12/1997 | Queen |
| 5,731,168 | A | 3/1998 | Carter |
| 5,770,429 | A | 6/1998 | Lonberg |
| 5,789,650 | A | 8/1998 | Lonberg |
| 5,814,318 | A | 9/1998 | Lonberg |
| 5,874,299 | A | 2/1999 | Lonberg |
| 5,877,397 | A | 3/1999 | Lonberg |
| 5,939,598 | A | 8/1999 | Kucherlapati |
| 6,162,963 | A | 12/2000 | Kucherlapati |
| 6,165,476 | A | 12/2000 | Strom |
| 6,255,458 | B1 | 7/2001 | Lonberg |
| 6,300,129 | B1 | 10/2001 | Lonberg |
| 6,673,986 | B1 | 1/2004 | Kucherlapati |
| 6,713,610 | B1 | 3/2004 | Kucherlapati |

(Continued)

FOREIGN PATENT DOCUMENTS

| CN | 105849129 A | 8/2016 |
|---|---|---|
| EP | 0404097 B1 | 9/1996 |

(Continued)

OTHER PUBLICATIONS

Kabat et al. Sequences of proteins of immunological interest. 5th Edition a US Department of Health and Human Services, NIH publication No. 91-3242, pp. 670-699 (1991). (Year: 1991).*

Atwell et al., "Stable heterodimers from remodeling the domain interface of a homodimer using a phage display library," Journal of Molecular Biology, vol. 270(1): pp. 26-35 (1997).

Béranger et al., "Correspondence between the IMGT unique numbering for C-DOMAIN, the IMGT exon numbering, the Eu and Kabat numberings: Human IGHG," IMGT Scientific Chart (May 17, 2001, last updated Jun. 12, 2024).

Béranger et al., "Correspondence between the IMGT unique numbering for C-DOMAIN, the IMGT exon numbering, the Eu and Kabat numberings: Human IGHG," IMGT Scientific Chart obtained via Wayback Machine (May 17, 2021, last updated Jun. 8, 2016).

Bird et al., "Single-Chain Antigen-Binding Proteins," Science, vol. 242: pp. 423-426 (1988).

(Continued)

*Primary Examiner* — Anne M. Gussow
*Assistant Examiner* — Brianna K Swartwout
(74) *Attorney, Agent, or Firm* — Megan Thobe

(57) ABSTRACT

The clinical potential of multispecific antibodies like bispecific and trispecific antibodies shows great promise for targeting complex diseases. However, the generation of those molecules presents great challenges as in many cases it is desired to specifically drive the specific pairing of multiple polypeptide chains that are present in solutions. In the case of the heavy chains, there are two main regions that form a dimer interface. One of them is the CH3 region, which has been widely exploited by inserting either charge-pair mutations (CPMs) to steer the dimer interface or inserting large bulky residues into cavities (Knob in Hole) to physically favor and disfavor the dimer formation. However, each of these strategies may not be applied to every molecule and therefore there is the need for more tools. Here, we describe the engineering of the Hinge region with a small number of mutations that are capable to alone successfully drive the heavy chain dimerization.

15 Claims, 13 Drawing Sheets
Specification includes a Sequence Listing.

(56)                    References Cited

U.S. PATENT DOCUMENTS

| | | | |
|---|---|---|---|
| 7,183,076 B2 | 2/2007 | Arathoon | |
| 2003/0133939 A1 | 7/2003 | Ledbetter | |
| 2005/0037421 A1 | 2/2005 | Honda | |
| 2005/0136049 A1 | 6/2005 | Ledbetter | |
| 2008/0318207 A1 | 12/2008 | Aurora | |
| 2009/0048122 A1 | 2/2009 | Glaser | |
| 2014/0199294 A1* | 7/2014 | Mimoto | C07K 1/1075 |
| | | | 530/387.3 |

FOREIGN PATENT DOCUMENTS

| | | |
|---|---|---|
| EP | 0367566 B1 | 5/1997 |
| EP | 0546073 B1 | 9/1997 |
| EP | 0460846 B1 | 2/2002 |
| JP | 2012522493 A | 9/2012 |
| JP | 2016532690 A | 10/2016 |
| JP | 2017521361 A | 8/2017 |
| JP | 2017206512 A | 11/2017 |
| WO | 1987000195 A1 | 1/1987 |
| WO | 1990003430 A1 | 4/1990 |
| WO | 1990004036 A1 | 4/1990 |
| WO | 1991010741 A1 | 7/1991 |
| WO | 1991017271 A1 | 11/1991 |
| WO | 1992001047 A1 | 1/1992 |
| WO | 1992003918 A1 | 3/1992 |
| WO | 1992022646 A1 | 12/1992 |
| WO | 1993001227 A1 | 1/1993 |
| WO | 1993011161 A1 | 6/1993 |
| WO | 1994002602 A1 | 2/1994 |
| WO | 1996030498 A1 | 10/1996 |
| WO | 1996032478 A1 | 10/1996 |
| WO | 1996033735 A1 | 10/1996 |
| WO | 1997034631 A1 | 9/1997 |
| WO | 1998024893 A2 | 6/1998 |
| WO | 2000024782 A2 | 5/2000 |
| WO | 2006028936 A2 | 3/2006 |
| WO | 2008110348 A1 | 9/2008 |
| WO | 2008119353 A1 | 10/2008 |
| WO | 2009000099 A2 | 12/2008 |
| WO | 2011131746 A2 | 10/2011 |
| WO | 2011143545 A1 | 11/2011 |
| WO | 2011147986 A1 | 12/2011 |
| WO | 2013060867 A2 | 5/2013 |
| WO | 2014190441 A1 | 12/2014 |
| WO | 2017106383 A1 | 6/2017 |
| WO | 2018030806 A1 | 2/2018 |

OTHER PUBLICATIONS

Bruggermann, M. et al., "Designer Mice: The Production of Human Antibody Repertoires in Transgenic Animals," Year in Immunol., vol. 7, pp. 33-40 (1993).

Carter, "Bispecific human IgG by design," Journal of Immunological Methods, vol. 248(1-2): pp. 7-15 (2001).

Chen et al., "Immunoglobulin gene rearrangement in B-cell deficient mice generated by targeted deletion of the JH locus", International Immunology, vol. 5 (6), pp. 647-656 (1993).

Cosman et al., "Cloning, Sequence and Expression of Human Interleukin-2 Receptor", Nature, vol. 312 (5996), pp. 768-771 (1984).

Crick, "Is alpha-Keratin a Coiled Coil?" Nature, vol. 170, pp. 882-883 (1952).

Deboer et al., "The tac promoter: A functional hybrid derived from the trp and lac promoters," Proc. Natl. Acad. Sci. U.S.A., vol. 80, pp. 21-25 (1983).

European Patent Office, International Search Report in International Patent Application No. PCT/US2020/035196 (Nov. 27, 2020).

European Patent Office, Written Opinion of the International Searching Authority in International Patent Application No. PCT/US2020/035196 (Nov. 27, 2020).

Ewert et al., "Biophysical properties of camelid V(HH) domains compared to those of human V(H)3 domains", Biochemistry vol. 41 (11), pp. 3628-3636 (2002).

Ghetie et al., "Multiple Roles for the Major Histocompatibility Complex Class I-Related Receptor FcRn," Annu. Rev. Immunol., vol. 18: pp. 739-766 (2000).

Graham et al., "Characteristics of a Human Cell Line Transformed by DNA from Human Adenovirus Type 5", J. Gen. Virol., vol. 36 (1), pp. 59-72 (1977).

Gramer et al., "Production of stable bispecific IgG1 by controlled Fab-arm exchange: scalability from bench to large-scale manufacturing by application of standard approaches," mAbs, 5(6): 962-973 (2013).

Guss et al., "Structure of the IgG-binding regions of streptococcal protein G", The EMBO Journal, vol. 5 (7), pp. 1567-1575 (1986).

Hollinger et al., "Diabodies': small bivalent and bispecific antibody fragments," Proc. Natl. Acad. Sci. USA, vol. 90: pp. 6444-6448 (1993).

Kelsey et al., "Species- and tissue-specific expression of human alpha 1-antitrypsin in transgenic mice", Genes Dev., vol. 1 (2), pp. 161-171 (1987).

Kollias et al., "Regulated expression of human A gamma-, beta-, and hybrid gamma beta-globin genes in transgenic mice: manipulation of the developmental expression patterns", Cell, vol. 46 (1), pp. 89-94 (1986).

Kroesen et al., "Bispecific antibodies for treatment of cancer in experimental animal models and man," Advanced Drug Delivery Reviews, vol. 31, pp. 105-129 (1998).

Krumlauf et al., "Developmental regulation of alpha-fetoprotein genes in transgenic mice", Mol Cell Biol., vol. 5 (7), pp. 1639-1648 (1985).

Labrijn et al., "Controlled Fab-arm exchange for the generation of stable bispecific IgG1," Nature Protocols, vol. 9 (10), pp. 2450-2463 (2014).

Labrijn et al., "Efficient generation of stable bispecific IgG1 by controlled Fab-arm exchange," Proc. Natl. Acad. Sci. USA. 110:5145-50 (2013).

Leder et al., "Consequences of Widespread Deregulation of the c-myc Gene in Transgenic Mice: Multiple Neoplasms and Normal Development", Cell, vol. 45 (4), pp. 485-495 (1986).

Lonberg et al., "Human Antibodies from Transgenic Mice," Intern. Rev. Immunol., vol. 13, pp. 65-93 (1995).

Macdonald, "Expression of the pancreatic elastase I gene in transgenic mice", Hepatology, vol. 7 (Suppl 1), pp. 42S-51S (1987).

Mason et al., "The hypogonadal mouse: reproductive functions restored by gene therapy", Science, vol. 234 (4782), pp. 1372-1378 (1986).

Mather, "Establishment and characterization of two distinct mouse testicular epithelial cell lines", Biol. Reprod., vol. 23 (1), pp. 243-252 (1980).

Merchant et al., "An efficient route to human bispecific IgG," Nature Biotechnology, vol. 16: pp. 677-681 (1998).

Moore et al., "A robust heterodimeric Fc platform engineered for efficient development of bispecific antibodies of multiple formats," Methods, vol. 154: pp. 38-50 (2019).

Nolan et al., "Bifunctional antibodies: concept, production and applications," Biochimica et Biophysica Acta, vol. 1040(1): pp. 1-11 (1990).

Olafsen et al., "Characterization of engineered anti-p185HER-2 (scFv-CH3)2 antibody fragments (minibodies) for tumor targeting", Protein Engineering, Design & Selection, vol. 17 (4), pp. 315-323 (2004).

Pinkert et al., "An albumin enhancer located 10 kb upstream functions along with its promoter to direct efficient, liver-specific expression in transgenic mice", Genes Dev., vol. 1 (3), pp. 268-276 (1987).

Raghavan et al., "Fc Receptors and their Interactions with Immunoglobulins," Annu. Rev. Cell Dev. Biol., vol. 12: pp. 181-220 (1996).

Rathanaswami et al., "High-affinity binding measurements of antibodies to cell-surface-expressed antigens", Anal. Biochem., vol. 373 (1), pp. 52-60 (2008).

Ridgway et al., "'Knobs-into-holes' engineering of antibody CH3 domains for heavy chain heterodimerization," Protein Engineering, Design and Selection, vol. 9(7): pp. 617-621 (1996).

(56)             References Cited

OTHER PUBLICATIONS

Sambrook et al., "Analysis and Cloning of Eukaryotic Genomic DNA," Molecular Cloning: A Laboratory Manual, 2nd Ed., Ch. 9 pp. 9.2-9.62 (1989).
Sambrook et al., "Synthetic Oligonucleotide Probes," Molecular Cloning: A Laboratory Manual, 2nd Ed., Ch. 11 pp. 11.2-11.61 (1989).
Sambrook et al., Molecular Cloning: A Laboratory Manual, 2nd Ed., Cold Spring Harbor Laboratory Press, New York, Table of Contents (1989).
Sani et al., "The lipid network," Nature, vol. 314: pp. 283-286 (1985).
Saphire et al., "Crystal Structure of a Neutralizing Human IgG Against HIV-1: A Template for Vaccine Design," Science, vol. 293(5532): pp. 1155-1159 (2001).
Schaefer et al., "Immunoglobulin domain crossover as a generic approach for the production of bispecific IgG antibodies", Proc. Natl. Acad. Sci. USA, vol. 108 (27), pp. 11187-11192 (2011).
Sowdhamini et al., "Stereochemical modeling of disulfide bridges. Criteria for introduction into proteins by site-directed mutagenesis," Protein Engineering, Design and Selection, vol. 3(2): pp. 95-103 (1989).
Strop et al., "Generating bispecific human IgG1 and IgG2 antibodies from any antibody pair," J. Mol. Biol., vol. 420: pp. 204-219 (2012).
Tam et al., "Functional, Biophysical, and Structural Characterization of Human IgG1 and IgG4 Fc Variants with Ablated Immune Functionality," Antibodies, vol. 6(3): 12, pp. 1-34 (2017).
Thornsen et al., "Promoter-regulatory region of the major immediate early gene of human cytomegalovirus," Proc. Natl. Acad. U.S.A., vol. 81, pp. 659-663 (1984).
Umaña et al., "Engineered glycoforms of an antineuroblastoma IgG1 with optimized antibody-dependent cellular cytotoxic activity", Nat. Biotechnol., vol. 17 (2), pp. 176-180 (1999).
Ward et al., "Binding Activities of a Repertoire of Single Immunoglobulin Variable Domains Secreted from Escherichia coli," Nature, vol. 341: pp. 544-546 (1989).
Yamamoto et al., "Identification of a Functional Promoter in the Long Terminal Repeat of Rous Sarcoma Virus", Cell, vol. 22 (3), pp. 787-797 (1980).
Adams et al., "The c-myc Oncogene Driven by Immunoglobulin Enhancers Induces Lymphoid Malignancy in Transgenic Mice", Nature, vol. 318, pp. 533-538 (Dec. 1985).
Alexander et al., "Expression of the c-myc Oncogene Under Control of an Immunoglobulin Enhancer in Emu-myc Transgenic Mice", Molecular and Cellular Biology, vol. 7 (4), pp. 1436-1444 (Apr. 1987).
Ausubel et al., "Current Protocols in Molecular Biology", John Wiley & Sons Inc., vol. 1, 2 pages (1994).
Barnes et al., "Methods for Growth of Cultured Cells in Serum-Free Medium", Analytical Biochemistry, vol. 102, pp. 255-270 (1980).
Benoist et al., "In Vivo Sequence Requirements of the SV40 Early Promoter Region", Nature, vol. 290, pp. 304-310 (Mar. 26, 1981).
Brinkmann et al., "The making of bispecific antibodies," mAbs., vol. 9 (2): pp. 182-212 (2017).
Brinster et al., "Regulation of metallothionein—thymidine kinase fusion plasmids injected into mouse eggs", Nature, vol. 296 (5852), pp. 39-42 (1982).
Caton et al., "Influenza virus hemagglutinin-specific antibodies isolated from a combinatorial expression library are closely related to the immune response of the donor," Proc Natl Acad Sci U S A., vol. 87 (16), pp. 6450-6454 (1990).
Chothia et al., "Canonical structures for the hypervariable regions of immunoglobulins," J. Mol. Biol., vol. 196 (4), pp. 901-917 (1987).
Chothia et al., "Conformations of immunoglobulin hypervariable regions," Nature, vol. 342 (6252): pp. 877-883 (1989).
Choulier et al., "Covariance analysis of protein families: the case of the variable domains of antibodies," Proteins, vol. 41 (4), pp. 475-484 (2000).

Cortez-Retamozo et al., "Efficient Cancer Therapy with a Nanobody-Based Conjugate," Cancer Res., vol. 64 (8): pp. 2853-2857 (2004).
Demarest et al., "Optimization of the antibody C(H)3 domain by residue frequency analysis of IgG sequences", J. Mol. Biol., vol. 335 (1), pp. 41-48 (2004).
Desmyter et al., "Antigen specificity and high affinity binding provided by one single loop of a camel single-domain antibody," J Biol Chem., vol. 276 (28), pp. 26285-26290 (2001).
Fishwild et al., "High-Avidity Human IgG Kappa Monoclonal Antibodies from a Novel Strain of Minilocus Transgenic Mice", Nature Biotechnol., vol. 14 (7), pp. 845-851 (1996).
Fredericks et al., "Identification of Potent Human Anti-IL-1Ri Antagonist Antibodies", Protein Eng. Design Select., vol. 17 (1), pp. 95-106 (2004).
Grosschedl et al., "Introduction of a µ Immunoglobulin Gene into the Mouse Germ Line: Specific Expression in Lymphoid Cells and Synthesis of Functional Antibody", Cell, vol. 38 (3), pp. 647-658 (1984).
Ham et al., "Media and growth requirements", Methods in Enzymology, vol. 58, pp. 44-93 (1979).
Hammer et al., "Diversity of Alpha-Fetoprotein Gene Expression in Mice Is Generated by a Combination of Separate Enhancer Elements", Science, vol. 235 (4784), pp. 53-58 (1987).
Hanahan, "Heritable formation of pancreatic beta-cell tumours in transgenic mice expressing recombinant insulin/simian virus 40 oncogenes", Nature, vol. 315 (6015), pp. 115-122 (1985).
Harding et al., "Class Switching in Human Immunoglobulin Transgenic Mice", Ann. NY Acad. Sci., vol. 764, pp. 536-546 (1995).
Hugo et al., "VL position 34 is a key determinant for the engineering of stable antibodies with fast dissociation rates", Protein Engineering, Design and Selection, vol. 16 (5), pp. 381-386 (2003).
Huston et al., "Protein engineering of antibody binding sites: recovery of specific activity in an anti-digoxin single-chain Fv analogue produced in Escherichia coli," Proc. Natl. Acad. Sci. USA, vol. 85 (16): pp. 5879-5883 (1988).
Jakobovits et al., "Analysis of homozygous mutant chimeric mice: deletion of the immunoglobulin heavy-chain joining region blocks B-cell development and antibody production", Proc. Natl. Acad. Sci. USA, vol. 90 (6), pp. 2551-2555 (1993).
Jakobovits et al., "Germ-line transmission and expression of a human-derived yeast artificial chromosome", Nature, vol. 362 (6417), pp. 255-258 (1993).
Jespers et al., "Guiding the Selection of Human Antibodies from Phage Display Repertoires to a Single Epitope of an Antigen", Bio/Technology, vol. 12 (9), pp. 899-903 (1994).
Jones et al., "Replacing the Complementarity-Determining Regions in a Human Antibody with those from a Mouse", Nature, vol. 321 (6069), pp. 522-525 (1986).
Lindmark et al., "Binding of Immunoglobulins to Protein A and Immunoglobulin Levels in Mammalian Sera", J Immunol Methods, vol. 62 (1), pp. 1-13 (1983).
Lonberg et al., "Antigen-specific human antibodies from mice comprising four distinct genetic modifications", Nature, vol. 368 (6474), pp. 856-859 (1994).
Lonberg, N., "Transgenic Approaches to Human Monoclonal Antibodies", The Pharmacology of Monoclonal Antibodies, Eds. M. Rosenberg et al., Ch. 3, pp. 49-101 (1994).
Magram et al., "Developmental regulation of a cloned adult beta-globin gene in transgenic mice", Nature, vol. 315 (6017), pp. 338-340 (1985).
Mather et al., "Culture of testicular cells in hormone-supplemented serum-free medium", Ann. NY Acad. Sci., vol. 383, pp. 44-68 (1982).
Mendez et al., "Functional transplant of megabase human immunoglobulin loci recapitulates human antibody response in mice", Nat. Genet., vol. 15 (2), pp. 146-156 (1997).
Ornitz et al., "Elastase I Promoter Directs Expression of Human Growth Hormone and SV40 T Antigen Genes to Pancreatic Acinar Cells in Transgenic Mice", Cold Spring Harb. Symp. Quant. Biol., vol. 50, pp. 399-409 (1985).
Powers et al., "Expression of single-chain Fv-Fc fusions in Pichia pastoris", J. Immunolog. Meth., vol. 251 (1-2), pp. 123-135 (2001).

(56)                    References Cited

OTHER PUBLICATIONS

Readhead et al., "Expression of a myelin basic protein gene in transgenic shiverer mice: correction of the dysmyelinating phenotype", Cell, vol. 48 (4), pp. 703-712 (1987).

Riechmann et al., "Reshaping human antibodies for therapy", Nature, vol. 332 (6162), pp. 323-327 (1988).

Rothman et al., "Antibody-dependent cytotoxicity mediated by natural killer cells is enhanced by castanospermine-induced alterations of IgG glycosylation", Mol Immunol., vol. 26 (12), pp. 1113-1123 (1989).

Shields et al., "Lack of fucose on human IgG1 N-linked oligosaccharide improves binding to human Fcgamma RIII and antibody-dependent cellular toxicity," J Biol Chem., vol. 277 (30), pp. 26733-40 (2002).

Shinkawa et al., "The absence of fucose but not the presence of galactose or bisecting N-acetylglucosamine of human IgG1 complex-type oligosaccharides shows the critical role of enhancing antibody-dependent cellular cytotoxicity," J Biol Chem., vol. 278(5): pp. 3466-3473 (2003).

Swift et al., "Tissue-Specific Expression of the Rat Pancreatic Elastase I Gene in Transgenic Mice", Cell, vol. 38 (3), pp. 639-646 (1984).

Taylor et al., "A transgenic mouse that expresses a diversity of human sequence heavy and light chain immunoglobulins", Nucleic Acids Res., vol. 20 (23), pp. 6287-6295 (1992).

Taylor et al., "Human immunoglobulin transgenes undergo rearrangement, somatic mutation and class switching in mice that lack endogenous IgM", Intl. Immunol., vol. 6 (4), pp. 579-591 (1994).

Tuaillon et al., "Biased Utilization of DHQ52 and JH4 Gene Segments in a Human Ig Transgenic Minilocus Is Independent of Antigenic Selection", J Immunol., vol. 152 (6), pp. 2912-2920 (1994).

Urlaub and Chasin, "Isolation of Chinese hamster cell mutants deficient in dihydrofolate reductase activity," Proc. Natl. Acad. Sci. USA, vol. 77 (7), pp. 4216-4220 (1980).

Verhoeyen et al., "Reshaping Human Antibodies: Grafting an Antilysozyme Activity", Science, vol. 239 (4847), pp. 1534-1536 (1988).

Villa-Komaroff et al., "A bacterial clone synthesizing proinsulin", Proc Natl Acad Sci U S A., vol. 75 (8), pp. 3727-3731 (1978).

Wagner et al., "Nucleotide sequence of the thymidine kinase gene of herpes simplex virus type 1," Proc Natl Acad Sci U S A., vol. 78 (3), pp. 1441-1445 (1981).

Yamane-Ohnuki et al., "Establishment of FUT8 Knockout Chinese Hamster Ovary Cells: An Ideal Host Cell Line for Producing Completely Defucosylated Antibodies With Enhanced Antibody-Dependent Cellular Cytotoxicity", Biotechnol Bioeng., vol. 87 (5), pp. 614-622 (2004).

Zapata et al., "Engineering linear F(ab')2 fragments for efficient production in Escherichia coli and enhanced antiproliferative activity", Protein Eng., vol. 8 (10), pp. 1057-1062 (1995).

Hui et al., "The solution structure of the human IgG2 subclass is distinct from those for human IgG1 and IgG4 providing an explanation for their discrete functions", Journal of Biological Chemistry, vol. 294(28), pp. 10789-10806 (2019).

* cited by examiner

TARGETING THE HINGE REGION TO FORM HETERODIMERS

Molecular Architecture
of a mIgG2 (1IGT)

FAB 1

FAB 2

FC

Cys 237
Cys' 237
Cys 240
Cys' 240
Cys 242
Cys' 242

SEQUENCE ALIGNMENT FOR IGG1, IGG2 AND IGG4

THE CHARGED ZIPPER HINGE– DESIGN CZH01

|  | 230 | 240 | 250 |
|---|---|---|---|
| IgG2 | KKIEPR–GPTIKPCPPCKCPAPNLLGGPS | | (SEQ ID NO. 72) |
| IgG1 | KKAEPKSCDKTHTCPPC—PAPELLGGPS | | (SEQ ID NO. 73) |
| IgG4 | KRVESKYGPP––CPPC—PAPEFLGGPS | | (SEQ ID NO. 74) |

Sequence numbering from 1HZH IgG1 crystal structure

ANALYTICAL CEX AND MASS SPEC – CZH01

THE CHARGED ZIPPER HINGE— DESIGN CZH09

IgG2  KKTEPR-GPTIKPCPPCKCPAPNLLGGPS (SEQ ID NO. 75)
IgG1  KKAEPKSCDKTHTCPPC—PAPELLGGPS (SEQ ID NO. 76)
IgG4  KRVESKYGPP—CPPC—PAPEFLGGPS (SEQ ID NO. 77)

Figure 11:
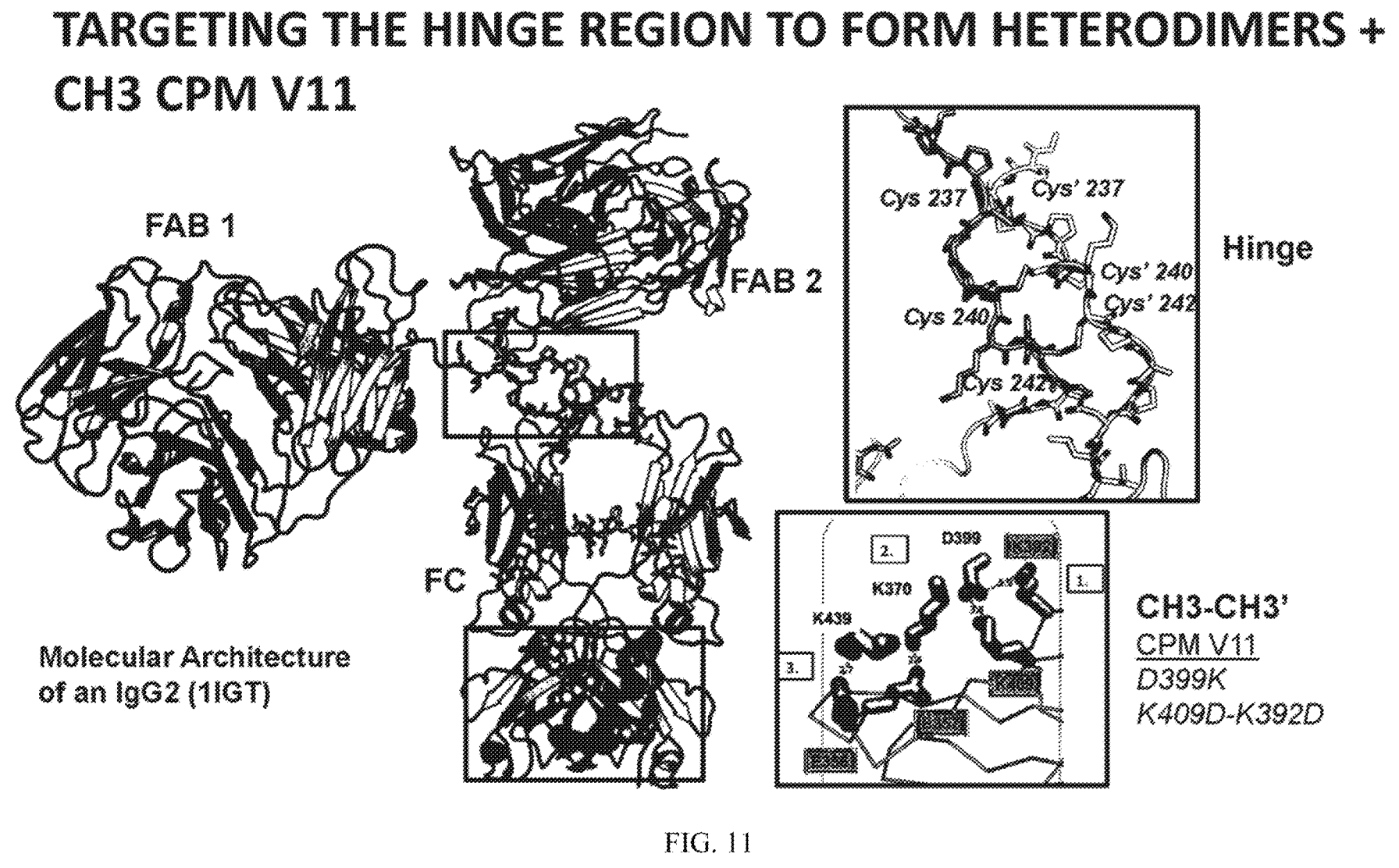

TARGETING THE HINGE REGION TO FORM HETERODIMERS + CH3 CPM V11

Hinge

Cys 237
Cys 237
Cys 240
Cys' 240
Cys' 242
Cys 242

FAB 1

FAB 2

FC

Molecular Architecture of an IgG2 (1IGT)

CH3-CH3'
CPM V11
D399K
K409D-K392D

SUMMARY TABLE : HINGE DESIGNS + CH3-CH3' CPM V11

FIG. 12

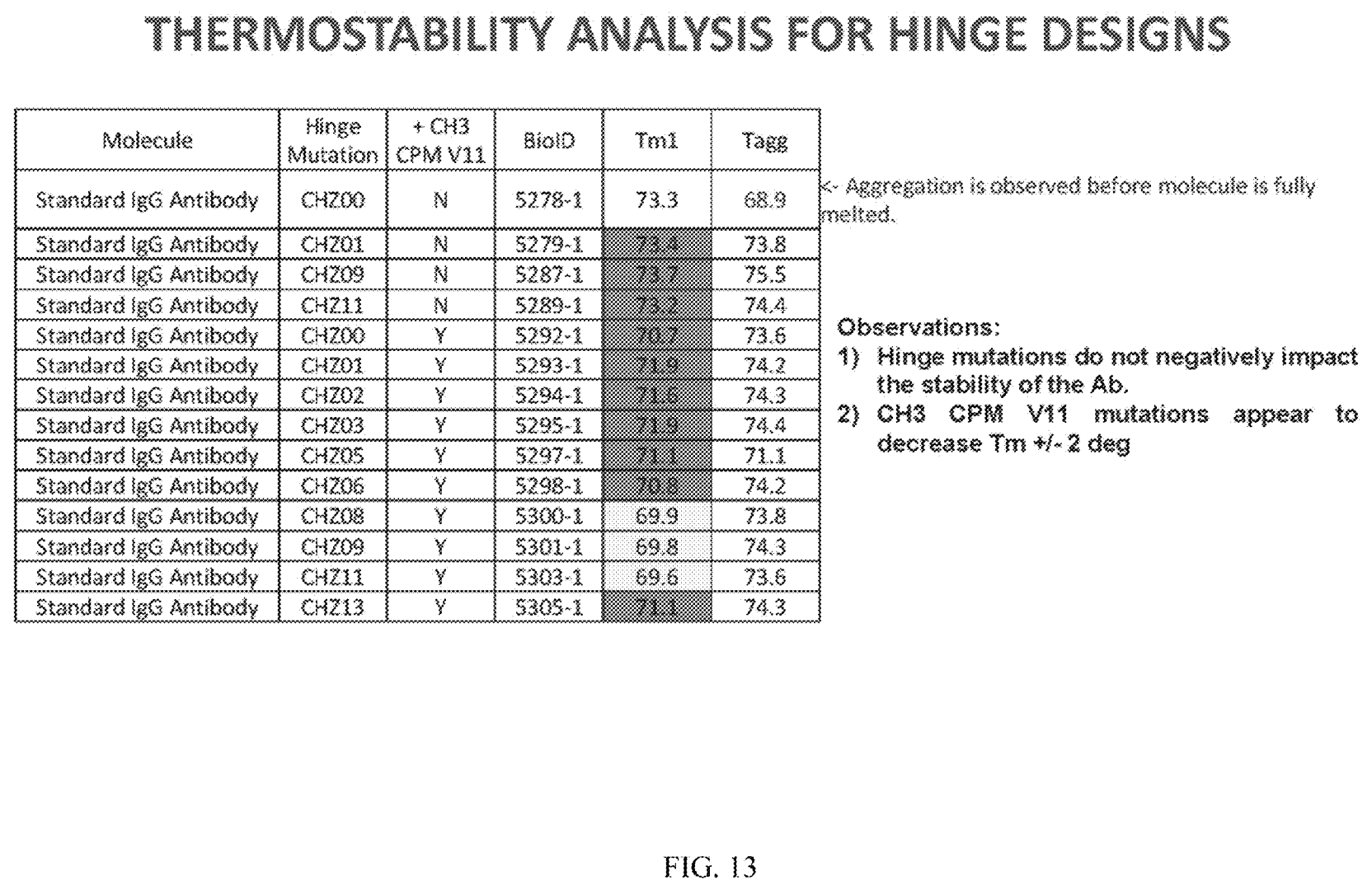

THERMOSTABILITY ANALYSIS FOR HINGE DESIGNS

| Molecule | Hinge Mutation | + CH3 CPM V11 | BioID | Tm1 | Tagg | |
|---|---|---|---|---|---|---|
| Standard IgG Antibody | CHZ00 | N | 5278-1 | 73.3 | 68.9 | <-- Aggregation is observed before molecule is fully melted. |
| Standard IgG Antibody | CHZ01 | N | 5279-1 |  | 73.8 | |
| Standard IgG Antibody | CHZ09 | N | 5287-1 |  | 75.5 | |
| Standard IgG Antibody | CHZ11 | N | 5289-1 |  | 74.4 | |
| Standard IgG Antibody | CHZ00 | Y | 5292-1 |  | 73.6 | |
| Standard IgG Antibody | CHZ01 | Y | 5293-1 |  | 74.2 | |
| Standard IgG Antibody | CHZ02 | Y | 5294-1 |  | 74.3 | |
| Standard IgG Antibody | CHZ03 | Y | 5295-1 |  | 74.4 | |
| Standard IgG Antibody | CHZ05 | Y | 5297-1 |  | 71.1 | |
| Standard IgG Antibody | CHZ06 | Y | 5298-1 |  | 74.2 | |
| Standard IgG Antibody | CHZ08 | Y | 5300-1 | 69.9 | 73.8 | |
| Standard IgG Antibody | CHZ09 | Y | 5301-1 | 69.8 | 74.3 | |
| Standard IgG Antibody | CHZ11 | Y | 5303-1 | 69.6 | 73.6 | |
| Standard IgG Antibody | CHZ13 | Y | 5305-1 |  | 74.3 | |

Observations:
1) Hinge mutations do not negatively impact the stability of the Ab.
2) CH3 CPM V11 mutations appear to decrease Tm +/- 2 deg

FIG. 13

ENGINEERING THE HINGE REGION TO DRIVE ANTIBODY DIMERIZATION

CROSS REFERENCE TO RELATED APPLICATIONS

This application is a national stage application under 35 U.S.C. § 371 of International Application No. PCT/US2020/035196, having an international filing date of May 29, 2020, which claims the benefit of U.S. Provisional Application No. 62/854,907, filed on May 30, 2019, each of which is incorporated by reference herein in its entirety.

SEQUENCE LISTING

This instant application contains a Sequence Listing which has been submitted electronically in ASCII format and is hereby incorporated by reference in its entirety. Said ASCII copy, created on Feb. 5, 2026, is named A-2388-US-PCT Replacement Sequence Listing ST25 and is 28,552 bytes in size.

FIELD OF THE INVENTION

The present invention relates to the field of biopharmaceuticals. In particular, the invention relates to multispecific antigen binding proteins that are capable of specifically binding to at least two target antigens. The multispecific antigen binding proteins comprise two distinct heavy chains in the hinge region that utilize charge pair mutations in order to both facilitate heterodimer formation while inhibiting homodimer formation.

BACKGROUND OF THE INVENTION

Antibodies have become the modality of choice within the biopharma industry because they possess several characteristics that are attractive to those developing therapeutic molecules. Along with the ability to target specific structures or cells, antibodies make its target susceptible to Fc-receptor cell-mediated phagocytosis and killing (Raghavan and Bjorkman 1996). Further, the antibody's ability to interact with neonatal Fc-receptor (FcRn) in a pH dependent manner confers it with extended serum half-life (Ghetie and Ward 2000). This unique feature of antibodies allows extending the half-life of therapeutic protein or peptide in the serum by engineering Fc-fusion molecules.

In certain instances, it is desirable to create a molecule that contains the Fc portion of an antibody but comprises a heterodimer. An important application of Fc heterodimeric molecules is the generation of multispecific antibodies, for example, a bispecific antibody. Bispecific antibodies refer to antibodies having specificities for at least two different antigens (Nolan and O'Kennedy 1990; de Leij, Molema et al. 1998; Carter 2001). Instead of having identical sequence in both the Fabs, bispecific antibodies bear different sequences in the two Fabs so that each arm of the Y-shaped molecule can bind to different antigens. Another application of Fc heterodimers is the addition of a half-life extension moiety to a therapeutic molecule. In such instances one or both of the two different Fc portions can be fuse to one or more therapeutic molecules in need of half-life extension.

The classical method of producing Fc heterodimers was developed by Carter and co-workers when they engineered heavy chains for heterodimerization using a "knobs-into-holes" strategy (Ridgway, Presta et al. 1996; Atwell, Ridgway et al. 1997; Merchant, Zhu et al. 1998; Carter 2001).

The knobs-into-holes concept was originally proposed by Crick as a model for packing of amino acid side chains between adjacent α-helices (Crick 1952). Carter and coworkers created a knob at the CH3 domain interface of the first chain by replacing a smaller amino acid side chain with a larger one (for example, T366Y); and a hole in the juxtaposed position at the CH3 interface of the second chain was created by replacing a larger amino acid side chain with a smaller one (for example, Y407T). The basis for creating knob and hole in the juxtaposed positions is that the knob and hole interaction will favor heterodimer formation, whereas the knob-knob and the hole-hole interaction will hinder homodimers formation due to the steric clash and deletion of favorable interactions, respectively. The knobs-into-holes mutations were also combined with inter-CH3 domain disulfide bond engineering to enhance heterodimer formation (Sowdhamini, Srinivasan et al. 1989; Atwell, Ridgway et al. 1997). In addition to these mutations, the input DNA ratio was also varied to maximize the yield (Merchant, Zhu et al. 1998). The "knobs-into-holes" technique is disclosed in U.S. Pat. Nos. 5,731,168 and 7,183,076.

The clinical potential of multi-specific antibodies (molecules that target multiple targets simultaneously) like bispecific and tri-specific antibodies and half-life extended therapeutic proteins shows great promise for targeting complex diseases. However, the generation of those molecules presents great challenges as in many cases we wish to specifically drive the pairing of multiple polypeptide chains that are present in solutions. Here, we describe the engineering of the hinge region with a small number of mutations that are capable to alone successfully drive Fc dimerization.

SUMMARY OF THE INVENTION

In one aspect the present invention is directed to an isolated heteromultimer comprising a heterodimeric immunoglobulin hinge domain comprising a first immunoglobulin hinge domain polypeptide and a second immunoglobulin hinge domain polypeptide, wherein:

(i) the first immunoglobulin hinge domain polypeptide comprises the following amino acid substitutions: P243K, A244K, P245K, N/E246K, and L247K; and (ii) the second immunoglobulin hinge domain polypeptide comprises the following amino acid substitutions: P243D, A244D, P245D, N/E246D, and L247D;

wherein the numbering of amino acid residues is according to the EU index as set forth in Kabat.

In another aspect, the present invention is directed to an isolated heteromultimer comprising a heterodimeric immunoglobulin hinge domain comprising a first immunoglobulin hinge domain polypeptide and a second immunoglobulin hinge domain polypeptide, wherein:

(i) the first immunoglobulin hinge domain polypeptide comprises the following amino acid substitution: A244H; and (ii) the second immunoglobulin hinge domain polypeptide comprises the following amino acid substitutions: N/E246D, and L247D;

wherein the numbering of amino acid residues is according to the EU index as set forth in Kabat.

In another aspect, the present invention is directed to an isolated heteromultimer comprising a heterodimeric immunoglobulin hinge domain comprising a first immunoglobulin hinge domain polypeptide and a second immunoglobulin hinge domain polypeptide, wherein:

(i) the first immunoglobulin hinge domain polypeptide comprises the following amino acid substitutions: H237K, T238K, A244K and N/E246K; and (ii) the second immunoglobulin hinge domain polypeptide comprises the following amino acid substitutions: H237D, T238D, A244D, and N/E246D;

wherein the numbering of amino acid residues is according to the EU index as set forth in Kabat.

In certain embodiments each hinge domain polypeptide of the heteromultimer further comprises an L248C substitution.

In certain embodiments, each immunoglobulin hinge domain polypeptide further comprises a CH3 domain. In one embodiment, one CH3 domain comprises a F405L, F405A, F405D, F405E, F405H, F405I, F405K, F405M, F405N, F405Q, F405S, F405T, F405V, F405W, or F405Y mutation; and the other CH3 domain comprises a K409R mutation; wherein the numbering of amino acid residues is according to the EU index as set forth in Kabat. In one embodiment, one CH3 domain comprises a T366W mutation; and the other CH3 domain comprises T366S, L368A, Y407V mutations; wherein the numbering of amino acid residues is according to the EU index as set forth in Kabat. In one embodiment, one CH3 domain comprises K/R409D and K392D mutations; and the other CH3 domain comprises D399K and E356K mutations; wherein the numbering of amino acid residues is according to the EU index as set forth in Kabat. In one embodiment, one CH3 domain comprises a Y349C mutation; and the other CH3 domain comprises either a E356C or a S354C mutation; wherein the numbering of amino acid residues is according to the EU index as set forth in Kabat. In one embodiment, one CH3 domain comprises Y349C and T366W mutations; and the other CH3 domain comprises E356C, T366S, L368A, and Y407V mutations; wherein the numbering of amino acid residues is according to the EU index as set forth in Kabat. In one embodiment, one CH3 domain comprises Y349C and T366W mutations; and the other CH3 domain comprises S354C, T366S, L368A, Y407V mutations; wherein the numbering of amino acid residues is according to the EU index as set forth in Kabat.

In certain embodiments, the immunoglobulin hinge region is an IgG1 hinge region. In certain embodiments, the heteromultimer is a bispecific or multispecific antibody.

BRIEF DESCRIPTION OF THE DRAWINGS

FIG. 3 depicts the sequence alignment for IgG1 (SEQ ID NO: 42), IgG2 (SEQ ID NO: 41), and IgG4 (SEQ ID NO: 43).

FIG. 4 depicts a summary table of hinge designs and quality control assessment (MSQC). The SEQ ID NOs. are for the HC and HC', respectively, and are SEQ ID NOs. 44 and 45 for CHZ00, SEQ ID NOs. 46 and 47 for CHZ01, SEQ ID NOs. 48 and 49 for CHZ02, SEQ ID NOs. 50 and 51 for CHZ03, SEQ ID NOs. 52 and 53 for CHZ04, SEQ ID NOs. 54 and 55 for CHZ05, SEQ ID NOs. 56 and 57 for CHZ06, SEQ ID NOs. 58 and 59 for CHZ07, SEQ ID NOs. 60 and 61 for CHZ08, SEQ ID NOs. 62 and 63 for CHZ09, SEQ ID NOs. 64 and 65 for CHZ10, SEQ ID NOs. 66 and 67 for CHZ11, SEQ ID NOs. 68 and 69 for CHZ12, and SEQ ID NOs. 70 and 71 for CHZ13.

FIG. 11 depicts targeting the hinge region to form heterodimers+CH3 CPM v11.

FIG. 12 depicts a summary table of hinge designs+CH3-CH3' CPM v11. The SEQ ID NOs. are for the HC and HC', respectively, and are SEQ ID NOs. 44 and 45 for CHZ00+ V11, SEQ ID NOs. 46 and 47 for CHZ01+V11, SEQ ID NOs. 48 and 49 for CHZ02+V11, SEQ ID NOs. 50 and 51 for CHZ03+V11, SEQ ID NOs. 52 and 53 for CHZ04+V11, SEQ ID NOs. 54 and 55 for CHZ05+V11, SEQ ID NOs. 56 and 57 for CHZ06+V11, SEQ ID NOs. 58 and 59 for CHZ07+V11, SEQ ID NOs. 60 and 61 for CHZ08+V11, SEQ ID NOs. 62 and 63 for CHZ09+V11, SEQ ID NOs. 64 and 65 for CHZ10+V11, SEQ ID NOs. 66 and 67 for CHZ11+V11, SEQ ID NOs. 68 and 69 for CHZ12+V11, and SEQ ID NOs. 70 and 71 for CHZ13+V11.

FIG. 13 depicts thermostability analysis for hinge designs. Hinge mutations do not negatively impact the stability of the Ab and CH3 CPM v11 mutations appear to decrease Tm +/-2 deg.

DETAILED DESCRIPTION OF THE INVENTION

Figure 1:
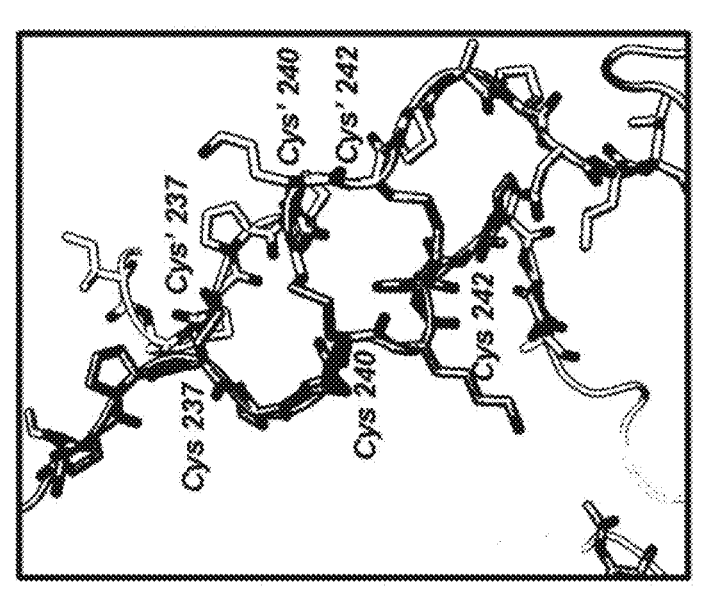
FIG. 1 depicts targeting the hinge region to form heterodimers.
Figure 1:
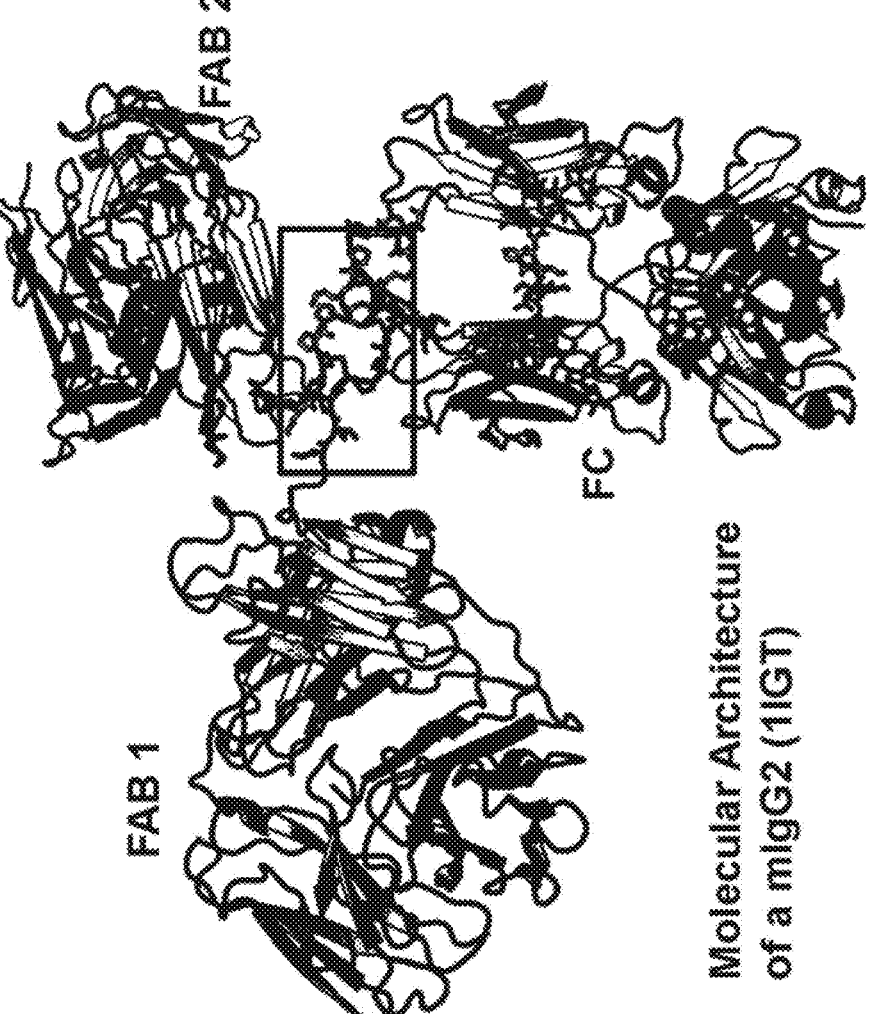

In one aspect the present invention is directed to an isolated heteromultimer comprising a heterodimeric immunoglobulin hinge domain comprising a first immunoglobulin hinge domain polypeptide and a second immunoglobulin hinge domain polypeptide, wherein:

(i) the first immunoglobulin hinge domain polypeptide comprises the following amino acid substitutions: P243K, A244K, P245K, N/E246K, and L247K; and (ii) the second immunoglobulin hinge domain polypeptide comprises the following amino acid substitutions: P243D, A244D, P245D, N/E246D, and L247D;

wherein the numbering of amino acid residues is according to the EU index as set forth in Kabat.

In another aspect, the present invention is directed to an isolated heteromultimer comprising a heterodimeric immunoglobulin hinge domain comprising a first immunoglobulin hinge domain polypeptide and a second immunoglobulin hinge domain polypeptide, wherein:

(i) the first immunoglobulin hinge domain polypeptide comprises the following amino acid substitution: A244H; and (ii) the second immunoglobulin hinge domain polypeptide comprises the following amino acid substitutions: N/E246D, and L247D;

wherein the numbering of amino acid residues is according to the EU index as set forth in Kabat.

In another aspect, the present invention is directed to an isolated heteromultimer comprising a heterodimeric immunoglobulin hinge domain comprising a first immunoglobulin hinge domain polypeptide and a second immunoglobulin hinge domain polypeptide, wherein:

(i) the first immunoglobulin hinge domain polypeptide comprises the following amino acid substitutions: H237K, T238K, A244K and N/E246K; and (ii) the second immunoglobulin hinge domain polypeptide comprises the following amino acid substitutions: H237D, T238D, A244D, and N/E246D;

wherein the numbering of amino acid residues is according to the EU index as set forth in Kabat.

In certain embodiments each hinge domain polypeptide of the heteromultimer further comprises an L248C substitution.

In certain embodiments, each immunoglobulin hinge domain polypeptide further comprises a CH3 domain. In one embodiment, one CH3 domain comprises a F405L, F405A, F405D, F405E, F405H, F405I, F405K, F405M, F405N, F405Q, F405S, F405T, F405V, F405W, or F405Y mutation; and the other CH3 domain comprises a K409R mutation; wherein the numbering of amino acid residues is according to the EU index as set forth in Kabat. In one embodiment, one CH3 domain comprises a T366W mutation; and the other CH3 domain comprises T366S, L368A, Y407V mutations; wherein the numbering of amino acid residues is according to the EU index as set forth in Kabat. In one embodiment, one CH3 domain comprises K/R409D and K370E mutations; and the other CH3 domain comprises D399K and E357K mutations; wherein the numbering of amino acid residues is according to the EU index as set forth in Kabat.

In particular embodiments, the heterodimeric antibody comprises a first heavy chain comprising negatively-charged amino acids at positions 392 and 409 (e.g., K392D and K409D substitutions), and a second heavy chain comprising positively-charged amino acids at positions 356 and 399 (e.g., E356K and D399K substitutions). In other particular embodiments, the heterodimeric antibody comprises a first heavy chain comprising negatively-charged amino acids at positions 392, 409, and 370 (e.g., K392D, K409D, and K370D substitutions), and a second heavy chain comprising positively-charged amino acids at positions 356, 399, and 357 (e.g., E356K, D399K, and E357K substitutions). In related embodiments, the first heavy chain is from an anti-CGRP receptor antibody and the second heavy chain is from an anti-PAC1 receptor antibody. In other related embodiments, the first heavy chain is from an anti-PAC1 receptor antibody and the second heavy chain is from an anti-CGRP receptor antibody.

In one embodiment, one CH3 domain comprises a Y349C mutation; and the other CH3 domain comprises either a E356C or a S354C mutation; wherein the numbering of amino acid residues is according to the EU index as set forth in Kabat. In one embodiment, one CH3 domain comprises Y349C and T366W mutations; and the other CH3 domain comprises E356C, T366S, L368A, and Y407V mutations;

wherein the numbering of amino acid residues is according to the EU index as set forth in Kabat. In one embodiment, one CH3 domain comprises Y349C and T366W mutations; and the other CH3 domain comprises S354C, T366S, L368A, Y407V mutations; wherein the numbering of amino acid residues is according to the EU index as set forth in Kabat.

In certain embodiments, the immunoglobulin hinge region is an IgG1 hinge region.

In certain embodiments, the heteromultimer is a bispecific or multispecific antibody.

As used herein, the term "antigen binding protein" refers to a protein that specifically binds to one or more target antigens. An antigen binding protein can include an antibody and functional fragments thereof. A "functional antibody fragment" is a portion of an antibody that lacks at least some of the amino acids present in a full-length heavy chain and/or light chain, but which is still capable of specifically binding to an antigen. A functional antibody fragment includes, but is not limited to, a Fab fragment, a Fab' fragment, a F(ab') 2 fragment, a Fv fragment, a Fd fragment, and a complementarity determining region (CDR) fragment, and can be derived from any mammalian source, such as human, mouse, rat, rabbit, or camelid. Functional antibody fragments may compete for binding of a target antigen with an intact antibody and the fragments may be produced by the modification of intact antibodies (e.g. enzymatic or chemical cleavage) or synthesized de novo using recombinant DNA technologies or peptide synthesis.

An antigen binding protein can also include a protein comprising one or more functional antibody fragments incorporated into a single polypeptide chain or into multiple polypeptide chains. For instance, antigen binding proteins can include, but are not limited to, a single chain Fv (scFv), a diabody (see, e.g., EP 404,097; WO 93/11161; and Hollinger et al., Proc. Natl. Acad. Sci. USA, Vol. 90:6444-6448, 1993); an intrabody; a domain antibody (single VL or VH domain or two or more VH domains joined by a peptide linker; see Ward et al., Nature, Vol. 341:544-546, 1989); a maxibody (2 scFvs fused to Fc region, see Fredericks et al., Protein Engineering, Design & Selection, Vol. 17:95-106, 2004 and Powers et al., Journal of Immunological Methods, Vol. 251:123-135, 2001); a triabody; a tetrabody; a minibody (scFv fused to CH3 domain; see Olafsen et al., Protein Eng Des Sel., Vol. 17:315-23, 2004); a peptibody (one or more peptides attached to an Fc region, see WO 00/24782); a linear antibody (a pair of tandem Fd segments (VH-CH1-VH-CH1) which, together with complementary light chain polypeptides, form a pair of antigen binding regions, see Zapata et al., Protein Eng., Vol. 8:1057-1062, 1995); a small modular immunopharmaceutical (see U.S. Patent Publication No. 20030133939); and immunoglobulin fusion proteins (e.g. IgG-scFv, IgG-Fab, 2scFv-IgG, 4scFv-IgG, VH-IgG, IgG-VH, and Fab-scFv-Fc).

"Multispecific" means that an antigen binding protein is capable of specifically binding to two or more different antigens. "Bispecific" means that an antigen binding protein is capable of specifically binding to two different antigens. As used herein, an antigen binding protein "specifically binds" to a target antigen when it has a significantly higher binding affinity for, and consequently is capable of distinguishing, that antigen, compared to its affinity for other unrelated proteins, under similar binding assay conditions. Antigen binding proteins that specifically bind an antigen may have an equilibrium dissociation constant $(K_D) \leq 1 \times 10^{-6}$ M. The antigen binding protein specifically binds antigen with "high affinity" when the $K_D$ is $\leq 1 \times 10^{-8}$ M.

Affinity is determined using a variety of techniques, an example of which is an affinity ELISA assay. In various embodiments, affinity is determined by a surface plasmon resonance assay (e.g., BIAcore®-based assay). Using this methodology, the association rate constant ($k_a$ in $M^{-1}s^{-1}$) and the dissociation rate constant ($k_a$ in $s^{-1}$) can be measured. The equilibrium dissociation constant ($K_D$ in M) can then be calculated from the ratio of the kinetic rate constants ($k_d/k_a$). In some embodiments, affinity is determined by a kinetic method, such as a Kinetic Exclusion Assay (KinExA) as described in Rathanaswami et al. Analytical Biochemistry, Vol. 373:52-60, 2008. Using a KinExA assay, the equilibrium dissociation constant ($K_D$ in M) and the association rate constant ($k_a$ in $M^{-1}s^{-1}$) can be measured. The dissociation rate constant ($k_a$ in $s^{-1}$) can be calculated from these values ($K_D$ X $k_a$). In other embodiments, affinity is determined by an equilibrium/solution method. In certain embodiments, affinity is determined by a FACS binding assay.

In some embodiments, the bispecific antigen binding proteins described herein exhibit desirable characteristics such as binding avidity as measured by $k_a$ (dissociation rate constant) of about $10^{-2}$, $10^{-3}$, $10^{-4}$, $10^{-5}$, $10^{-6}$, $10^{-7}$, $10^{-8}$, $10^{-9}$, $10^{-10}$ $s^{-1}$ or lower (lower values indicating higher binding avidity), and/or binding affinity as measured by $K_D$ (equilibrium dissociation constant) of about $10^{-9}$, $10^{-10}$, $10^{-11}$, $10^{-12}$, $10^{-13}$, $10^{-14}$, $10^{-15}$, $10^{-16}$ M or lower (lower values indicating higher binding affinity).

As used herein, the term "antigen binding domain," which is used interchangeably with "binding domain," refers to the region of the antigen binding protein that contains the amino acid residues that interact with the antigen and confer on the antigen binding protein its specificity and affinity for the antigen.

As used herein, the term "CDR" refers to the complementarity determining region (also termed "minimal recognition units" or "hypervariable region") within antibody variable sequences. There are three heavy chain variable region CDRs (CDRH1, CDRH2 and CDRH3) and three light chain variable region CDRs (CDRL1, CDRL2 and CDRL3). The term "CDR region" as used herein refers to a group of three CDRs that occur in a single variable region (i.e. the three-light chain CDRs or the three-heavy chain CDRs). The CDRs in each of the two chains typically are aligned by the framework regions to form a structure that binds specifically with a specific epitope or domain on the target protein. From N-terminus to C-terminus, naturally-occurring light and heavy chain variable regions both typically conform with the following order of these elements: FR1, CDR1, FR2, CDR2, FR3, CDR3 and FR4. A numbering system has been devised for assigning numbers to amino acids that occupy positions in each of these domains. This numbering system is defined in Kabat Sequences of Proteins of Immunological Interest (1987 and 1991, NIH, Bethesda, MD), or Chothia & Lesk, 1987, *J. Mol. Biol.* 196:901-917; Chothia et al., 1989, Nature 342:878-883. Complementarity determining regions (CDRs) and framework regions (FR) of a given antibody may be identified using this system.

In some embodiments of the bispecific antigen binding proteins of the invention, the binding domains comprise a Fab, a Fab', a F(ab')$_2$, a Fv, a single-chain variable fragment (scFv), or a NANOBODY®. In one embodiment, both binding domains are Fab fragments. In another embodiment, one binding domain is a Fab fragment and the other binding domain is a scFv.

Papain digestion of antibodies produces two identical antigen-binding fragments, called "Fab" fragments, each with a single antigen-binding site, and a residual "Fc" fragment which contains the immunoglobulin constant region. The Fab fragment contains all of the variable domain, as well as the constant domain of the light chain and the first constant domain (CH1) of the heavy chain. Thus, a "Fab fragment" is comprised of one immunoglobulin light chain (light chain variable region (VL) and constant region (CL)) and the CH1 region and variable region (VH) of one immunoglobulin heavy chain. The heavy chain of a Fab molecule cannot form a disulfide bond with another heavy chain molecule. The Fc fragment displays carbohydrates and is responsible for many antibody effector functions (such as binding complement and cell receptors), that distinguish one class of antibody from another. The "Fd fragment" comprises the VH and CH1 domains from an immunoglobulin heavy chain. The Fd fragment represents the heavy chain component of the Fab fragment.

A "Fab' fragment" is a Fab fragment having at the C-terminus of the CH1 domain one or more cysteine residues from the antibody hinge region.

A "F(ab')$_2$ fragment" is a bivalent fragment including two Fab' fragments linked by a disulfide bridge between the heavy chains at the hinge region.

The "Fv" fragment is the minimum fragment that contains a complete antigen recognition and binding site from an antibody. This fragment consists of a dimer of one immunoglobulin heavy chain variable region (VH) and one immunoglobulin light chain variable region (VL) in tight, non-covalent association. It is in this configuration that the three CDRs of each variable region interact to define an antigen binding site on the surface of the VH-VL dimer. A single light chain or heavy chain variable region (or half of an Fv fragment comprising only three CDRs specific for an antigen) has the ability to recognize and bind antigen, although at a lower affinity than the entire binding site comprising both VH and VL.

A "single-chain variable antibody fragment" or "scFv fragment" comprises the VH and VL regions of an antibody, wherein these regions are present in a single polypeptide chain, and optionally comprising a peptide linker between the VH and VL regions that enables the Fv to form the desired structure for antigen binding (see e.g., Bird et al., Science, Vol. 242:423-426, 1988; and Huston et al., Proc. Natl. Acad. Sci. USA, Vol. 85:5879-5883, 1988).

A "NANOBODY®." is the heavy chain variable region of a heavy-chain antibody. Such variable domains are the smallest fully functional antigen-binding fragment of such heavy-chain antibodies with a molecular mass of only 15 kDa. See Cortez-Retamozo et al., *Cancer Research* 64:2853-57, 2004. Functional heavy-chain antibodies devoid of light chains are naturally occurring in certain species of animals, such as nurse sharks, wobbegong sharks and Camelidae, such as camels, dromedaries, alpacas and llamas. The antigen-binding site is reduced to a single domain, the VHH domain, in these animals. These antibodies form antigen-binding regions using only heavy chain variable region, i.e., these functional antibodies are homodimers of heavy chains only having the structure H2L2 (referred to as "heavy-chain antibodies" or "HCAbs"). Camelized VHH reportedly recombines with IgG2 and IgG3 constant regions that contain hinge, CH2, and CH3 domains and lack a CH1 domain. Camelized VHH domains have been found to bind to antigen with high affinity (Desmyter et al., J. Biol. Chem., Vol. 276:26285-90, 2001) and possess high stability in solution (Ewert et al., Biochemistry, Vol. 41:3628-36, 2002). Methods for generating antibodies having camelized heavy chains are described in, for example, U.S. Patent Publication Nos.

2005/0136049 and 2005/0037421. Alternative scaffolds can be made from human variable-like domains that more closely match the shark V-NAR scaffold and may provide a framework for a long penetrating loop structure.

In particular, embodiments of the bispecific antigen binding proteins of the invention, the binding domains comprise an immunoglobulin heavy chain variable region (VH) and an immunoglobulin light chain variable region (VL) of an antibody or antibody fragment which specifically binds to the desired antigen.

The "variable region," used interchangeably herein with "variable domain" (variable region of a light chain (VL), variable region of a heavy chain (VH)) refers to the region in each of the light and heavy immunoglobulin chains which is involved directly in binding the antibody to the antigen. As discussed above, the regions of variable light and heavy chains have the same general structure and each region comprises four framework (FR) regions whose sequences are widely conserved, connected by three CDRs. The framework regions adopt a beta-sheet conformation and the CDRs may form loops connecting the beta-sheet structure. The CDRs in each chain are held in their three-dimensional structure by the framework regions and form, together with the CDRs from the other chain, the antigen binding site.

The binding domains that specifically bind to target antigens can be derived a) from known antibodies to these antigens or b) from new antibodies or antibody fragments obtained by de novo immunization methods using the antigen proteins or fragments thereof, by phage display, or other routine methods. The antibodies from which the binding domains for the bispecific antigen binding proteins are derived can be monoclonal antibodies, polyclonal antibodies, recombinant antibodies, human antibodies, or humanized antibodies. In certain embodiments, the antibodies from which the binding domains are derived are monoclonal antibodies. In these and other embodiments, the antibodies are human antibodies or humanized antibodies and can be of the IgG1-, IgG2-, IgG3-, or IgG4-type.

The term "monoclonal antibody" (or "mAb") as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against an individual antigenic site or epitope, in contrast to polyclonal antibody preparations that typically include different antibodies directed against different epitopes. Monoclonal antibodies may be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag 4 1, Sp210-Ag14, FO, NSO/U, MPC-11, MPC11-X45-GTG 1.7 and S194/5XXO Bul; examples of cell lines used in rat fusions include R210.RCY3, Y3-Ag 1.2.3, IR983F and 4B210. Other cell lines useful for cell fusions are U-266, GM1500-GRG2, LICR-LON-HMy2 and UC729-6.

In some instances, a hybridoma cell line is produced by immunizing an animal (e.g., a transgenic animal having human immunoglobulin sequences) with target antigen; harvesting spleen cells from the immunized animal; fusing the harvested spleen cells to a myeloma cell line, thereby generating hybridoma cells; establishing hybridoma cell lines from the hybridoma cells, and identifying a hybridoma cell line that produces an antibody that binds target antigen.

Monoclonal antibodies secreted by a hybridoma cell line can be purified using any technique known in the art, such as protein A-Sepharose, hydroxylapatite chromatography, gel electrophoresis, dialysis, or affinity chromatography. Hybridomas or mAbs may be further screened to identify mAbs with particular properties, such as the ability to bind cells expressing target antigen, ability to block or interfere with the binding of the target antigen ligand to their respective receptors, or the ability to functionally block either of the receptors, e.g., a cAMP assay.

In some embodiments, the binding domains of the bispecific antigen binding proteins of the invention may be derived from humanized antibodies. A "humanized antibody" refers to an antibody in which regions (e.g. framework regions) have been modified to comprise corresponding regions from a human immunoglobulin. Generally, a humanized antibody can be produced from a monoclonal antibody raised initially in a non-human animal. Certain amino acid residues in this monoclonal antibody, typically from non-antigen recognizing portions of the antibody, are modified to be homologous to corresponding residues in a human antibody of corresponding isotype. Humanization can be performed, for example, using various methods by substituting at least a portion of a rodent variable region for the corresponding regions of a human antibody (see, e.g., U.S. Pat. Nos. 5,585,089 and 5,693,762; Jones et al., Nature, Vol. 321:522-525, 1986; Riechmann et al., Nature, Vol. 332:323-27, 1988; Verhoeyen et al., Science, Vol. 239:1534-1536, 1988). The CDRs of light and heavy chain variable regions of antibodies generated in another species can be grafted to consensus human FRs. To create consensus human FRs, FRs from several human heavy chain or light chain amino acid sequences may be aligned to identify a consensus amino acid sequence.

New antibodies generated against the target antigen from which binding domains for the bispecific antigen binding proteins of the invention can be derived can be fully human antibodies. A "fully human antibody" is an antibody that comprises variable and constant regions derived from or indicative of human germ line immunoglobulin sequences. One specific means provided for implementing the production of fully human antibodies is the "humanization" of the mouse humoral immune system. Introduction of human immunoglobulin (Ig) loci into mice in which the endogenous Ig genes have been inactivated is one means of producing fully human monoclonal antibodies (mAbs) in mouse, an animal that can be immunized with any desirable antigen. Using fully human antibodies can minimize the immunogenic and allergic responses that can sometimes be caused by administering mouse or mouse-derived mAbs to humans as therapeutic agents.

Fully human antibodies can be produced by immunizing transgenic animals (usually mice) that are capable of producing a repertoire of human antibodies in the absence of endogenous immunoglobulin production. Antigens for this purpose typically have six or more contiguous amino acids, and optionally are conjugated to a carrier, such as a hapten. See, e.g., Jakobovits et al., 1993, Proc. Natl. Acad. Sci. USA 90:2551-2555; Jakobovits et al., 1993, Nature 362:255-258;

and Bruggermann et al., 1993, Year in Immunol. 7:33. In one example of such a method, transgenic animals are produced by incapacitating the endogenous mouse immunoglobulin loci encoding the mouse heavy and light immunoglobulin chains therein, and inserting into the mouse genome large fragments of human genome DNA containing loci that encode human heavy and light chain proteins. Partially modified animals, which have less than the full complement of human immunoglobulin loci, are then cross-bred to obtain an animal having all of the desired immune system modifications. When administered an immunogen, these transgenic animals produce antibodies that are immunospecific for the immunogen but have human rather than murine amino acid sequences, including the variable regions. For further details of such methods, see, for example, WO96/33735 and WO94/02602. Additional methods relating to transgenic mice for making human antibodies are described in U.S. Pat. Nos. 5,545,807; . 6,713,610; 6,673,986; 6,162,963; 5,939,598; 5,545,807; 6,300,129; 6,255,458; 5,877,397; 5,874,299 and U.S. Pat. No. 5,545,806; in PCT publications WO91/10741, WO90/04036, WO 94/02602, WO 96/30498, WO 98/24893 and in EP 546073B1 and EP 546073A1.

The transgenic mice described above, referred to herein as "HuMab" mice, contain a human immunoglobulin gene minilocus that encodes unrearranged human heavy (mu and gamma) and kappa light chain immunoglobulin sequences, together with targeted mutations that inactivate the endogenous mu and kappa chain loci (Lonberg et al., 1994, Nature 368:856-859). Accordingly, the mice exhibit reduced expression of mouse IgM or kappa and in response to immunization, and the introduced human heavy and light chain transgenes undergo class switching and somatic mutation to generate high affinity human IgG kappa monoclonal antibodies (Lonberg et al., supra.; Lonberg and Huszar, 1995, Intern. Rev. Immunol. 13:65-93; Harding and Lonberg, 1995, Ann. N. Y Acad. Sci. 764:536-546). The preparation of HuMab mice is described in detail in Taylor et al., 1992, Nucleic Acids Research 20:6287-6295; Chen et al., 1993, International Immunology 5:647-656; Tuaillon et al., 1994, J. Immunol. 152:2912-2920; Lonberg et al., 1994, Nature 368:856-859; Lonberg, 1994, Handbook of Exp. Pharmacology 113:49-101; Taylor et al., 1994, International Immunology 6:579-591; Lonberg and Huszar, 1995, Intern. Rev. Immunol. 13:65-93; Harding and Lonberg, 1995, Ann. N. Y Acad. Sci. 764:536-546; Fishwild et al., 1996, Nature Biotechnology 14:845-851; the foregoing references are hereby incorporated by reference in their entirety for all purposes. See, further U.S. Pat. Nos. 5,545,806; 5,569,825; 5,625,126; 5,633,425; 5,789,650; 5,877,397; 5,661,016; 5,814,318; 5,874,299; and 5,770,429; as well as U.S. Pat. No. 5,545,807; International Publication Nos. WO 93/1227; WO 92/22646; and WO 92/03918, the disclosures of all of which are hereby incorporated by reference in their entirety for all purposes. Technologies utilized for producing human antibodies in these transgenic mice are disclosed also in WO 98/24893, and Mendez et al., 1997, Nature Genetics 15:146-156, which are hereby incorporated by reference.

Human-derived antibodies can also be generated using phage display techniques. Phage display is described in e.g., Dower et al., WO 91/17271, McCafferty et al., WO 92/01047, and Caton and Koprowski, Proc. Natl. Acad. Sci. USA, 87:6450-6454 (1990), each of which is incorporated herein by reference in its entirety. The antibodies produced by phage technology are usually produced as antigen binding fragments, e.g. Fv or Fab fragments, in bacteria and thus lack effector functions. Effector functions can be introduced by one of two strategies: The fragments can be engineered either into complete antibodies for expression in mammalian cells, or into bispecific antibody fragments with a second binding site capable of triggering an effector function, if desired. Typically, the Fd fragment (VH-CH1) and light chain (VL-CL) of antibodies are separately cloned by PCR and recombined randomly in combinatorial phage display libraries, which can then be selected for binding to a particular antigen. The antibody fragments are expressed on the phage surface, and selection of Fv or Fab (and therefore the phage containing the DNA encoding the antibody fragment) by antigen binding is accomplished through several rounds of antigen binding and re-amplification, a procedure termed panning. Antibody fragments specific for the antigen are enriched and finally isolated. Phage display techniques can also be used in an approach for the humanization of rodent monoclonal antibodies, called "guided selection" (see Jespers, L. S., et al., Bio/Technology 12, 899-903 (1994)). For this, the Fd fragment of the mouse monoclonal antibody can be displayed in combination with a human light chain library, and the resulting hybrid Fab library may then be selected with antigen. The mouse Fd fragment thereby provides a template to guide the selection. Subsequently, the selected human light chains are combined with a human Fd fragment library. Selection of the resulting library yields entirely human Fab.

In certain embodiments, the bispecific antigen binding proteins of the invention are antibodies. As used herein, the term "antibody" refers to a tetrameric immunoglobulin protein comprising two light chain polypeptides (about 25 kDa each) and two heavy chain polypeptides (about 50-70 kDa each). The term "light chain" or "immunoglobulin light chain" refers to a polypeptide comprising, from amino terminus to carboxyl terminus, a single immunoglobulin light chain variable region (VL) and a single immunoglobulin light chain constant domain (CL). The immunoglobulin light chain constant domain (CL) can be kappa (κ) or lambda (2). The term "heavy chain" or "immunoglobulin heavy chain" refers to a polypeptide comprising, from amino terminus to carboxyl terminus, a single immunoglobulin heavy chain variable region (VH), an immunoglobulin heavy chain constant domain 1 (CH1), an immunoglobulin hinge region, an immunoglobulin heavy chain constant domain 2 (CH2), an immunoglobulin heavy chain constant domain 3 (CH3), and optionally an immunoglobulin heavy chain constant domain 4 (CH4). Heavy chains are classified as mu (μ), delta (Δ), gamma (γ), alpha (α), and epsilon (ε), and define the antibody's isotype as IgM, IgD, IgG, IgA, and IgE, respectively. The IgG-class and IgA-class antibodies are further divided into subclasses, namely, IgG1, IgG2, IgG3, and IgG4, and IgAQ1 and IgA2, respectively. The heavy chains in IgG, IgA, and IgD antibodies have three domains (CH1, CH2, and CH3), whereas the heavy chains in IgM and IgE antibodies have four domains (CH1, CH2, CH3, and CH4). The immunoglobulin heavy chain constant domains can be from any immunoglobulin isotype, including subtypes. The antibody chains are linked together via inter-polypeptide disulfide bonds between the CL domain and the CH1 domain (i.e. between the light and heavy chain) and between the hinge regions of the antibody heavy chains.

In particular embodiments, the bispecific antigen binding proteins of the invention are heterodimeric antibodies (used interchangeably herein with "hetero immunoglobulins" or "hetero Igs"), which refer to antibodies comprising two different light chains and two different heavy chains.

The heterodimeric antibodies can comprise any immunoglobulin constant region. The term "constant region" as used herein refers to all domains of an antibody other than the variable region. The constant region is not involved directly in binding of an antigen, but exhibits various effector functions. As described above, antibodies are divided into particular isotypes (IgA, IgD, IgE, IgG, and IgM) and subtypes (IgG1, IgG2, IgG3, IgG4, IgAQ1 IgA2) depending on the amino acid sequence of the constant region of their heavy chains. The light chain constant region can be, for example, a kappa- or lambda-type light chain constant region, e.g., a human kappa- or lambda-type light chain constant region, which are found in all five antibody isotypes.

The heavy chain constant region of the heterodimeric antibodies can be, for example, an alpha-, delta-, epsilon-, gamma-, or mu-type heavy chain constant region, e.g., a human alpha-, delta-, epsilon-, gamma-, or mu-type heavy chain constant region. In some embodiments, the heterodimeric antibodies comprise a heavy chain constant region from an IgG1, IgG2, IgG3, or IgG4 immunoglobulin. In one embodiment, the heterodimeric antibody comprises a heavy chain constant region from a human IgG1 immunoglobulin. In another embodiment, the heterodimeric antibody comprises a heavy chain constant region from a human IgG2 immunoglobulin.

In one embodiment, a bispecific antibody of this disclosure is a Duobody™ Duobodies can be made by the Duo-Body™ technology platform (Genmab A/S) as described, e.g., in International Publication Nos. WO 2008/119353, WO 2011/131746, WO 2011/147986, and WO 2013/060867, Labrijn A F et al., PNAS, 110 (13): 5145-5150 (2013), Gramer et al., mAbs, 5 (6): 962-973 (2013), and Labrijn et al., Nature Protocols, 9 (10): 2450-2463 (2014). This technology can be used to combine one half of a first monospecific antibody containing two heavy and two light chains with one half of a second monospecific antibody containing two heavy and two light chains. The resultant heterodimer contains one heavy chain and one light chain from the first antibody paired with one heavy chain and one light chain from the second antibody. When both of the monospecific antibodies recognize different epitopes on different antigens, the resultant heterodimer is a bispecific antibody.

For the DuoBody™ platform, each of the monospecific antibodies includes a heavy chain constant region with a single point mutation in the CH3 domain. These point mutations permit a stronger interaction between the CH3 domains in the resulting bispecific antibody than between the CH3 domains in either of the monospecific antibodies without the mutations. The single point mutation in each monospecific antibody can be at residue 366, 368, 370, 399, 405, 407, or 409 (EU numbering) in the CH3 domain of the heavy chain constant region (see, WO 2011/131746). Furthermore, the single point mutation is located at a different residue in one monospecific antibody relative to the other monospecific antibody. For example, one monospecific antibody can comprise the mutation F405L (EU numbering; phenylalanine to leucine mutation at residue 405), or one of F405A, F405D, F405E, F405H, F405I, F405K, F405M, F405N, F405Q, F405S, F405T, F405V, F405W, and F405Y mutations, while the other monospecific antibody can comprise the mutation K409R (EU numbering; lysine to arginine mutation at residue 409). The heavy chain constant regions of the monospecific antibodies can be an IgG1, IgG2, IgG3, or IgG4 isotype (e.g., a human IgG1 isotype), and a bispecific antibody produced by the DuoBody™ technology can be modified to alter (e.g., reduce) Fc-mediated effector functions and/or improve half-life. One method of making a Duobody™ involves the following: (i) separate expression of two parental IgGls containing single matching point mutations (i.e., K409R and F405L (or one of F405A, F405D, F405E, F405H, F405I, F405K, F405M, F405N, F405Q, F405S, F405T, F405V, F405W, and F405Y mutations) (EU numbering)) in the CH3 domain; (ii) mixing of parental IgGls under permissive redox conditions in vitro to enable recombination of half-molecules; (iii) removal of the reductant to allow re-oxidation of interchain disulfide bonds; and (iv) analysis of exchange efficiency and final product using chromatography-based or mass spectrometry (MS)-based methods (see, Labrijn et al., Nature Protocols, 9 (10): 2450-2463 (2014)).

Another exemplary method of making bispecific antibodies is by the knobs-into-holes technology (Ridgway et al., Protein Eng., 9:617-621 (1996); WO 2006/028936). The mispairing problem of Ig heavy chains that is a chief drawback for making bispecific antibodies is reduced in this technology by mutating selected amino acids forming the interface of the CH3 domains in IgG. At positions within the CH3 domain at which the two heavy chains interact directly, an amino acid with a small side chain (hole) is introduced into the sequence of one heavy chain and an amino acid with a large side chain (knob) into the counterpart interacting residue location on the other heavy chain. In some instances, antibodies of the disclosure have immunoglobulin chains in which the CH3 domains have been modified by mutating selected amino acids that interact at the interface between two polypeptides so as to preferentially form a bispecific antibody. The bispecific antibodies can be composed of immunoglobulin chains of the same subclass or different subclasses. In one instance, a bispecific antibody that binds to gp120 and CD3 comprises a T366W (EU numbering) mutation in the "knobs chain" and T366S, L368A, Y407V 9EU numbering) mutations in the "hole chain." In certain embodiments, an additional interchain disulfide bridge is introduced between the CH3 domains by, e.g., introducing a Y349C mutation into the "knobs chain" and a E356C mutation or a S354C mutation into the "hole chain." In certain embodiments, R409D, K370E mutations are introduced in the "knobs chain" and D399K, E357K mutations in the "hole chain." In other embodiments, Y349C, T366W mutations are introduced in one of the chains and E356C, T366S, L368A, Y407V mutations in the counterpart chain. In some embodiments. Y349C, T366W mutations are introduced in one chain and S354C, T366S, L368A, Y407V mutations in the counterpart chain. In some embodiments, Y349C, T366W mutations are introduced in one chain and S354C, T366S, L368A, Y407V mutations in the counterpart chain. In yet other embodiments, Y349C, T366W mutations are introduced in one chain and S354C, T366S, L368A, Y407V mutations in the counterpart chain (all EU numbering).

Yet another method for making bispecific antibodies is the CrossMab technology. CrossMab are chimeric antibodies constituted by the halves of two full-length antibodies. For correct chain pairing, it combines two technologies: (i) the knob-into-hole which favors a correct pairing between the two heavy chains; and (ii) an exchange between the heavy and light chains of one of the two Fabs to introduce an asymmetry which avoids light-chain mispairing. See, Ridgway et al., Protein Eng., 9:617-621 (1996); Schaefer et al., PNAS, 108:11187-11192 (2011). CrossMabs can combine two or more antigen-binding domains for targeting two or more targets or for introducing bivalency towards one target such as the 2:1 format.

To facilitate the association of a particular heavy chain with its cognate light chain, both the heavy and light chains may contain complimentary amino acid substitutions. As used herein, "complimentary amino acid substitutions" refer to a substitution to a positively-charged amino acid in one chain paired with a negatively-charged amino acid substitution in the other chain. For example, in some embodiments, the heavy chain comprises at least one amino acid substitution to introduce a charged amino acid and the corresponding light chain comprises at least one amino acid substitution to introduce a charged amino acid, wherein the charged amino acid introduced into the heavy chain has the opposite charge of the amino acid introduced into the light chain. In certain embodiments, one or more positively-charged residues (e.g., lysine, histidine or arginine) can be introduced into a first light chain (LC1) and one or more negatively-charged residues (e.g., aspartic acid or glutamic acid) can be introduced into the companion heavy chain (HC1) at the binding interface of LC1/HC1, whereas one or more negatively-charged residues (e.g., aspartic acid or glutamic acid) can be introduced into a second light chain (LC2) and one or more positively-charged residues (e.g., lysine, histidine or arginine) can be introduced into the companion heavy chain (HC2) at the binding interface of LC2/HC2. The electrostatic interactions will direct the LC1 to pair with HC1 and LC2 to pair with HC2, as the opposite charged residues (polarity) at the interface attract. The heavy/light chain pairs having the same charged residues (polarity) at an interface (e.g. LC1/HC2 and LC2/HC1) will repel, resulting in suppression of the unwanted HC/LC pairings.

In these and other embodiments, the CH1 domain of the heavy chain or the CL domain of the light chain comprises an amino acid sequence differing from wild-type IgG amino acid sequence such that one or more positively-charged amino acids in wild-type IgG amino acid sequence is replaced with one or more negatively-charged amino acids. Alternatively, the CH1 domain of the heavy chain or the CL domain of the light chain comprises an amino acid sequence differing from wild-type IgG amino acid sequence such that one or more negatively-charged amino acids in wild-type IgG amino acid sequence is replaced with one or more positively-charged amino acids. In some embodiments, one or more amino acids in the CH1 domain of the first and/or second heavy chain in the heterodimeric antibody at an EU position selected from F126, P127, L128, A141, L145, K147, D148, H168, F170, P171, V173, Q175, S176, S183, V185 and K213 is replaced with a charged amino acid. In certain embodiments, a preferred residue for substitution with a negatively- or positively-charged amino acid is S183 (EU numbering system). In some embodiments, S183 is substituted with a positively-charged amino acid. In alternative embodiments, S183 is substituted with a negatively-charged amino acid. For instance, in one embodiment, S183 is substituted with a negatively-charged amino acid (e.g. S183E) in the first heavy chain, and S183 is substituted with a positively-charged amino acid (e.g. S183K) in the second heavy chain.

In embodiments in which the light chain is a kappa light chain, one or more amino acids in the CL domain of the first and/or second light chain in the heterodimeric antibody at a position (EU and Kabat numbering in a kappa light chain) selected from F116, F118, S121, D122, E123, Q124, S131, V133, L135, N137, N138, Q160, S162, T164, S174 and S176 is replaced with a charged amino acid. In embodiments in which the light chain is a lambda light chain, one or more amino acids in the CL domain of the first and/or second light chain in the heterodimeric antibody at a position (Kabat numbering in a lambda chain) selected from T116, F118, S121, E123, E124, K129, T131, V133, L135, S137, E160, T162, S165, Q167, A174, S176 and Y178 is replaced with a charged amino acid. In some embodiments, a preferred residue for substitution with a negatively- or positively-charged amino acid is S176 (EU and Kabat numbering system) of the CL domain of either a kappa or lambda light chain. In certain embodiments, S176 of the CL domain is replaced with a positively-charged amino acid. In alternative embodiments, S176 of the CL domain is replaced with a negatively-charged amino acid. In one embodiment, S176 is substituted with a positively-charged amino acid (e.g. S176K) in the first light chain, and S176 is substituted with a negatively-charged amino acid (e.g. S176E) in the second light chain.

In addition to or as an alternative to the complimentary amino acid substitutions in the CH1 and CL domains, the variable regions of the light and heavy chains in the heterodimeric antibody may contain one or more complimentary amino acid substitutions to introduce charged amino acids. For instance, in some embodiments, the VH region of the heavy chain or the VL region of the light chain of a heterodimeric antibody comprises an amino acid sequence differing from wild-type IgG amino acid sequence such that one or more positively-charged amino acids in wild-type IgG amino acid sequence is replaced with one or more negatively-charged amino acids. Alternatively, the VH region of the heavy chain or the VL region of the light chain comprises an amino acid sequence differing from wild-type IgG amino acid sequence such that one or more negatively-charged amino acids in wild-type IgG amino acid sequence is replaced with one or more positively-charged amino acids.

V region interface residues (i.e., amino acid residues that mediate assembly of the VH and VL regions) within the VH region include Kabat positions 1, 3, 35, 37, 39, 43, 44, 45, 46, 47, 50, 59, 89, 91, and 93. One or more of these interface residues in the VH region can be substituted with a charged (positively- or negatively-charged) amino acid. In certain embodiments, the amino acid at Kabat position 39 in the VH region of the first and/or second heavy chain is substituted for a positively-charged amino acid, e.g., lysine. In alternative embodiments, the amino acid at Kabat position 39 in the VH region of the first and/or second heavy chain is substituted for a negatively-charged amino acid, e.g., glutamic acid. In some embodiments, the amino acid at Kabat position 39 in the VH region of the first heavy chain is substituted for a negatively-charged amino acid (e.g. G39E), and the amino acid at Kabat position 39 in the VH region of the second heavy chain is substituted for a positively-charged amino acid (e.g. G39K). In some embodiments, the amino acid at Kabat position 44 in the VH region of the first and/or second heavy chain is substituted for a positively-charged amino acid, e.g., lysine. In alternative embodiments, the amino acid at Kabat position 44 in the VH region of the first and/or second heavy chain is substituted for a negatively-charged amino acid, e.g., glutamic acid. In certain embodiments, the amino acid at Kabat position 44 in the VH region of the first heavy chain is substituted for a negatively-charged amino acid (e.g. G44E), and the amino acid at Kabat position 44 in the VH region of the second heavy chain is substituted for a positively-charged amino acid (e.g. G44K).

V region interface residues (i.e., amino acid residues that mediate assembly of the VH and VL regions) within the VL region include Kabat positions 32, 34, 35, 36, 38, 41, 42, 43, 44, 45, 46, 48, 49, 50, 51, 53, 54, 55, 56, 57, 58, 85, 87, 89, 90, 91, and 100. One or more interface residues in the VL region can be substituted with a charged amino acid, preferably an amino acid that has an opposite charge to those introduced into the VH region of the cognate heavy chain. In some embodiments, the amino acid at Kabat position 100 in the VL region of the first and/or second light chain is substituted for a positively-charged amino acid, e.g., lysine. In alternative embodiments, the amino acid at Kabat position 100 in the VL region of the first and/or second light chain is substituted for a negative-charged amino acid, e.g., glutamic acid. In certain embodiments, the amino acid at Kabat position 100 in the VL region of the first light chain is substituted for a positively-charged amino acid (e.g. G100K), and the amino acid at Kabat position 100 in the VL region of the second light chain is substituted for a negatively-charged amino acid (e.g. G100E).

In certain embodiments, a heterodimeric antibody of the invention comprises a first heavy chain and a second heavy chain and a first light chain and a second light chain, wherein the first heavy chain comprises amino acid substitutions at positions 44 (Kabat), 183 (EU), 392 (EU) and 409 (EU), wherein the second heavy chain comprises amino acid substitutions at positions 44 (Kabat), 183 (EU), 356 (EU) and 399 (EU), wherein the first and second light chains comprise an amino acid substitution at positions 100 (Kabat) and 176 (EU), and wherein the amino acid substitutions introduce a charged amino acid at said positions. In related embodiments, the glycine at position 44 (Kabat) of the first heavy chain is replaced with glutamic acid, the glycine at position 44 (Kabat) of the second heavy chain is replaced with lysine, the glycine at position 100 (Kabat) of the first light chain is replaced with lysine, the glycine at position 100 (Kabat) of the second light chain is replaced with glutamic acid, the serine at position 176 (EU) of the first light chain is replaced with lysine, the serine at position 176 (EU) of the second light chain is replaced with glutamic acid, the serine at position 183 (EU) of the first heavy chain is replaced with glutamic acid, the lysine at position 392 (EU) of the first heavy chain is replaced with aspartic acid, the lysine at position 409 (EU) of the first heavy chain is replaced with aspartic acid, the serine at position 183 (EU) of the second heavy chain is replaced with lysine, the glutamic acid at position 356 (EU) of the second heavy chain is replaced with lysine, and/or the aspartic acid at position 399 (EU) of the second heavy chain is replaced with lysine.

As used herein, the term "Fc region" refers to the C-terminal region of an immunoglobulin heavy chain which may be generated by papain digestion of an intact antibody. The Fc region of an immunoglobulin generally comprises two constant domains, a CH2 domain and a CH3 domain, and optionally comprises a CH4 domain. In certain embodiments, the Fc region is an Fc region from an IgG1, IgG2, IgG3, or IgG4 immunoglobulin. In some embodiments, the Fc region comprises CH2 and CH3 domains from a human IgG1 or human IgG2 immunoglobulin. The Fc region may retain effector function, such as C1q binding, complement dependent cytotoxicity (CDC), Fc receptor binding, antibody-dependent cell-mediated cytotoxicity (ADCC), and phagocytosis. In other embodiments, the Fc region may be modified to reduce or eliminate effector function as described in further detail herein.

In some embodiments of the antigen binding proteins of the invention, the binding domain positioned at the carboxyl terminus of the Fc region (i.e. the carboxyl-terminal binding domain) is a scFv. In certain embodiments, the scFv comprises a heavy chain variable region (VH) and light chain variable region (VL) connected by a peptide linker. The variable regions may be oriented within the scFv in a VH-VL or VL-VH orientation. For instance, in one embodiment, the scFv comprises, from N-terminus to C-terminus, a VH region, a peptide linker, and a VL region. In another embodiment, the scFv comprises, from N-terminus to C-terminus, a VL region, a peptide linker, and a VH region. The VH and VL regions of the scFv may contain one or more cysteine substitutions to permit disulfide bond formation between the VH and VL regions. Such cysteine clamps stabilize the two variable domains in the antigen-binding configuration. In one embodiment, position 44 (Kabat numbering) in the VH region and position 100 (Kabat numbering) in the VL region are each substituted with a cysteine residue.

In certain embodiments, the scFv is fused or otherwise connected at its amino terminus to the carboxyl terminus of the Fc region (e.g. the carboxyl terminus of the CH3 domain) through a peptide linker. Thus, in one embodiment, the scFv is fused to an Fc region such that the resulting fusion protein comprises, from N-terminus to C-terminus, a CH2 domain, a CH3 domain, a first peptide linker, a VH region, a second peptide linker, and a VL region. In another embodiment, the scFv is fused to an Fc region such that the resulting fusion protein comprises, from N-terminus to C-terminus, a CH2 domain, a CH3 domain, a first peptide linker, a VL region, a second peptide linker, and a VH region. A "fusion protein" is a protein that includes polypeptide components derived from more than one parental protein or polypeptide. Typically, a fusion protein is expressed from a fusion gene in which a nucleotide sequence encoding a polypeptide sequence from one protein is appended in frame with, and optionally separated by a linker from, a nucleotide sequence encoding a polypeptide sequence from a different protein. The fusion gene can then be expressed by a recombinant host cell to produce the single fusion protein.

A "peptide linker" refers to an oligopeptide of about 2 to about 50 amino acids that covalently joins one polypeptide to another polypeptide. The peptide linkers can be used to connect the VH and VL domains within the scFv. The peptide linkers can also be used to connect a scFv, Fab fragment, or other functional antibody fragment to the amino terminus or carboxyl terminus of an Fc region to create bispecific antigen binding proteins as described herein. Preferably, the peptide linkers are at least 5 amino acids in length. In certain embodiments, the peptide linkers are from about 5 amino acids in length to about 40 amino acids in length. In other embodiments, the peptide linkers are from about 8 amino acids in length to about 30 amino acids in length. In still other embodiments, the peptide linkers are from about 10 amino acids in length to about 20 amino acids in length.

Preferably, but not necessarily, the peptide linker comprises amino acids from among the twenty canonical amino acids, particularly cysteine, glycine, alanine, proline, asparagine, glutamine, and/or serine. In certain embodiments, the peptide linker is comprised of a majority of amino acids that are sterically unhindered, such as glycine, serine, and alanine. Thus, linkers that are preferred in some embodiments, include polyglycines, polyserines, and polyalanines, or combinations of any of these. Some exemplary peptide linkers include, but are not limited to, poly(Gly)$_{2-8}$, particularly (Gly)$_3$ (SEQ ID NO: 22), (Gly)$_4$ (SEQ ID NO: 23), (Gly)$_5$ (SEQ ID NO: 24), (Gly)$_6$ (SEQ ID NO: 25) and (Gly)$_7$ (SEQ ID NO: 26), as well as, poly(Gly)$_4$Ser, poly(Gly-Ala)$_{2-4}$ and poly(Ala)$_{2-8}$. In certain embodiments, the peptide linker is (Gly$_x$Ser)$_n$ where x=3 or 4 and n=2, 3, 4, 5 or 6. Such peptide linkers include "L5" (GGGGS or "G$_4$S"; SEQ ID NO: 27), "L9" (GGGSGGGGS; or "G₃SG₄S"; SEQ ID NO: 28), "L10" (GGGGSGGGGS; or "(G₄S)₂"; SEQ ID NO: 29), "L15" (GGGGSGGGGSGGGGS; or "(G₄S)₃"; SEQ ID NO: 31), and "L25" (GGGGSGGGGSGGGGSGGGGSGGGGS; or "(G₄S)₅"; SEQ ID NO:32). In some embodiments, the peptide linker joining the VH and VL regions within the scFv is a L15 or (G₄S)₃ linker (SEQ ID NO: 31). In these and other embodiments, the peptide linker joining the carboxyl-terminal binding domain (e.g. scFv or Fab) to the C-terminus of the Fc region is a L9 or G₃SG₄S linker (SEQ ID NO: 28) or a L10 (G₄S)₂ linker (SEQ ID NO: 29).

Other specific examples of peptide linkers that may be used in the bispecific antigen binding proteins of the invention include (Gly)₅Ly₅ (SEQ ID NO: 1); (Gly)₅LysArg (SEQ ID NO: 2); (Gly)₃Lys(Gly)₄ (SEQ ID NO: 3); (Gly)₃AsnGlySer(Gly)₂ (SEQ ID NO: 4); (Gly)₃Cys(Gly)₄ (SEQ ID NO: 5); GlyProAsnGlyGly (SEQ ID NO: 6); GGEGGG (SEQ ID NO: 7); GGEEEGGG (SEQ ID NO: 8); GEEEG (SEQ ID NO: 9); GEEE (SEQ ID NO: 10); GGDGGG (SEQ ID NO: 11); GGDDDGG (SEQ ID NO: 12); GDDDG (SEQ ID NO: 13); GDDD (SEQ ID NO: 14); GGGGSDDSDE-GSDGEDGGGGS (SEQ ID NO: 15); WEWEW (SEQ ID NO: 16); FEFEF (SEQ ID NO: 17); EEEWWW (SEQ ID NO: 18); EEEFFF (SEQ ID NO: 19); WWEEEWW (SEQ ID NO: 20); and FFEEEFF (SEQ ID NO: 21).

The heavy chain constant regions or the Fc regions of the bispecific antigen binding proteins described herein may comprise one or more amino acid substitutions that affect the glycosylation and/or effector function of the antigen binding protein. One of the functions of the Fc region of an immunoglobulin is to communicate to the immune system when the immunoglobulin binds its target. This is commonly referred to as "effector function." Communication leads to antibody-dependent cellular cytotoxicity (ADCC), antibody-dependent cellular phagocytosis (ADCP), and/or complement dependent cytotoxicity (CDC). ADCC and ADCP are mediated through the binding of the Fc region to Fc receptors on the surface of cells of the immune system. CDC is mediated through the binding of the Fc with proteins of the complement system, e.g., C1q. In some embodiments, the bispecific antigen binding proteins of the invention comprise one or more amino acid substitutions in the constant region to enhance effector function, including ADCC activity, CDC activity, ADCP activity, and/or the clearance or half-life of the antigen binding protein. Exemplary amino acid substitutions (EU numbering) that can enhance effector function include, but are not limited to, E233L, L234I, L234Y, L235S, G236A, S239D, F243L, F243V, P247I, D280H, K290S, K290E, K290N, K290Y, R292P, E294L, Y296W, S298A, S298D, S298V, S298G, S298T, T299A, Y300L, V3051, Q311M, K326A, K326E, K326W, A330S, A330L, A330M, A330F, I332E, D333A, E333S, E333A, K334A, K334V, A339D, A339Q, P396L, or combinations of any of the foregoing.

In other embodiments, the bispecific antigen binding proteins of the invention comprise one or more amino acid substitutions in the constant region to reduce effector function. Exemplary amino acid substitutions (EU numbering) that can reduce effector function include, but are not limited to, C220S, C226S, C229S, E233P, L234A, L234V, V234A, L234F, L235A, L235E, G237A, P238S, S267E, H268Q, N297A, N297G, V309L, E318A, L328F, A330S, A331S, P331S or combinations of any of the foregoing.

Glycosylation can contribute to the effector function of antibodies, particularly IgG1 antibodies. Thus, in some embodiments, the bispecific antigen binding proteins of the invention may comprise one or more amino acid substitutions that affect the level or type of glycosylation of the binding proteins. Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

In certain embodiments, glycosylation of the bispecific antigen binding proteins described herein is increased by adding one or more glycosylation sites, e.g., to the Fc region of the binding protein. Addition of glycosylation sites to the antigen binding protein can be conveniently accomplished by altering the amino acid sequence such that it contains one or more of the above-described tri-peptide sequences (for N-linked glycosylation sites). The alteration may also be made by the addition of, or substitution by, one or more serine or threonine residues to the starting sequence (for O-linked glycosylation sites). For ease, the antigen binding protein amino acid sequence may be altered through changes at the DNA level, particularly by mutating the DNA encoding the target polypeptide at preselected bases such that codons are generated that will translate into the desired amino acids.

The invention also encompasses production of bispecific antigen binding protein molecules with altered carbohydrate structure resulting in altered effector activity, including antigen binding proteins with absent or reduced fucosylation that exhibit improved ADCC activity. Various methods are known in the art to reduce or eliminate fucosylation. For example, ADCC effector activity is mediated by binding of the antibody molecule to the FcγRIII receptor, which has been shown to be dependent on the carbohydrate structure of the N-linked glycosylation at the N297 residue of the CH2 domain. Non-fucosylated antibodies bind this receptor with increased affinity and trigger FcγRIII-mediated effector functions more efficiently than native, fucosylated antibodies. For example, recombinant production of non-fucosylated antibody in CHO cells in which the alpha-1,6-fucosyl transferase enzyme has been knocked out results in antibody with 100-fold increased ADCC activity (see Yamane-Ohnuki et al., Biotechnol Bioeng. 87 (5): 614-22, 2004). Similar effects can be accomplished through decreasing the activity of alpha-1,6-fucosyl transferase enzyme or other enzymes in the fucosylation pathway, e.g., through siRNA or antisense RNA treatment, engineering cell lines to knockout the enzyme(s), or culturing with selective glycosylation inhibitors (see Rothman et al., Mol Immunol. 26 (12): 1113-23, 1989). Some host cell strains, e.g. Lec13 or rat hybridoma YB2/0 cell line naturally produce antibodies with lower fucosylation levels (see Shields et al., J Biol Chem. 277 (30): 26733-40, 2002 and Shinkawa et al., J Biol Chem. 278 (5): 3466-73, 2003). An increase in the level of bisected carbohydrate, e.g. through recombinantly producing antibody in cells that overexpress GnTIII enzyme, has also been determined to increase ADCC activity (see Umana et al., Nat Biotechnol. 17 (2): 176-80, 1999).

In other embodiments, glycosylation of the bispecific antigen binding proteins described herein is decreased or eliminated by removing one or more glycosylation sites, e.g., from the Fc region of the binding protein. Amino acid substitutions that eliminate or alter N-linked glycosylation sites can reduce or eliminate N-linked glycosylation of the antigen binding protein. In certain embodiments, the bispecific antigen binding proteins described herein comprise a mutation at position N297 (EU numbering), such as N297Q, N297A, or N297G. In one particular embodiment, the bispecific antigen binding proteins of the invention comprise a Fc region from a human IgG1 antibody with a N297G mutation. To improve the stability of molecules comprising a N297 mutation, the Fc region of the molecules may be further engineered. For instance, in some embodiments, one or more amino acids in the Fc region are substituted with cysteine to promote disulfide bond formation in the dimeric state. Residues corresponding to V259, A287, R292, V302, L306, V323, or 1332 (EU numbering) of an IgG1 Fc region may thus be substituted with cysteine. Preferably, specific pairs of residues are substituted with cysteine such that they preferentially form a disulfide bond with each other, thus limiting or preventing disulfide bond scrambling. Preferred pairs include, but are not limited to, A287C and L306C, V259C and L306C, R292C and V302C, and V323C and I332C. In particular embodiments, the bispecific antigen binding proteins described herein comprise a Fc region from a human lgG1 antibody with mutations at R292C and V302C. In such embodiments, the Fc region may also comprise a N297G mutation.

Modifications of the bispecific antigen binding proteins of the invention to increase serum half-life also may desirable, for example, by incorporation of or addition of a salvage receptor binding epitope (e.g., by mutation of the appropriate region or by incorporating the epitope into a peptide tag that is then fused to the antigen binding protein at either end or in the middle, e.g., by DNA or peptide synthesis; see, e.g., WO96/32478) or adding molecules such as PEG or other water soluble polymers, including polysaccharide polymers. The salvage receptor binding epitope preferably constitutes a region wherein any one or more amino acid residues from one or two loops of a Fc region are transferred to an analogous position in the antigen binding protein. Even more preferably, three or more residues from one or two loops of the Fc region are transferred. Still more preferred, the epitope is taken from the CH2 domain of the Fc region (e.g., an IgG Fc region) and transferred to the CH1, CH3, or VH region, or more than one such region, of the antigen binding protein. Alternatively, the epitope is taken from the CH2 domain of the Fc region and transferred to the CL region or VL region, or both, of the antigen binding protein. See International applications WO 97/34631 and WO 96/32478 for a description of Fc variants and their interaction with the salvage receptor.

The present invention includes one or more isolated nucleic acids encoding the bispecific antigen binding proteins and components thereof described herein. Nucleic acid molecules of the invention include DNA and RNA in both single-stranded and double-stranded form, as well as the corresponding complementary sequences. DNA includes, for example, cDNA, genomic DNA, chemically synthesized DNA, DNA amplified by PCR, and combinations thereof. The nucleic acid molecules of the invention include full-length genes or cDNA molecules as well as a combination of fragments thereof. The nucleic acids of the invention are preferentially derived from human sources, but the invention includes those derived from non-human species, as well.

Relevant amino acid sequences from an immunoglobulin or region thereof (e.g. variable region, Fc region, etc.) or polypeptide of interest may be determined by direct protein sequencing, and suitable encoding nucleotide sequences can be designed according to a universal codon table. Alternatively, genomic or cDNA encoding monoclonal antibodies from which the binding domains of the bispecific antigen binding proteins of the invention may be derived can be isolated and sequenced from cells producing such antibodies using conventional procedures (e.g., by using oligonucleotide probes that are capable of binding specifically to genes encoding the heavy and light chains of the monoclonal antibodies).

An "isolated nucleic acid," which is used interchangeably herein with "isolated polynucleotide," is a nucleic acid that has been separated from adjacent genetic sequences present in the genome of the organism from which the nucleic acid was isolated, in the case of nucleic acids isolated from naturally-occurring sources. In the case of nucleic acids synthesized enzymatically from a template or chemically, such as PCR products, cDNA molecules, or oligonucleotides for example, it is understood that the nucleic acids resulting from such processes are isolated nucleic acids. An isolated nucleic acid molecule refers to a nucleic acid molecule in the form of a separate fragment or as a component of a larger nucleic acid construct. In one preferred embodiment, the nucleic acids are substantially free from contaminating endogenous material. The nucleic acid molecule has preferably been derived from DNA or RNA isolated at least once in substantially pure form and in a quantity or concentration enabling identification, manipulation, and recovery of its component nucleotide sequences by standard biochemical methods (such as those outlined in Sambrook et al., Molecular Cloning: A Laboratory Manual, 2nd ed., Cold Spring Harbor Laboratory, Cold Spring Harbor, NY (1989)). Such sequences are preferably provided and/or constructed in the form of an open reading frame uninterrupted by internal non-translated sequences, or introns, that are typically present in eukaryotic genes. Sequences of non-translated DNA can be present 5' or 3' from an open reading frame, where the same do not interfere with manipulation or expression of the coding region. Unless specified otherwise, the left-hand end of any single-stranded polynucleotide sequence discussed herein is the 5' end; the left-hand direction of double-stranded polynucleotide sequences is referred to as the 5' direction. The direction of 5' to 3' production of nascent RNA transcripts is referred to as the transcription direction; sequence regions on the DNA strand having the same sequence as the RNA transcript that are 5' to the 5' end of the RNA transcript are referred to as "upstream sequences;" sequence regions on the DNA strand having the same sequence as the RNA transcript that are 3' to the 3' end of the RNA transcript are referred to as "downstream sequences."

The present invention also includes nucleic acids that hybridize under moderately stringent conditions, and more preferably highly stringent conditions, to nucleic acids encoding polypeptides as described herein. The basic parameters affecting the choice of hybridization conditions and guidance for devising suitable conditions are set forth by Sambrook, Fritsch, and Maniatis (1989, Molecular Cloning: A Laboratory Manual, Cold Spring Harbor Laboratory Press, Cold Spring Harbor, N.Y., chapters 9 and 11; and Current Protocols in Molecular Biology, 1995, Ausubel et al., eds., John Wiley & Sons, Inc., sections 2.10 and 6.3-6.4), and can be readily determined by those having ordinary skill in the art based on, for example, the length and/or base composition of the DNA. One way of achieving moderately stringent conditions involves the use of a prewashing solution containing 5×SSC, 0.5% SDS, 1.0 mM EDTA (pH 8.0), hybridization buffer of about 50% formamide, 6×SSC, and a hybridization temperature of about 55° C. (or other similar hybridization solutions, such as one containing about 50% formamide, with a hybridization temperature of about 42° C.), and washing conditions of about 60° C., in 0.5×SSC, 0.1% SDS. Generally, highly stringent conditions are defined as hybridization conditions as above, but with washing at approximately 68° C., 0.2×SSC, 0.1% SDS. SSPE (1×SSPE is 0.15M NaCl, 10 mM NaH$_2$PO$_4$, and 1.25 mM EDTA, pH 7.4) can be substituted for SSC (1×SSC is 0.15M NaCl and 15 mM sodium citrate) in the hybridization and wash buffers; washes are performed for 15 minutes after hybridization is complete. It should be understood that the wash temperature and wash salt concentration can be adjusted as necessary to achieve a desired degree of stringency by applying the basic principles that govern hybridization reactions and duplex stability, as known to those skilled in the art and described further below (see, e.g., Sambrook et al., 1989). When hybridizing a nucleic acid to a target nucleic acid of unknown sequence, the hybrid length is assumed to be that of the hybridizing nucleic acid. When nucleic acids of known sequence are hybridized, the hybrid length can be determined by aligning the sequences of the nucleic acids and identifying the region or regions of optimal sequence complementarity. The hybridization temperature for hybrids anticipated to be less than 50 base pairs in length should be 5 to 10° C. less than the melting temperature (Tm) of the hybrid, where Tm is determined according to the following equations. For hybrids less than 18 base pairs in length, Tm (° C.)=2 (# of A+T bases)+4 (# of G+C bases). For hybrids above 18 base pairs in length, Tm (° C.)=81.5+16.6 (log 10 [Na+])+0.41 (% G+C)-(600/N), where N is the number of bases in the hybrid, and [Na+] is the concentration of sodium ions in the hybridization buffer ([Na+] for 1×SSC=0.165M). Preferably, each such hybridizing nucleic acid has a length that is at least 15 nucleotides (or more preferably at least 18 nucleotides, or at least 20 nucleotides, or at least 25 nucleotides, or at least 30 nucleotides, or at least 40 nucleotides, or most preferably at least 50 nucleotides), or at least 25% (more preferably at least 50%, or at least 60%, or at least 70%, and most preferably at least 80%) of the length of the nucleic acid of the present invention to which it hybridizes, and has at least 60% sequence identity (more preferably at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, and most preferably at least 99.5%) with the nucleic acid of the present invention to which it hybridizes, where sequence identity is determined by comparing the sequences of the hybridizing nucleic acids when aligned so as to maximize overlap and identity while minimizing sequence gaps as described in more detail above.

Variants of the antigen binding proteins described herein can be prepared by site-specific mutagenesis of nucleotides in the DNA encoding the polypeptide, using cassette or PCR mutagenesis or other techniques well known in the art, to produce DNA encoding the variant, and thereafter expressing the recombinant DNA in cell culture as outlined herein. However, antigen binding proteins comprising variant CDRs having up to about 100-150 residues may be prepared by in vitro synthesis using established techniques. The variants typically exhibit the same qualitative biological activity as the naturally occurring analogue, e.g., binding to antigen. Such variants include, for example, deletions and/or insertions and/or substitutions of residues within the amino acid sequences of the antigen binding proteins. Any combination of deletion, insertion, and substitution is made to arrive at the final construct, provided that the final construct possesses the desired characteristics. The amino acid changes also may alter post-translational processes of the antigen binding protein, such as changing the number or position of glycosylation sites. In certain embodiments, antigen binding protein variants are prepared with the intent to modify those amino acid residues which are directly involved in epitope binding. In other embodiments, modification of residues which are not directly involved in epitope binding or residues not involved in epitope binding in any way, is desirable, for purposes discussed herein. Mutagenesis within any of the CDR regions and/or framework regions is contemplated. Covariance analysis techniques can be employed by the skilled artisan to design useful modifications in the amino acid sequence of the antigen binding protein. See, e.g., Choulier, et al., Proteins 41:475-484, 2000; Demarest et al., J. Mol. Biol. 335:41-48, 2004; Hugo et al., Protein Engineering 16 (5): 381-86, 2003; Aurora et al., US Patent Publication No. 2008/0318207 A1; Glaser et al., US Patent Publication No. 2009/0048122 A1; Urech et al., WO 2008/110348 A1; Borras et al., WO 2009/000099 A2. Such modifications determined by covariance analysis can improve potency, pharmacokinetic, pharmacodynamic, and/or manufacturability characteristics of an antigen binding protein.

The present invention also includes vectors comprising one or more nucleic acids encoding one or more components of the bispecific antigen binding proteins of the invention (e.g. variable regions, light chains, heavy chains, modified heavy chains, and Fd fragments). The term "vector" refers to any molecule or entity (e.g., nucleic acid, plasmid, bacteriophage or virus) used to transfer protein coding information into a host cell. Examples of vectors include, but are not limited to, plasmids, viral vectors, non-episomal mammalian vectors and expression vectors, for example, recombinant expression vectors. The term "expression vector" or "expression construct" as used herein refers to a recombinant DNA molecule containing a desired coding sequence and appropriate nucleic acid control sequences necessary for the expression of the operably linked coding sequence in a particular host cell. An expression vector can include, but is not limited to, sequences that affect or control transcription, translation, and, if introns are present, affect RNA splicing of a coding region operably linked thereto. Nucleic acid sequences necessary for expression in prokaryotes include a promoter, optionally an operator sequence, a ribosome binding site and possibly other sequences. Eukaryotic cells are known to utilize promoters, enhancers, and termination and polyadenylation signals. A secretory signal peptide sequence can also, optionally, be encoded by the expression vector, operably linked to the coding sequence of interest, so that the expressed polypeptide can be secreted by the recombinant host cell, for more facile isolation of the polypeptide of interest from the cell, if desired. For instance, in some embodiments, signal peptide sequences may be appended/fused to the amino terminus of any of the polypeptides sequences listed in Tables 6A, 6B, 7A, 7B, 9 and 10. In certain embodiments, a signal peptide having the amino acid sequence of MDMRVPAQLLGLLLLWLRGARC (SEQ ID NO: 32) is fused to the amino terminus of any of the polypeptide sequences in Tables 6A, 6B, 7A, 7B, 9 and 10. In other embodiments, a signal peptide having the amino acid sequence of MAWALLLLTLLTQGTGSWA (SEQ ID NO: 33) is fused to the amino terminus of any of the polypeptide sequences in Tables 6A, 6B, 7A, 7B, 9 and 10. In still other embodiments, a signal peptide having the amino acid sequence of MTCSPLLLTLLIHCTGSWA (SEQ ID NO: 34) is fused to the amino terminus of any of the polypeptide sequences in Tables 6A, 6B, 7A, 7B, 9 and 10. Other suitable signal peptide sequences that can be fused to the amino terminus of the polypeptide sequences described herein include: MEAPAQLLFLLLLWLPDTTG (SEQ ID NO: 35), MEWTWRVLFLVAAATGAHS (SEQ ID NO: 36), METPAQLLFLLLLWLPDTTG (SEQ ID NO: 37), METPAQLLFLLLLWLPDTTG (SEQ ID NO: 38), MKHLWFFLLLVAAPRWVLS (SEQ ID NO: 39), and MEWSWVFLFFLSVTTGVHS (SEQ ID NO: 40). Other signal peptides are known to those of skill in the art and may be fused to any of the polypeptide chains listed in Tables 6A, 6B, 7A, 7B, 9 and 10, for example, to facilitate or optimize expression in particular host cells.

Typically, expression vectors used in the host cells to produce the bispecific antigen proteins of the invention will contain sequences for plasmid maintenance and for cloning and expression of exogenous nucleotide sequences encoding the components of the bispecific antigen binding proteins. Such sequences, collectively referred to as "flanking sequences," in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag"-encoding sequence, i.e., an oligonucleotide molecule located at the 5' or 3' end of the polypeptide coding sequence; the oligonucleotide tag sequence encodes polyHis (such as hexaHis), FLAG, HA (hemaglutinin influenza virus), myc, or another "tag" molecule for which commercially available antibodies exist. This tag is typically fused to the polypeptide upon expression of the polypeptide, and can serve as a means for affinity purification or detection of the polypeptide from the host cell. Affinity purification can be accomplished, for example, by column chromatography using antibodies against the tag as an affinity matrix. Optionally, the tag can subsequently be removed from the purified polypeptide by various means such as using certain peptidases for cleavage.

Flanking sequences may be homologous (i.e., from the same species and/or strain as the host cell), heterologous (i.e., from a species other than the host cell species or strain), hybrid (i.e., a combination of flanking sequences from more than one source), synthetic or native. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the vectors of this invention may be obtained by any of several methods well known in the art. Typically, flanking sequences useful herein will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using routine methods for nucleic acid synthesis or cloning.

Whether all or only a portion of the flanking sequence is known, it may be obtained using polymerase chain reaction (PCR) and/or by screening a genomic library with a suitable probe such as an oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, CA), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. If the vector of choice does not contain an origin of replication site, one may be chemically synthesized based on a known sequence, and ligated into the vector. For example, the origin of replication from the plasmid pBR322 (New England Biolabs, Beverly, MA) is suitable for most gram-negative bacteria, and various viral origins (e.g., SV40, polyoma, adenovirus, vesicular stomatitus virus (VSV), or papillomaviruses such as HPV or BPV) are useful for cloning vectors in mammalian cells. Generally, the origin of replication component is not needed for mammalian expression vectors (for example, the SV40 origin is often used only because it also contains the virus early promoter).

A transcription termination sequence is typically located 3' to the end of a polypeptide coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using known methods for nucleic acid synthesis.

A selectable marker gene encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex or defined media. Specific selectable markers are the kanamycin resistance gene, the ampicillin resistance gene, and the tetracycline resistance gene. Advantageously, a neomycin resistance gene may also be used for selection in both prokaryotic and eukaryotic host cells.

Other selectable genes may be used to amplify the gene that will be expressed. Amplification is the process wherein genes that are required for production of a protein critical for growth or cell survival are reiterated in tandem within the chromosomes of successive generations of recombinant cells. Examples of suitable selectable markers for mammalian cells include dihydrofolate reductase (DHFR) and promoterless thymidine kinase genes. Mammalian cell transformants are placed under selection pressure wherein only the transformants are uniquely adapted to survive by virtue of the selectable gene present in the vector. Selection pressure is imposed by culturing the transformed cells under conditions in which the concentration of selection agent in the medium is successively increased, thereby leading to the amplification of both the selectable gene and the DNA that encodes another gene, such as one or more components of the bispecific antigen binding proteins described herein. As a result, increased quantities of a polypeptide are synthesized from the amplified DNA.

A ribosome-binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the polypeptide to be expressed. In certain embodiments, one or more coding regions may be operably linked to an internal ribosome binding site (IRES), allowing translation of two open reading frames from a single RNA transcript.

In some cases, such as where glycosylation is desired in a eukaryotic host cell expression system, one may manipulate the various pre- or prosequences to improve glycosylation or yield. For example, one may alter the peptidase cleavage site of a particular signal peptide, or add prosequences, which also may affect glycosylation. The final protein product may have, in the −1 position (relative to the first amino acid of the mature protein) one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated form of the desired polypeptide, if the enzyme cuts at such area within the mature polypeptide.

Expression and cloning vectors of the invention will typically contain a promoter that is recognized by the host organism and operably linked to the molecule encoding the polypeptide. The term "operably linked" as used herein refers to the linkage of two or more nucleic acid sequences in such a manner that a nucleic acid molecule capable of directing the transcription of a given gene and/or the synthesis of a desired protein molecule is produced. For example, a control sequence in a vector that is "operably linked" to a protein coding sequence is ligated thereto so that expression of the protein coding sequence is achieved under conditions compatible with the transcriptional activity of the control sequences. More specifically, a promoter and/or enhancer sequence, including any combination of cis-acting transcriptional control elements is operably linked to a coding sequence if it stimulates or modulates the transcription of the coding sequence in an appropriate host cell or other expression system.

Promoters are untranscribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, uniformly transcribe a gene to which they are operably linked, that is, with little or no control over gene expression. A large number of promoters, recognized by a variety of potential host cells, are well known. A suitable promoter is operably linked to the DNA encoding e.g., heavy chain, light chain, modified heavy chain, or other component of the bispecific antigen binding proteins of the invention, by removing the promoter from the source DNA by restriction enzyme digestion and inserting the desired promoter sequence into the vector.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

Additional promoters which may be of interest include, but are not limited to: SV40 early promoter (Benoist and Chambon, 1981, Nature 290:304-310); CMV promoter (Thornsen et al., 1984, Proc. Natl. Acad. U.S.A. 81:659-663); the promoter contained in the 3' long terminal repeat of Rous sarcoma virus (Yamamoto et al., 1980, Cell 22:787-797); herpes thymidine kinase promoter (Wagner et al., 1981, Proc. Natl. Acad. Sci. U.S.A. 78:1444-1445); promoter and regulatory sequences from the metallothionine gene Prinster et al., 1982, Nature 296:39-42); and prokaryotic promoters such as the beta-lactamase promoter (Villa-Kamaroff et al., 1978, Proc. Natl. Acad. Sci. U.S.A. 75:3727-3731); or the tac promoter (DeBoer et al., 1983, Proc. Natl. Acad. Sci. U.S.A. 80:21-25). Also of interest are the following animal transcriptional control regions, which exhibit tissue specificity and have been utilized in transgenic animals: the elastase I gene control region that is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); the insulin gene control region that is active in pancreatic beta cells (Hanahan, 1985, Nature 315:115-122); the immunoglobulin gene control region that is active in lymphoid cells (Grosschedl et al., 1984, Cell 38:647-658; Adames et al., 1985, Nature 318:533-538; Alexander et al., 1987, Mol. Cell. Biol. 7:1436-1444); the mouse mammary tumor virus control region that is active in testicular, breast, lymphoid and mast cells (Leder et al., 1986, Cell 45:485-495); the albumin gene control region that is active in liver (Pinkert et al., 1987, Genes and Devel. 1:268-276); the alpha-feto-protein gene control region that is active in liver (Krumlauf et al., 1985, Mol. Cell. Biol. 5:1639-1648; Hammer et al., 1987, Science 253:53-58); the alpha 1-antitrypsin gene control region that is active in liver (Kelsey et al., 1987, Genes and Devel. 1:161-171); the beta-globin gene control region that is active in myeloid cells (Mogram et al, 1985, Nature 315:338-340; Kollias et al, 1986, Cell 46:89-94); the myelin basic protein gene control region that is active in oligodendrocyte cells in the brain (Readhead et al., 1987, Cell 48:703-712); the myosin light chain-2 gene control region that is active in skeletal muscle (Sani, 1985, Nature 314:283-286); and the gonadotropic releasing hormone gene control region that is active in the hypothalamus (Mason et al., 1986, Science 234:1372-1378).

An enhancer sequence may be inserted into the vector to increase transcription of DNA encoding a component of the bispecific antigen binding proteins (e.g., light chain, heavy chain, modified heavy chain, Fd fragment) by higher eukaryotes. Enhancers are cis-acting elements of DNA, usually about 10-300 bp in length, that act on the promoter to increase transcription. Enhancers are relatively orientation and position independent, having been found at positions both 5' and 3' to the transcription unit. Several enhancer sequences available from mammalian genes are known (e.g., globin, elastase, albumin, alpha-feto-protein and insulin). Typically, however, an enhancer from a virus is used. The SV40 enhancer, the cytomegalovirus early promoter enhancer, the polyoma enhancer, and adenovirus enhancers known in the art are exemplary enhancing elements for the activation of eukaryotic promoters. While an enhancer may be positioned in the vector either 5' or 3' to a coding sequence, it is typically located at a site 5' from the promoter. A sequence encoding an appropriate native or heterologous signal sequence (leader sequence or signal peptide) can be incorporated into an expression vector, to promote extracellular secretion of the antibody. The choice of signal peptide or leader depends on the type of host cells in which the antibody is to be produced, and a heterologous signal sequence can replace the native signal sequence. Examples of signal peptides are described above. Other signal peptides that are functional in mammalian host cells include the signal sequence for interleukin-7 (IL-7) described in U.S. Pat. No. 4,965,195; the signal sequence for interleukin-2 receptor described in Cosman et al., 1984, Nature 312:768; the interleukin-4 receptor signal peptide described in EP Patent No. 0367 566; the type I interleukin-1 receptor signal peptide described in U.S. Pat. No. 4,968,607; the type II interleukin-1 receptor signal peptide described in EP Patent No. 0 460 846.

The expression vectors that are provided may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art. The expression vectors can be introduced into host cells to thereby produce proteins, including fusion proteins, encoded by nucleic acids as described herein.

In certain embodiments, nucleic acids encoding the different components of the bispecific antigen binding proteins of the invention may be inserted into the same expression vector. In such embodiments, the two nucleic acids may be separated by an internal ribosome entry site (IRES) and under the control of a single promoter such that the light chain and heavy chain are expressed from the same mRNA transcript. Alternatively, the two nucleic acids may be under the control of two separate promoters such that the light chain and heavy chain are expressed from two separate mRNA transcripts.

Similarly, for IgG-scFv bispecific antigen binding proteins, the nucleic acid encoding the light chain may be cloned into the same expression vector as the nucleic acid encoding the modified heavy chain (fusion protein comprising the heavy chain and scFv) where the two nucleic acids are under the control of a single promoter and separated by an IRES or where the two nucleic acids are under the control of two separate promoters. For IgG-Fab bispecific antigen binding proteins, nucleic acids encoding each of the three components may be cloned into the same expression vector. In some embodiments, the nucleic acid encoding the light chain of the IgG-Fab molecule and the nucleic acid encoding the second polypeptide (which comprises the other half of the C-terminal Fab domain) are cloned into one expression vector, whereas the nucleic acid encoding the modified heavy chain (fusion protein comprising a heavy chain and half of a Fab domain) is cloned into a second expression vector. In certain embodiments, all components of the bispecific antigen binding proteins described herein are expressed from the same host cell population. For example, even if one or more components is cloned into a separate expression vector, the host cell is co-transfected with both expression vectors such that one cell produces all components of the bispecific antigen binding proteins.

After the vector has been constructed and the one or more nucleic acid molecules encoding the components of the bispecific antigen binding proteins described herein has been inserted into the proper site(s) of the vector or vectors, the completed vector(s) may be inserted into a suitable host cell for amplification and/or polypeptide expression. Thus, the present invention encompasses an isolated host cell comprising one or more expression vectors encoding the components of the bispecific antigen binding proteins. The term "host cell" as used herein refers to a cell that has been transformed, or is capable of being transformed, with a nucleic acid and thereby expresses a gene of interest. The term includes the progeny of the parent cell, whether or not the progeny is identical in morphology or in genetic make-up to the original parent cell, so long as the gene of interest is present. A host cell that comprises an isolated nucleic acid of the invention, preferably operably linked to at least one expression control sequence (e.g. promoter or enhancer), is a "recombinant host cell."

The transformation of an expression vector for an antigen binding protein into a selected host cell may be accomplished by well-known methods including transfection, infection, calcium phosphate co-precipitation, electroporation, microinjection, lipofection, DEAE-dextran mediated transfection, or other known techniques. The method selected will in part be a function of the type of host cell to be used. These methods and other suitable methods are well known to the skilled artisan, and are set forth, for example, in Sambrook et al., 2001, supra.

A host cell, when cultured under appropriate conditions, synthesizes an antigen binding protein that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

Exemplary host cells include prokaryote, yeast, or higher eukaryote cells. Prokaryotic host cells include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacillus*, such as *B. subtilis* and *B. licheniformis*, *Pseudomonas*, and *Streptomyces*. Eukaryotic microbes such as filamentous fungi or yeast are suitable cloning or expression hosts for recombinant polypeptides. *Saccharomyces cerevisiae*, or common baker's yeast, is the most commonly used among lower eukaryotic host microorganisms. However, a number of other genera, species, and strains are commonly available and useful herein, such as *Pichia*, e.g. *P. pastoris, Schizosaccharomyces pombe; Kluyveromyces, Yarrowia; Candida; Trichoderma reesia, Neurospora crassa; Schwanniomyces*, such as *Schwanniomyces occidentalis*; and filamentous fungi, such as, e.g., *Neurospora, Penicillium, Tolypocladium*, and *Aspergillus* hosts such as *A. nidulans* and *A. niger*.

Host cells for the expression of glycosylated antigen binding proteins can be derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection of such cells are publicly available, e.g., the L-1 variant of *Autographa californica* NPV and the Bm-5 strain of *Bombyx mori* NPV.

Vertebrate host cells are also suitable hosts, and recombinant production of antigen binding proteins from such cells has become routine procedure. Mammalian cell lines available as hosts for expression are well known in the art and include, but are not limited to, immortalized cell lines available from the American Type Culture Collection (ATCC), including but not limited to Chinese hamster ovary (CHO) cells, including CHOK1 cells (ATCC CCL61), DXB-11, DG-44, and Chinese hamster ovary cells/-DHFR (CHO, Urlaub et al., Proc. Natl. Acad. Sci. USA 77:4216, 1980); monkey kidney CV1 line transformed by SV40 (COS-7, ATCC CRL 1651); human embryonic kidney line (293 or 293 cells subcloned for growth in suspension culture, (Graham et al., J. Gen Virol. 36:59, 1977); baby hamster kidney cells (BHK, ATCC CCL 10); mouse sertoli cells (TM4, Mather, Biol. Reprod. 23:243-251, 1980); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human hepatoma cells (Hep G2, HB 8065); mouse mammary tumor (MMT 060562, ATCC CCL51); TRI cells (Mather et al., Annals N. Y Acad. Sci. 383:44-68, 1982); MRC 5 cells or FS4 cells; mammalian myeloma cells, and a number of other cell lines. In another embodiment, a cell line from the B cell lineage that does not make its own antibody but has a capacity to make and secrete a heterologous antibody can be selected. CHO cells are preferred host cells in some embodiments for expressing the bispecific antigen binding proteins of the invention.

Host cells are transformed or transfected with the above-described nucleic acids or vectors for production of bispecific antigen binding proteins and are cultured in conventional nutrient media modified as appropriate for inducing promoters, selecting transformants, or amplifying the genes encoding the desired sequences. In addition, novel vectors and transfected cell lines with multiple copies of transcription units separated by a selective marker are particularly useful for the expression of antigen binding proteins. Thus, the present invention also provides a method for preparing a bispecific antigen binding protein described herein comprising culturing a host cell comprising one or more expression vectors described herein in a culture medium under conditions permitting expression of the bispecific antigen binding protein encoded by the one or more expression vectors; and recovering the bispecific antigen binding protein from the culture medium.

The host cells used to produce the antigen binding proteins of the invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44, 1979; Barnes et al., Anal. Biochem. 102:255, 1980; U.S. Pat. Nos. 4,767,704; 4,657,866; 4,927,762; 4,560,655; or 5,122,469; WO90103430; WO 87/00195; or U.S. Patent Re. No. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Upon culturing the host cells, the bispecific antigen binding protein can be produced intracellularly, in the periplasmic space, or directly secreted into the medium. If the antigen binding protein is produced intracellularly, as a first step, the particulate debris, either host cells or lysed fragments, is removed, for example, by centrifugation or ultrafiltration. The bispecifc antigen binding protein can be purified using, for example, hydroxyapatite chromatography, cation or anion exchange chromatography, or preferably affinity chromatography, using the antigen(s) of interest or protein A or protein G as an affinity ligand. Protein A can be used to purify proteins that include polypeptides that are based on human γ1, γ2, or γ4 heavy chains (Lindmark et al., J. Immunol. Meth. 62:1-13, 1983). Protein G is recommended for all mouse isotypes and for human γ3 (Guss et al., EMBO J. 5:15671575, 1986). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the protein comprises a CH3 domain, the Bakerbond ABX™ resin (J. T. Baker, Phillipsburg, N.J.) is useful for purification. Other techniques for protein purification such as ethanol precipitation, Reverse Phase HPLC, chromatofocusing, SDS-PAGE, and ammonium sulfate precipitation are also possible depending on the particular bispecific antigen binding protein to be recovered.

EXAMPLES

CHZ01

The ability to generate multispecific antigen binding proteins and half-life extended therapeutic proteins is paramount to advance many therapeutics candidates to clinic. Often, this implies extensive protein design with vary degrees of success. In either case, two different Fc portions come together and form a hetero-dimer. In order for this to happen, changes in the protein native sequence must occur. Traditionally, those changes have been focused in the CH3-CH3' interface of the Fc portion, where charge pairing mutations and knob in hole designs have been inserted.

Figure 2:
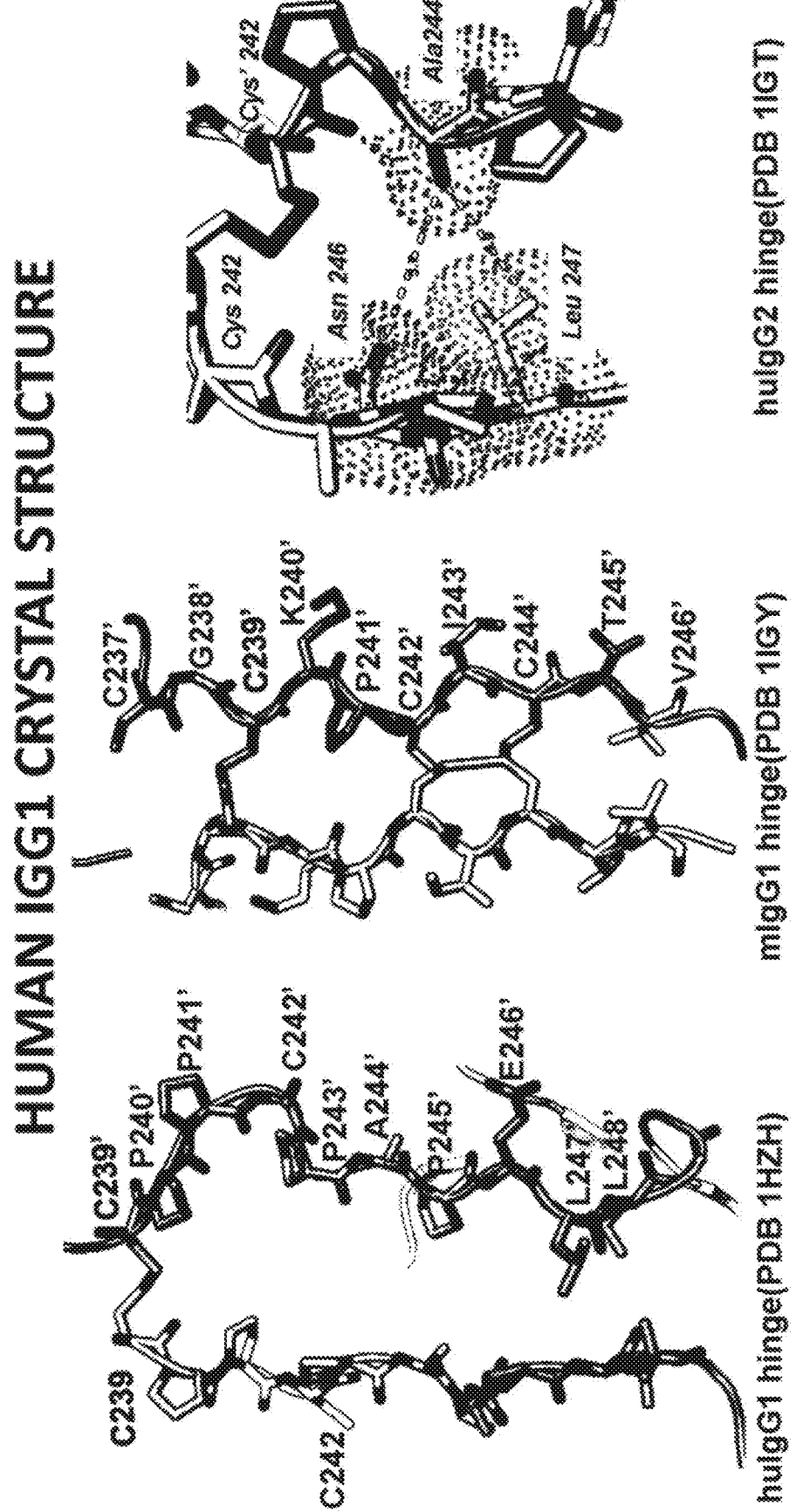
FIG. 2 depicts the human IgG1 crystal structure which does not show a second disulfide bond at the CPPC, although this could be an artifact introduced by the radiation damage during X-Ray data collection. Also, the IgG1 murine crystal structure (1IGY), as well 'in house' mass spec data, strongly suggests that the disulfide a C242 should be intact. Therefore, using the mIgG1 and huIgG2 structures as a guide results in a better understanding of the rotamers positions of the residues downstream the CPPC motif.
Figure 3:
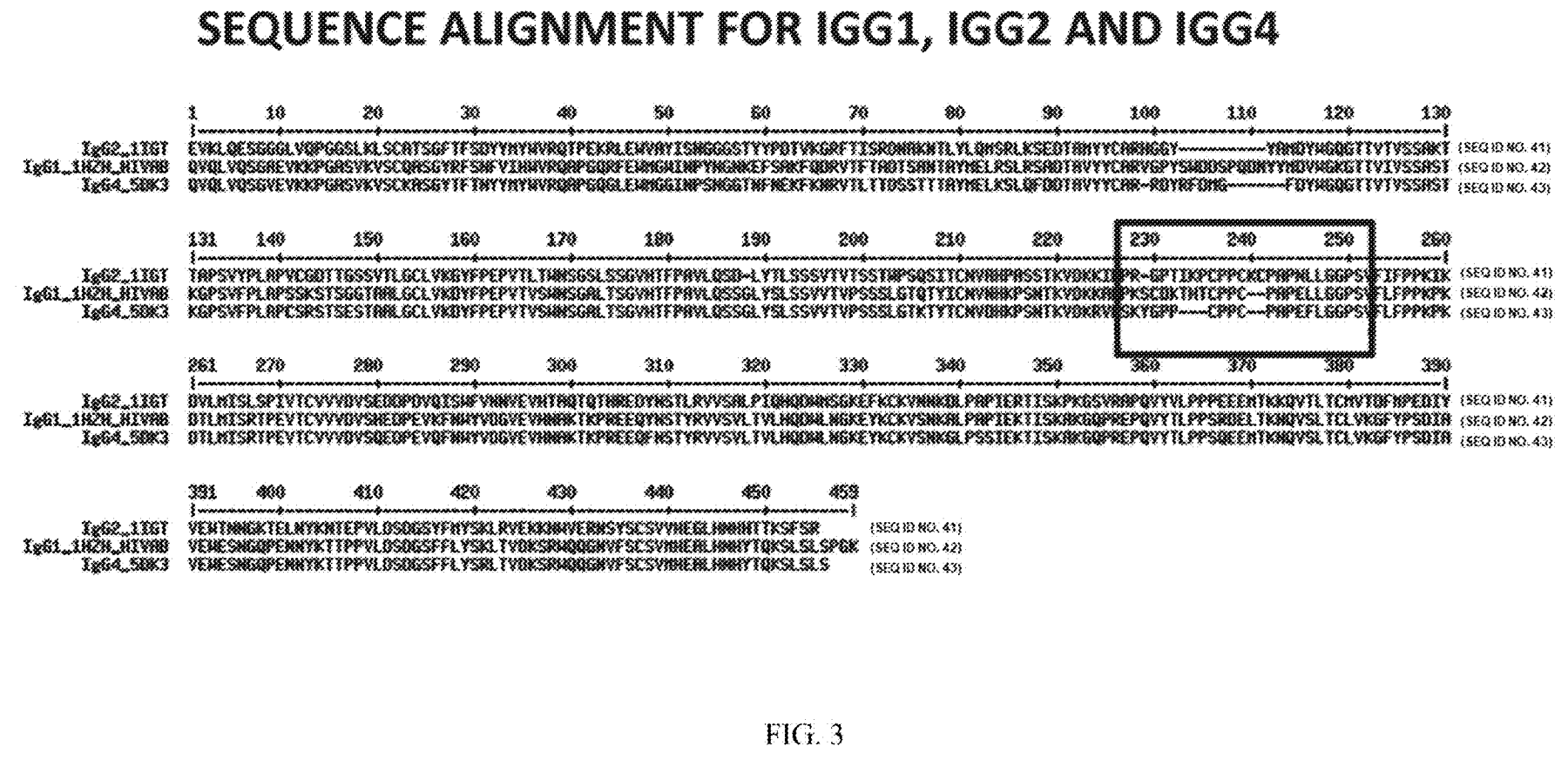

It is possible to see that the two heavy chains in a monoclonal antibody have two main points of contact: Fc-CH3 and the hinge (FIG. 1). The hinge region connects the Fc to two Fab domains and subsequently, it must display a flexible structure that allows for free rotation of the Fabs, necessary for these warheads to adopt the correct angle of approach to engage their targets while the Fc region may interact with its multiple binding partners like FcγR, FcRn and C1q. Despite the flexibility around the hinge region, this interface is mediated by a strong and structurally rigid motif, the "CPPC' motif (FIG. 1-3). Here, the proline residues introduce a very specific and stable secondary structure that allows for the -SH side-chains of cysteine residues to meet their counterparts and form disulfide bonds. Moreover, this same rigid frame is likely to be extended upstream and downstream the CPP" motif, suggesting that the side chains of those residues in the vicinity of this motif are also likely to present a stable conformation.

Figure 4:
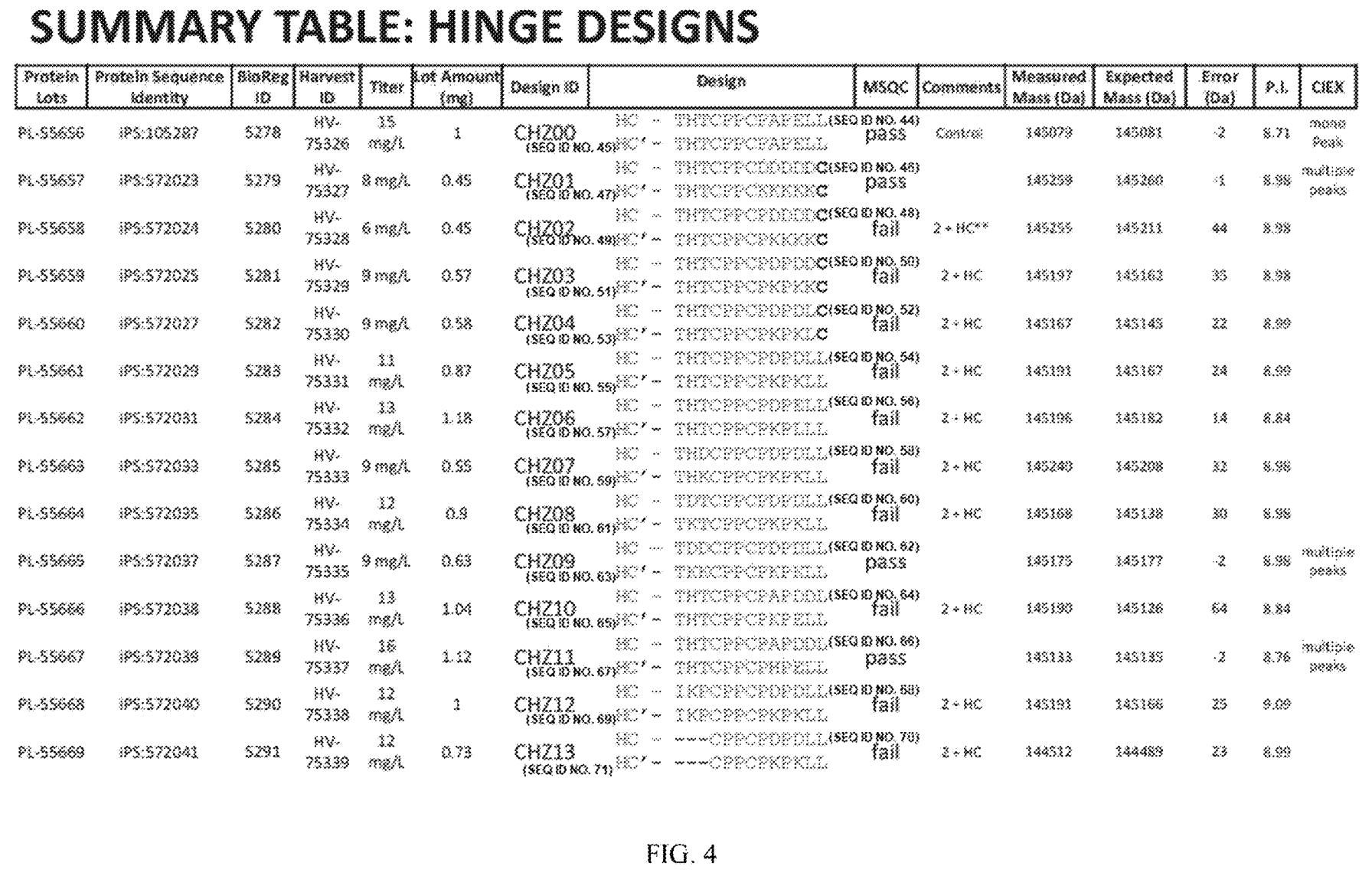

The only crystal structure of a human full-length IgG1 antibody available in the Protein Data Bank ("PDB") (PDB 1HZH) shows only a partially intact CPPC motif where the second cysteine (C242) is not forming a disulfide bond, with each side chain at position 242 in the two polypeptides chains pointing in opposite directions (FIG. 2). Although there is structural information for the mouse IgG1 antibody showing an intact structure for CPPC motif, the sequence variation between these two species (FIG. 3) did not allow an exact prediction of the spatial placement of the side chains of those residues downstream the Cys 242 in the human IgG1. Consequently, and keeping the native sequence of CPPC motif, a string of opposite charged residues named 'Charged Zipper Hinge 01' (CZH01) was inserted downstream of that same region (FIG. 4). It is believed that this 'Charged Zipper' would both attract heavy chains with opposite charge and repel chains with the same charge.

Figure 5:
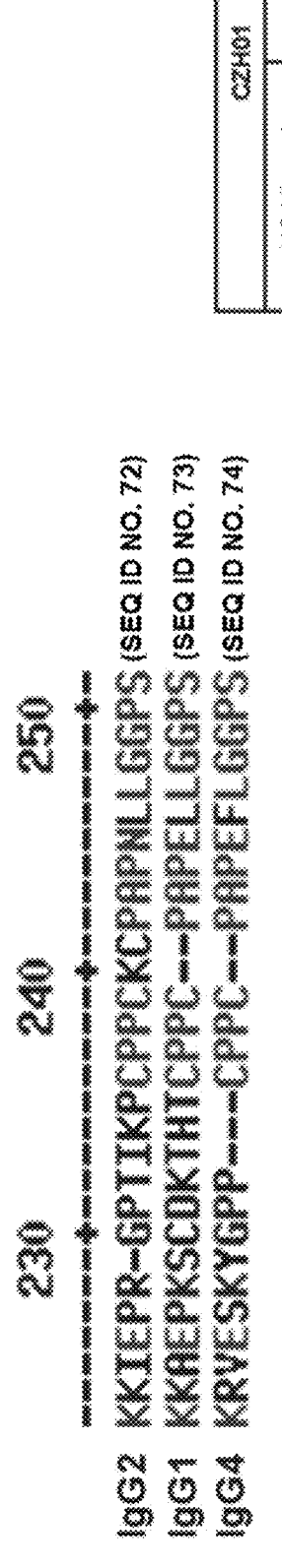
FIG. 5 depicts the charged zipper Hinge-Design CZH01. The C239 is the only C making a disulfide bridge within the IgG1 hinge (Saphire & Wilson, Science, 2001 (anti HIV-1 B12 antibody) according to the crystal structure. However, other data suggests that the second Cys (C242) can still form a disulfide bond and also that P241 seems to be important for that same bond to happen. The rational is then to design a CPM string downstream from this second disulfide (see mutations in orange line) followed by inserting a new disulfide at L248C (in orange dotted line). The SEQ ID NOs. are as follows: CZH01 IGG2 HINGE (SEQ ID NO: 72), CZH01 IGG1 HINGE (SEQ ID NO: 73), and CZH01 IGG4 HINGE (SEQ ID NO: 74).
Figure 5:
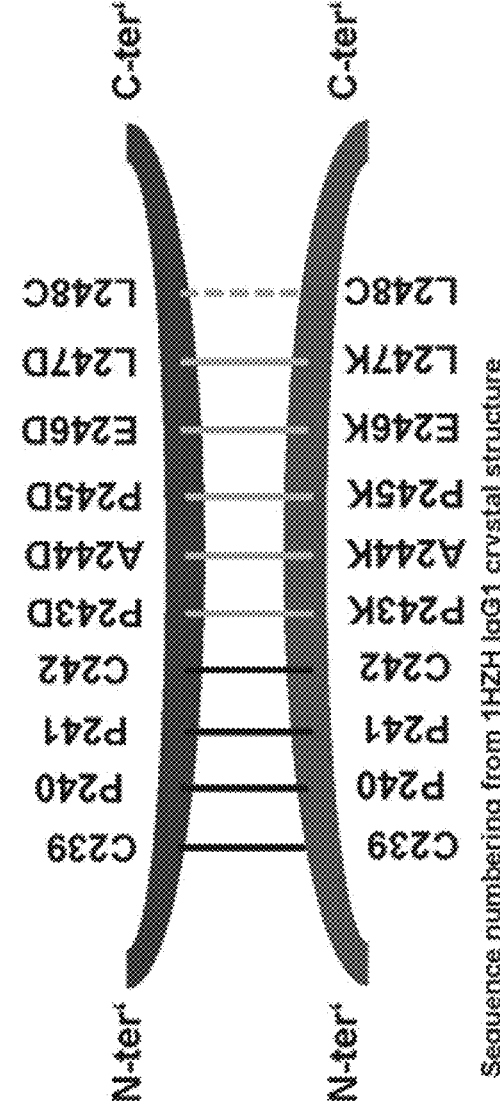
Figure 6:
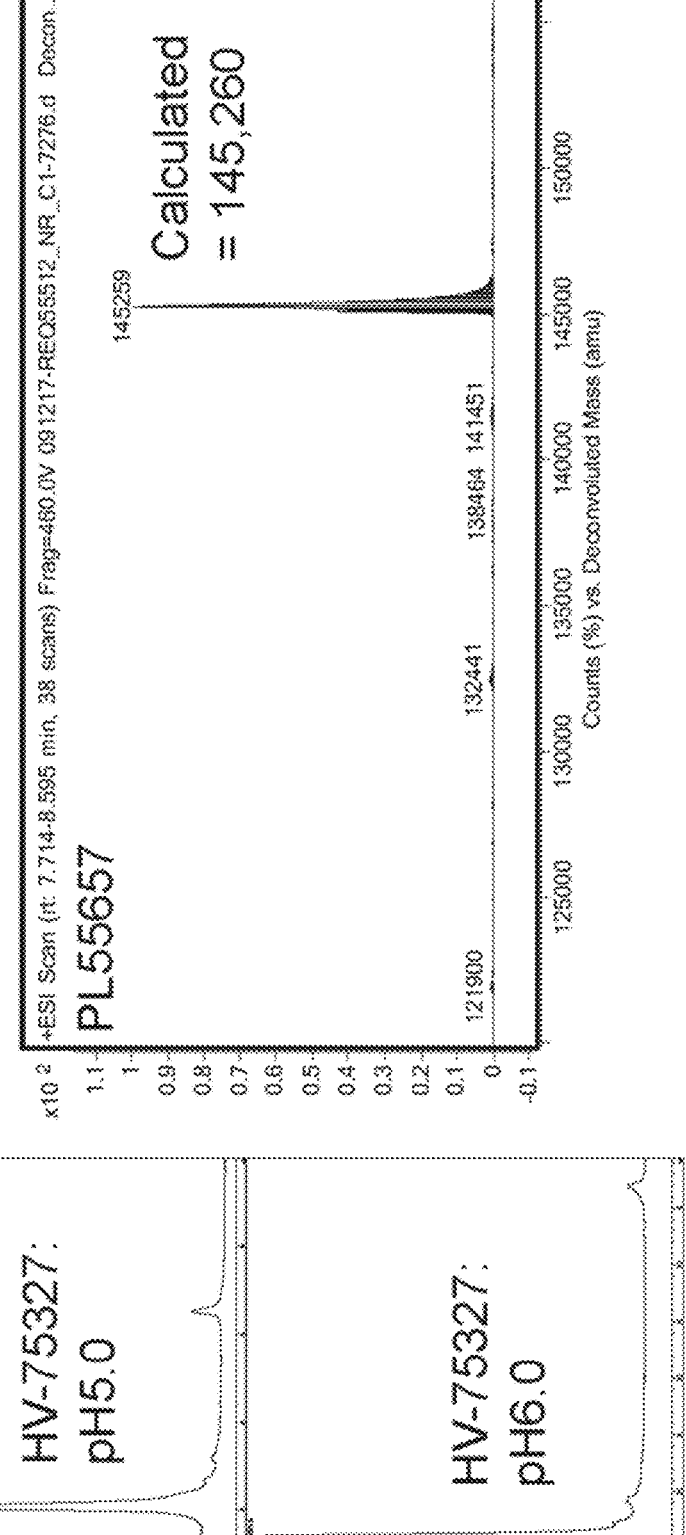
FIG. 6 depicts Analytical CEX and Mass Spec-CZH01.

To test this hypothesis, these mutations were inserted into antibody X and transiently expressed in HEK293 cells, followed by a single step protein purification (protein A followed by CEX). To verify whether the newly generated antibodies were comprised of two distinct heavy chains (negatively and positively charged, respectively), extensive reduced and non-reduced mass spec assays were performed. Indeed, the results showed that this strategy was successfully driving the heavy chain pairing without any additional mutations in the Fc-CH3 region (FIG. 4-6). It is most likely that the string of lysines (243 to 247) are facing and interacting with the string of aspartic acids (243 to 247).

CHZ11

Figure 9:
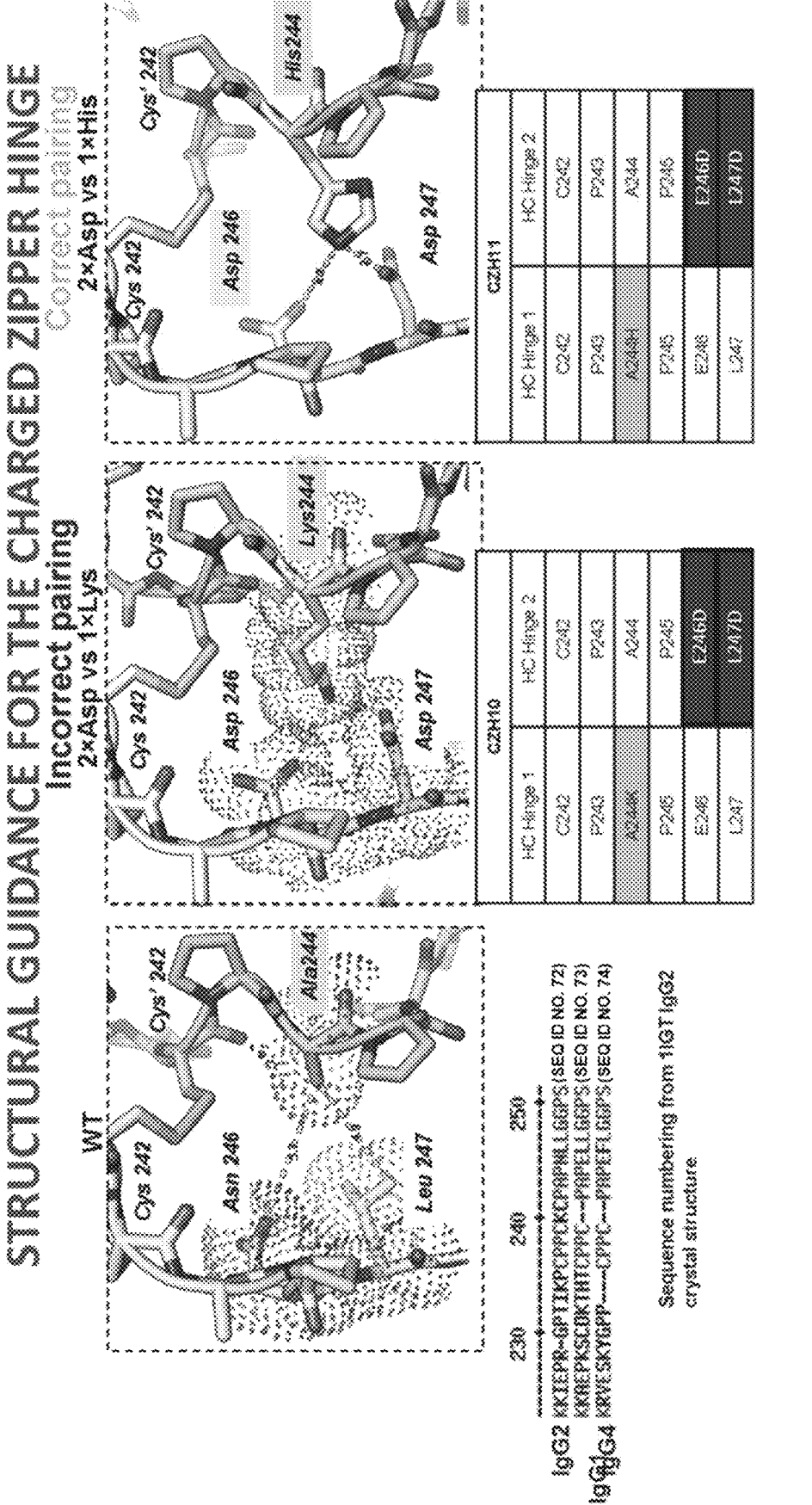
FIG. 9 depicts structural guidance for the charged zipper hinge in IgG2 (SEQ ID NO: 72), IgG1 (SEQ ID NO: 73), and IgG4 (SEQ ID NO: 74).
Figure 10:
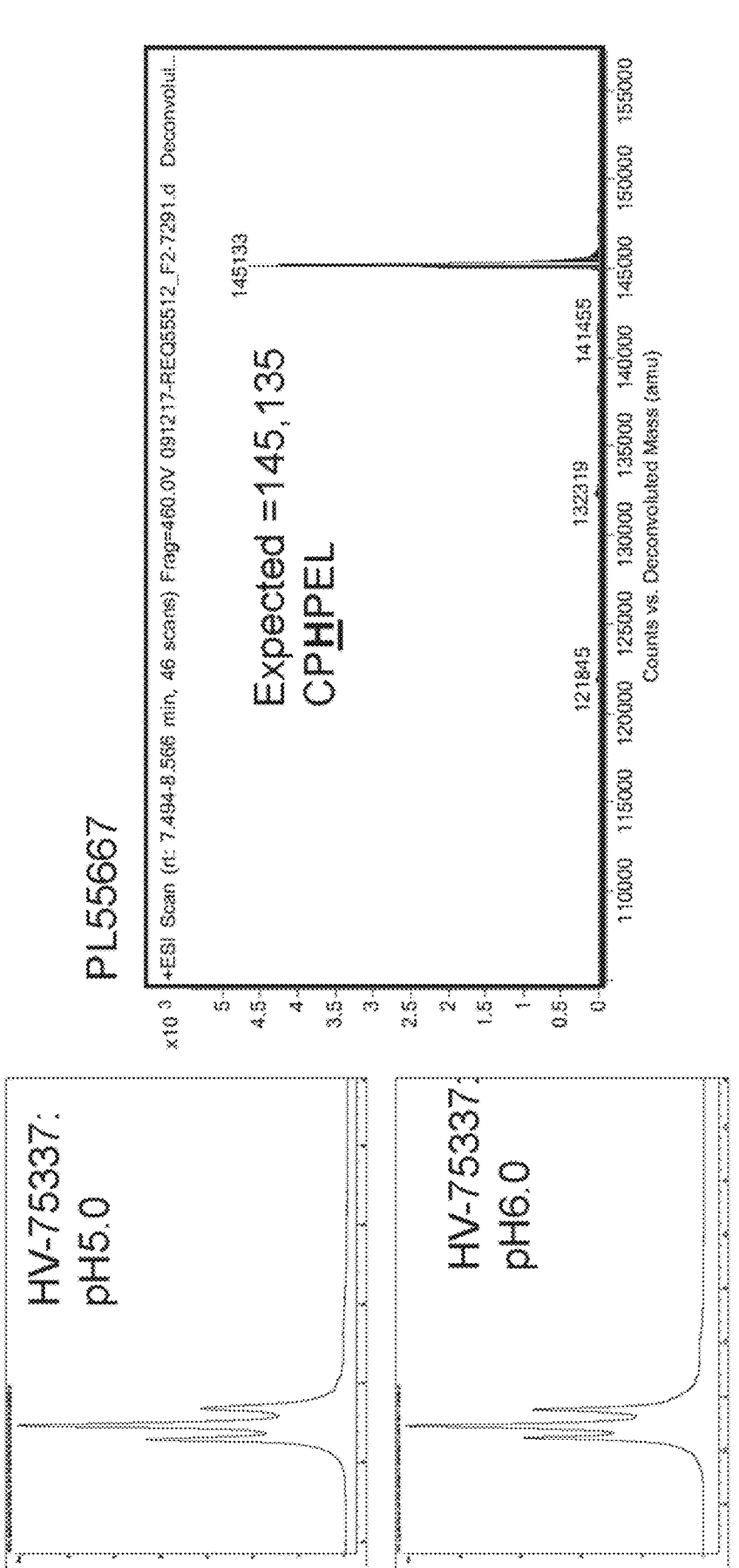
FIG. 10 depicts Analytical CEX and Mass Spec-CZH11.

Furthermore, the structural analysis of mouse IgG2 molecule shows that residues 246 and 247 in one chain and residue 244 in the counterpart chain, have their side-chains pointing at each other (FIG. 9). These residues are downstream of Cys242 and in close proximity to the CPPC motif suggesting a conformational stability. Moreover, the charge residues have side-chains that could fit within the structural spatial arrangement and thus not disrupt the CPPC interface. Asn246 and Leu247 were both replaced with negatively charged aspartic acid residues. To pair with these two residues, a single histidine replaced Ala244 in the opposite chain in such a way that it could either make productive contacts with the opposite charged residues (Asp246 and Asp247) or showing a repelling effect (FIGS. 9 and 10)

(CZH11). To test the rational design this variant was expressed and purified. Surprisingly, it was confirmed by mass spec that, indeed, these three residues forming a triad and were sufficient to drive the hinge dimerization (FIG. 10). CHZ09

Figure 7:
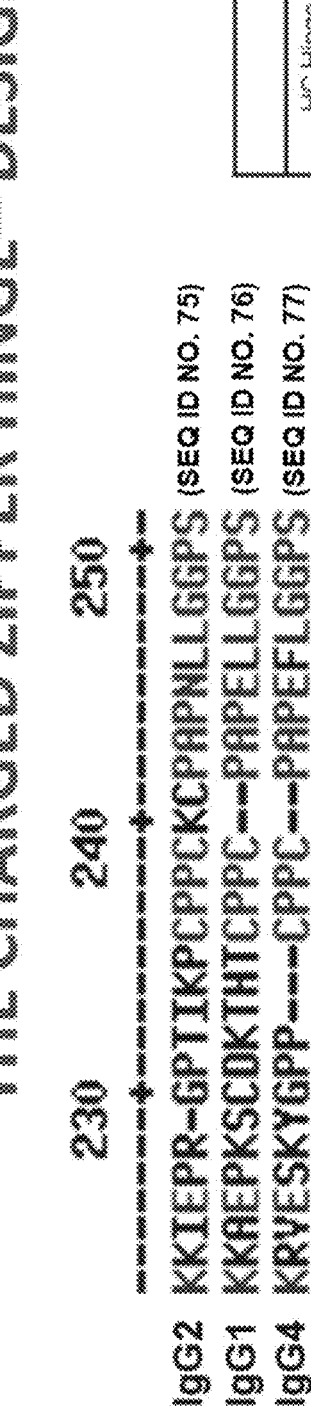
FIG. 7 depicts the charged zipper Hinge-Design CZH09. The SEQ ID NOs. are as follows: CZH09 IGG2 HINGE (SEQ ID NO: 75), CZH09 IGG1 HINGE (SEQ ID NO: 76), and CZH09 IGG4 HINGE (SEQ ID NO: 77).
Figure 7:
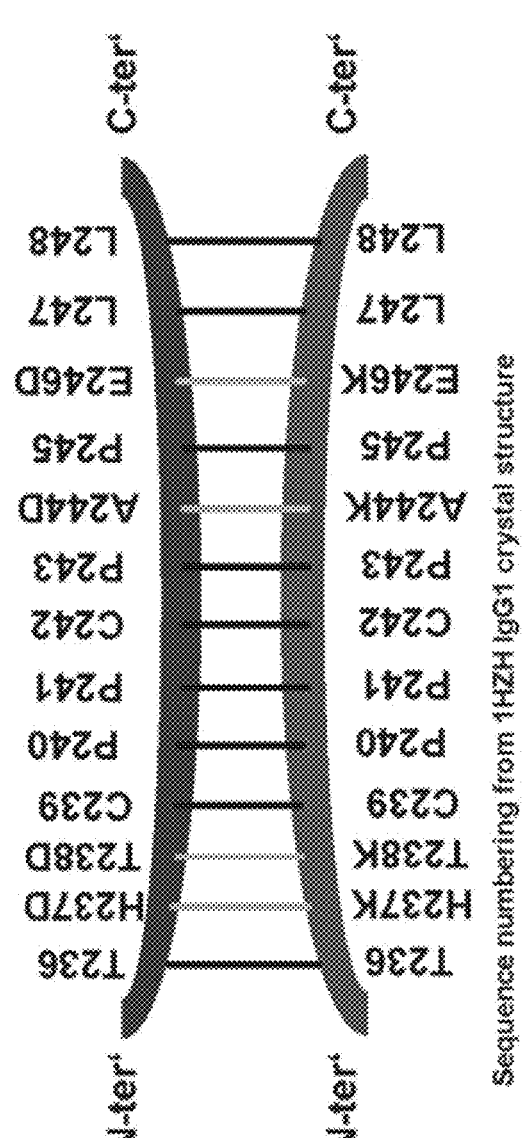
Figure 8:
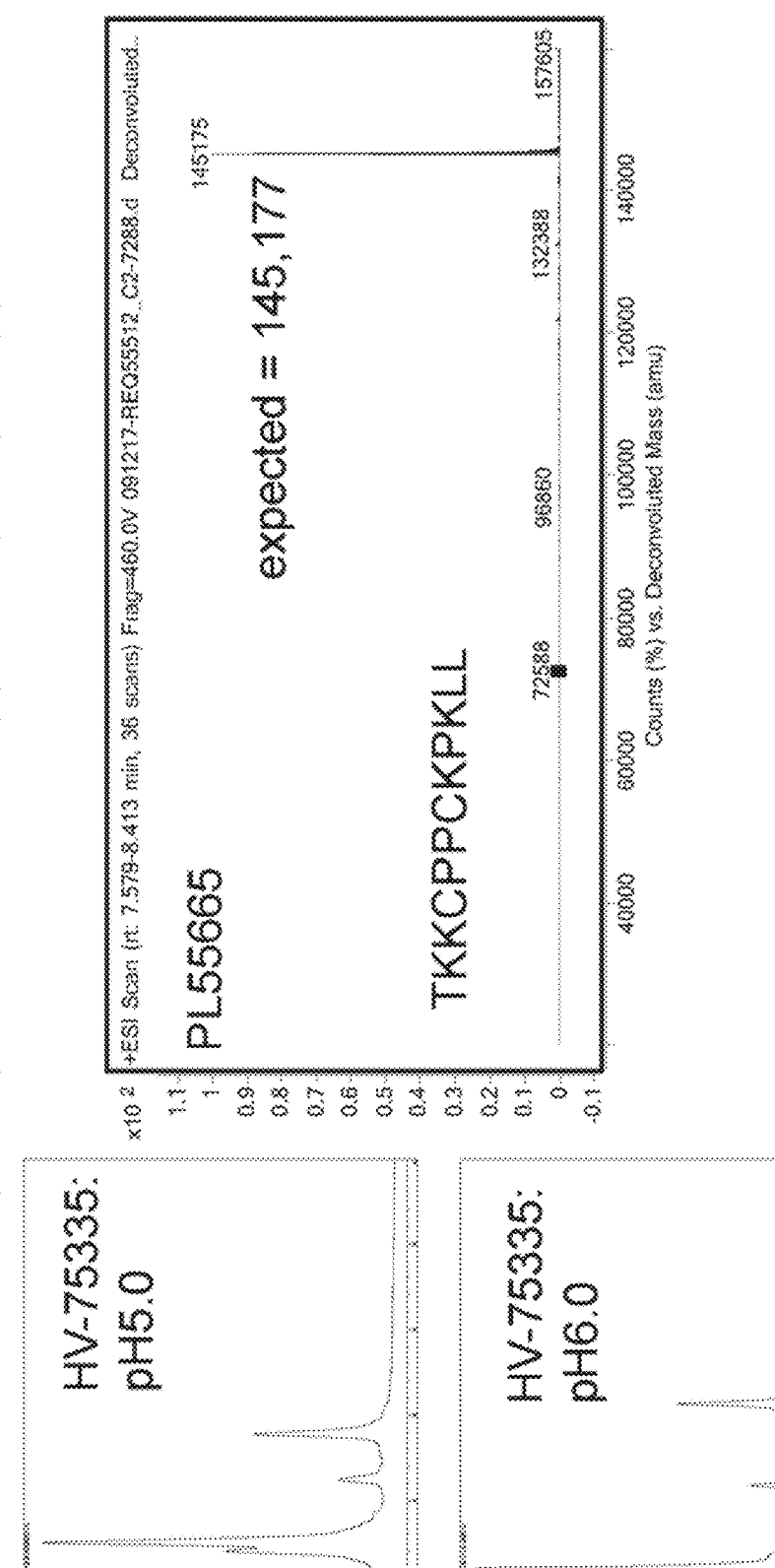
FIG. 8 depicts Analytical CEX and Mass Spec-CZH09.

Next, the upstream region of the CPPC region was tested to verify whether the engineering of this sequence could also drive the heavy chain dimerization. While keeping two charged pair mutations Ala244Lys/Asp and Glu246Lys/Asp, downstream of the Cys242 residue, two extra charged pair mutations were inserted His237Lys/Asp and Thr246Lys/Asp upstream of the Cys239 residue (CZH09) (FIG. 7). The data shows that CPMs inserted upstream of the CPPC motif are also capable of driving Heavy chain dimerization.

CH3 CPMs

Figure 12:
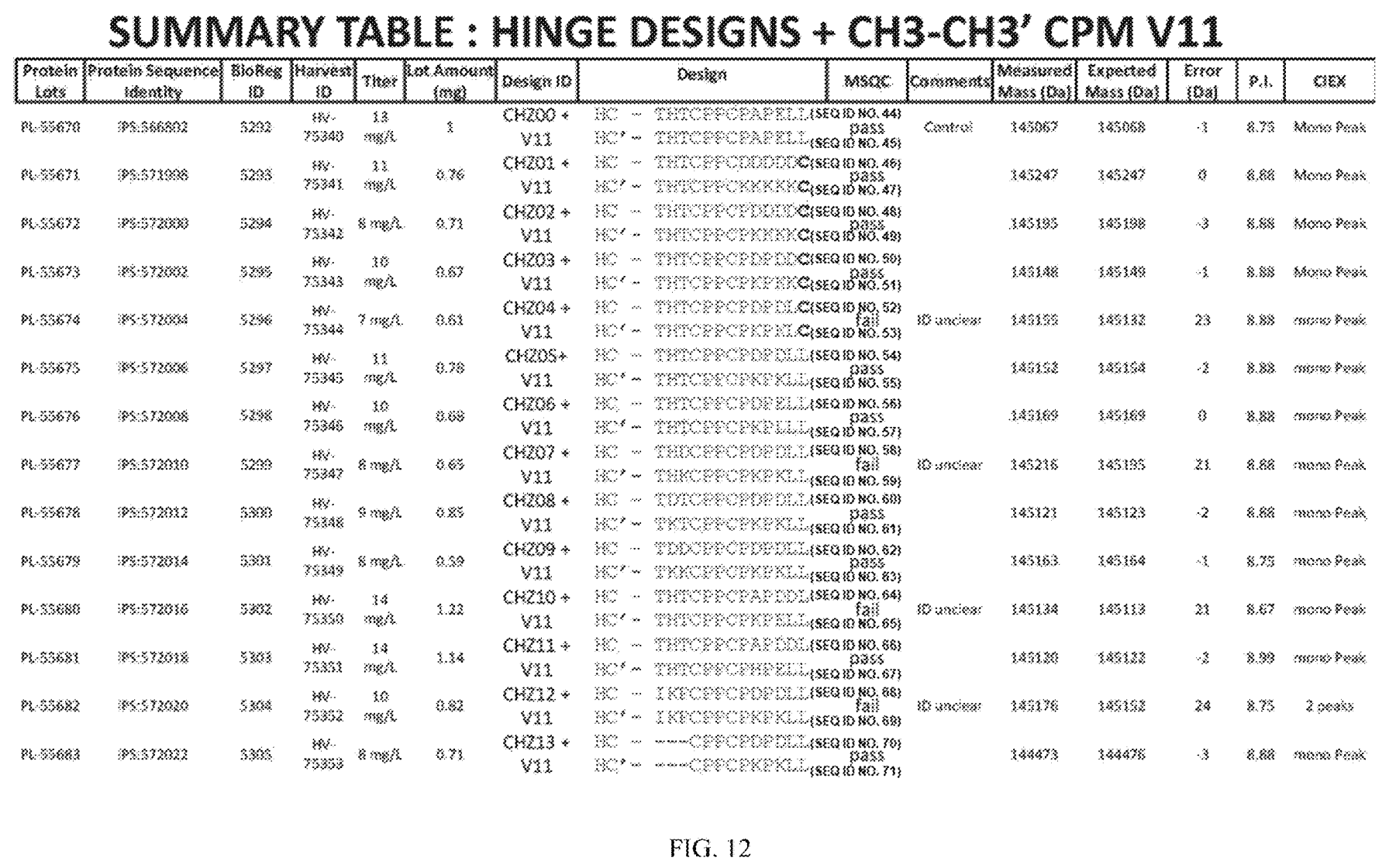

In addition, CPMs (charge pair mutations) inserted in the hinge region are compatible with CPMs previously inserted in the Fc-CH3 regions. So-called 'v11' CH3 CPMs (D399K in one CH3 region and K409D/K392D in the other CH3 region) were added to molecules containing CZH01, CZH09 and CZH11 mutations (FIGS. 11 and 12). The results showed that all the three CPMs inserted in the hinge region, CZH01, CZH09 and CZH11, could also successfully drive the heavy chain pairing in presence of Fc-CH3 CPMs.

In order to access the impact of these new mutations engineered in the hinge region stability assays were run looking at the thermostability values of these new variants in comparison with the wild-type molecule. The data shows that the Tm data for CZH01, CZH09 and CZH11 compare very well with the control CHZ00 in the absence of CH3-CPM v11 (73.3° C.) and with CHZ00 in presence of CH3-CPM v11 (70.7° C.) (Table 1).

TABLE 1

| Molecule | Hinge Mutation | +CH3 CPM v11 | Tm1 (° C.) | Tagg (° C.) |
|---|---|---|---|---|
| Standard IgG Antibody | CHZ00 (WT) | N | 73.3 | 68.9 |
| Standard IgG Antibody | CHZ01 | N | 73.4 | 73.8 |
| Standard IgG Antibody | CHZ09 | N | 73.7 | 75.5 |
| Standard IgG Antibody | CHZ11 | N | 73.2 | 74.4 |
| Standard IgG Antibody | CHZ00 (WT) | Y | 70.7 | 73.6 |
| Standard IgG Antibody | CHZ01 | Y | 71.9 | 74.2 |
| Standard IgG Antibody | CHZ09 | Y | 69.8 | 74.3 |
| Standard IgG Antibody | CHZ11 | Y | 69.6 | 73.6 |

We claim:

1. An isolated heteromultimer comprising a heterodimeric immunoglobulin hinge domain comprising a first immunoglobulin hinge domain polypeptide and a second immunoglobulin hinge domain polypeptide, wherein:
(i) the first immunoglobulin hinge domain polypeptide comprises the following amino acid substitutions: P243K, A244K, P245K, N/E246K, and L247K; and
(ii) the second immunoglobulin hinge domain polypeptide comprises the following amino acid substitutions: P243D, A244D, P245D, N/E246D, and L247D;
wherein the numbering of amino acid residues is according to Kabat.

2. The isolated heteromultimer according to claim 1, wherein each hinge domain polypeptide further comprises an L248C substitution according to Kabat.

3. The isolated heteromultimer according to claim 1, wherein the immunoglobulin hinge region is an IgG1 hinge region.

4. The isolated heteromultimer according to claim 1, wherein the heteromultimer is a bispecific or multispecific antibody.

5. The isolated heteromultimer according to claim 1, wherein each immunoglobulin hinge domain polypeptide further comprises a CH3 domain.

6. The isolated heteromultimer according to claim 5, wherein one CH3 domain comprises a F405L, F405A, F405D, F405E, F405H, F405I, F405K, F405M, F405N, F405Q, F405S, F405T, F405V, F405W, or F405Y mutation; and the other CH3 domain comprises a K409R mutation; wherein the numbering of amino acid residues is according to Kabat.

7. The isolated heteromultimer according to claim 5, wherein one CH3 domain comprises a T366W mutation; and the other CH3 domain comprises T366S, L368A, Y407V mutations; wherein the numbering of amino acid residues is according to Kabat.

8. The isolated heteromultimer according to claim 5, wherein one CH3 domain comprises K/R409D and K392D mutations; and the other CH3 domain comprises D399K and E356K mutations; wherein the numbering of amino acid residues is according to Kabat.

9. The isolated heteromultimer according to claim 5, wherein one CH3 domain comprises Y349C and T366W mutations; and the other CH3 domain comprises E356C, T366S, L368A, and Y407V mutations; wherein the numbering of amino acid residues is according to Kabat.

10. The isolated heteromultimer according to claim 5, wherein one CH3 domain comprises Y349C and T366W mutations; and the other CH3 domain comprises S354C, T366S, L368A, Y407V mutations; wherein the numbering of amino acid residues is according to Kabat.

11. The isolated heteromultimer according to claim 8, wherein one CH3 domain comprises a Y349C mutation; and the other CH3 domain comprises either a E356C or a S354C mutation; wherein the numbering of amino acid residues is according to Kabat.

12. An isolated heteromultimer comprising a heterodimeric immunoglobulin hinge domain comprising a first immunoglobulin hinge domain polypeptide and a second immunoglobulin hinge domain polypeptide, wherein:
(i) the first immunoglobulin hinge domain polypeptide comprises the following amino acid substitution: A244H; and
(ii) the second immunoglobulin hinge domain polypeptide comprises the following amino acid substitutions: N/E246D, and L247D;
wherein the numbering of amino acid residues is according to Kabat.

13. The isolated heteromultimer according to claim 12, wherein each hinge domain polypeptide further comprises an L248C substitution according to Kabat.

14. An isolated heteromultimer comprising a heterodimeric immunoglobulin hinge domain comprising a first immunoglobulin hinge domain polypeptide and a second immunoglobulin hinge domain polypeptide, wherein:
(i) the first immunoglobulin hinge domain polypeptide comprises the following amino acid substitutions: H237K, T238K, A244K and N/E246K; and
(ii) the second immunoglobulin hinge domain polypeptide comprises the following amino acid substitutions: H237D, T238D, A244D, and N/E246D;
wherein the numbering of amino acid residues is according to Kabat.

15. The isolated heteromultimer according to claim 14, wherein each hinge domain polypeptide further comprises an L248C substitution according to Kabat.

* * * * *

SEQUENCE LISTING

```
<160> NUMBER OF SEQ ID NOS: 77

<210> SEQ ID NO 1
<211> LENGTH: 6
<212> TYPE: PRT
<213> ORGANISM: Artificial Sequence
<220> FEATURE:
<223> OTHER INFORMATION: Linker Sequence

<400> SEQUENCE: 1

Gly Gly Gly Gly Gly Lys
1               5

<210> SEQ ID NO 2
<211> LENGTH: 7
<212> TYPE: PRT
```

-continued

```
<213> ORGANISM: Artificial Sequence
<220> FEATURE:
<223> OTHER INFORMATION: Linker Sequence

<400> SEQUENCE: 2

Gly Gly Gly Gly Gly Lys Arg
1               5

<210> SEQ ID NO 3
<211> LENGTH: 8
<212> TYPE: PRT
<213> ORGANISM: Artificial Sequence
<220> FEATURE:
<223> OTHER INFORMATION: Linker Sequence

<400> SEQUENCE: 3

Gly Gly Gly Lys Gly Gly Gly Gly
1               5

<210> SEQ ID NO 4
<211> LENGTH: 8
<212> TYPE: PRT
<213> ORGANISM: Artificial Sequence
<220> FEATURE:
<223> OTHER INFORMATION: Linker Sequence

<400> SEQUENCE: 4

Gly Gly Gly Asn Gly Ser Gly Gly
1               5

<210> SEQ ID NO 5
<211> LENGTH: 8
<212> TYPE: PRT
<213> ORGANISM: Artificial Sequence
<220> FEATURE:
<223> OTHER INFORMATION: Linker Sequence

<400> SEQUENCE: 5

Gly Gly Gly Cys Gly Gly Gly Gly
1               5

<210> SEQ ID NO 6
<211> LENGTH: 5
<212> TYPE: PRT
<213> ORGANISM: Artificial Sequence
<220> FEATURE:
<223> OTHER INFORMATION: Linker Sequence

<400> SEQUENCE: 6

Gly Pro Asn Gly Gly
1               5

<210> SEQ ID NO 7
<211> LENGTH: 6
<212> TYPE: PRT
<213> ORGANISM: Artificial Sequence
<220> FEATURE:
<223> OTHER INFORMATION: Linker Sequence

<400> SEQUENCE: 7

Gly Gly Glu Gly Gly Gly
1               5

<210> SEQ ID NO 8
<211> LENGTH: 8
<212> TYPE: PRT
<213> ORGANISM: Artificial Sequence
```

```
<220> FEATURE:
<223> OTHER INFORMATION: Linker Sequence

<400> SEQUENCE: 8

Gly Gly Glu Glu Glu Gly Gly Gly
1               5

<210> SEQ ID NO 9
<211> LENGTH: 5
<212> TYPE: PRT
<213> ORGANISM: Artificial Sequence
<220> FEATURE:
<223> OTHER INFORMATION: Linker Sequence

<400> SEQUENCE: 9

Gly Glu Glu Glu Gly
1               5

<210> SEQ ID NO 10
<211> LENGTH: 4
<212> TYPE: PRT
<213> ORGANISM: Artificial Sequence
<220> FEATURE:
<223> OTHER INFORMATION: Linker Sequence

<400> SEQUENCE: 10

Gly Glu Glu Glu
1

<210> SEQ ID NO 11
<211> LENGTH: 6
<212> TYPE: PRT
<213> ORGANISM: Artificial Sequence
<220> FEATURE:
<223> OTHER INFORMATION: Linker Sequence

<400> SEQUENCE: 11

Gly Gly Asp Gly Gly Gly
1               5

<210> SEQ ID NO 12
<211> LENGTH: 7
<212> TYPE: PRT
<213> ORGANISM: Artificial Sequence
<220> FEATURE:
<223> OTHER INFORMATION: Linker Sequence

<400> SEQUENCE: 12

Gly Gly Asp Asp Asp Gly Gly
1               5

<210> SEQ ID NO 13
<211> LENGTH: 5
<212> TYPE: PRT
<213> ORGANISM: Artificial Sequence
<220> FEATURE:
<223> OTHER INFORMATION: Linker Sequence

<400> SEQUENCE: 13

Gly Asp Asp Asp Gly
1               5

<210> SEQ ID NO 14
<211> LENGTH: 4
<212> TYPE: PRT
<213> ORGANISM: Artificial Sequence
<220> FEATURE:
```

```
<223> OTHER INFORMATION: Linker Sequence

<400> SEQUENCE: 14

Gly Asp Asp Asp
1

<210> SEQ ID NO 15
<211> LENGTH: 21
<212> TYPE: PRT
<213> ORGANISM: Artificial Sequence
<220> FEATURE:
<223> OTHER INFORMATION: Linker Sequence

<400> SEQUENCE: 15

Gly Gly Gly Gly Ser Asp Asp Ser Asp Glu Gly Ser Asp Gly Glu Asp
1               5                   10                  15

Gly Gly Gly Gly Ser
            20

<210> SEQ ID NO 16
<211> LENGTH: 5
<212> TYPE: PRT
<213> ORGANISM: Artificial Sequence
<220> FEATURE:
<223> OTHER INFORMATION: Linker Sequence

<400> SEQUENCE: 16

Trp Glu Trp Glu Trp
1               5

<210> SEQ ID NO 17
<211> LENGTH: 5
<212> TYPE: PRT
<213> ORGANISM: Artificial Sequence
<220> FEATURE:
<223> OTHER INFORMATION: Linker Sequence

<400> SEQUENCE: 17

Phe Glu Phe Glu Phe
1               5

<210> SEQ ID NO 18
<211> LENGTH: 6
<212> TYPE: PRT
<213> ORGANISM: Artificial Sequence
<220> FEATURE:
<223> OTHER INFORMATION: Linker Sequence

<400> SEQUENCE: 18

Glu Glu Glu Trp Trp Trp
1               5

<210> SEQ ID NO 19
<211> LENGTH: 6
<212> TYPE: PRT
<213> ORGANISM: Artificial Sequence
<220> FEATURE:
<223> OTHER INFORMATION: Linker Sequence

<400> SEQUENCE: 19

Glu Glu Glu Phe Phe Phe
1               5

<210> SEQ ID NO 20
<211> LENGTH: 7
<212> TYPE: PRT
```

```
<213> ORGANISM: Artificial Sequence
<220> FEATURE:
<223> OTHER INFORMATION: Linker Sequence

<400> SEQUENCE: 20

Trp Trp Glu Glu Glu Trp Trp
1               5

<210> SEQ ID NO 21
<211> LENGTH: 7
<212> TYPE: PRT
<213> ORGANISM: Artificial Sequence
<220> FEATURE:
<223> OTHER INFORMATION: Linker Sequence

<400> SEQUENCE: 21

Phe Phe Glu Glu Glu Phe Phe
1               5

<210> SEQ ID NO 22
<211> LENGTH: 3
<212> TYPE: PRT
<213> ORGANISM: Artificial Sequence
<220> FEATURE:
<223> OTHER INFORMATION: Linker Sequence

<400> SEQUENCE: 22

Gly Gly Gly
1

<210> SEQ ID NO 23
<211> LENGTH: 4
<212> TYPE: PRT
<213> ORGANISM: Artificial Sequence
<220> FEATURE:
<223> OTHER INFORMATION: Linker Sequence

<400> SEQUENCE: 23

Gly Gly Gly Gly
1

<210> SEQ ID NO 24
<211> LENGTH: 5
<212> TYPE: PRT
<213> ORGANISM: Artificial Sequence
<220> FEATURE:
<223> OTHER INFORMATION: Linker Sequence

<400> SEQUENCE: 24

Gly Gly Gly Gly Gly
1               5

<210> SEQ ID NO 25
<211> LENGTH: 6
<212> TYPE: PRT
<213> ORGANISM: Artificial Sequence
<220> FEATURE:
<223> OTHER INFORMATION: Linker Sequence

<400> SEQUENCE: 25

Gly Gly Gly Gly Gly Gly
1               5

<210> SEQ ID NO 26
<211> LENGTH: 7
<212> TYPE: PRT
<213> ORGANISM: Artificial Sequence
```

-continued

```
<220> FEATURE:
<223> OTHER INFORMATION: Linker Sequence

<400> SEQUENCE: 26

Gly Gly Gly Gly Gly Gly Gly
1               5

<210> SEQ ID NO 27
<211> LENGTH: 5
<212> TYPE: PRT
<213> ORGANISM: Artificial Sequence
<220> FEATURE:
<223> OTHER INFORMATION: Linker Sequence

<400> SEQUENCE: 27

Gly Gly Gly Gly Ser
1               5

<210> SEQ ID NO 28
<211> LENGTH: 9
<212> TYPE: PRT
<213> ORGANISM: Artificial Sequence
<220> FEATURE:
<223> OTHER INFORMATION: Linker Sequence

<400> SEQUENCE: 28

Gly Gly Gly Ser Gly Gly Gly Gly Ser
1               5

<210> SEQ ID NO 29
<211> LENGTH: 10
<212> TYPE: PRT
<213> ORGANISM: Artificial Sequence
<220> FEATURE:
<223> OTHER INFORMATION: Linker Sequence

<400> SEQUENCE: 29

Gly Gly Gly Gly Ser Gly Gly Gly Gly Ser
1               5                   10

<210> SEQ ID NO 30
<211> LENGTH: 15
<212> TYPE: PRT
<213> ORGANISM: Artificial Sequence
<220> FEATURE:
<223> OTHER INFORMATION: Linker Sequence

<400> SEQUENCE: 30

Gly Gly Gly Gly Ser Gly Gly Gly Gly Ser Gly Gly Gly Gly Ser
1               5                   10                  15

<210> SEQ ID NO 31
<211> LENGTH: 25
<212> TYPE: PRT
<213> ORGANISM: Artificial Sequence
<220> FEATURE:
<223> OTHER INFORMATION: Linker Sequence

<400> SEQUENCE: 31

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 32
<211> LENGTH: 22
```

-continued

```
<212> TYPE: PRT
<213> ORGANISM: Artificial Sequence
<220> FEATURE:
<223> OTHER INFORMATION: Leader Sequence

<400> SEQUENCE: 32

Met Asp Met Arg Val Pro Ala Gln Leu Leu Gly Leu Leu Leu Trp
1               5                   10                  15

Leu Arg Gly Ala Arg Cys
            20

<210> SEQ ID NO 33
<211> LENGTH: 19
<212> TYPE: PRT
<213> ORGANISM: Artificial Sequence
<220> FEATURE:
<223> OTHER INFORMATION: Leader Sequence

<400> SEQUENCE: 33

Met Ala Trp Ala Leu Leu Leu Leu Thr Leu Leu Thr Gln Gly Thr Gly
1               5                   10                  15

Ser Trp Ala

<210> SEQ ID NO 34
<211> LENGTH: 19
<212> TYPE: PRT
<213> ORGANISM: Artificial Sequence
<220> FEATURE:
<223> OTHER INFORMATION: Leader Sequence

<400> SEQUENCE: 34

Met Thr Cys Ser Pro Leu Leu Leu Thr Leu Leu Ile His Cys Thr Gly
1               5                   10                  15

Ser Trp Ala

<210> SEQ ID NO 35
<211> LENGTH: 20
<212> TYPE: PRT
<213> ORGANISM: Artificial Sequence
<220> FEATURE:
<223> OTHER INFORMATION: Leader Sequence

<400> SEQUENCE: 35

Met Glu Ala Pro Ala Gln Leu Leu Phe Leu Leu Leu Leu Trp Leu Pro
1               5                   10                  15

Asp Thr Thr Gly
            20

<210> SEQ ID NO 36
<211> LENGTH: 19
<212> TYPE: PRT
<213> ORGANISM: Artificial Sequence
<220> FEATURE:
<223> OTHER INFORMATION: Leader Sequence

<400> SEQUENCE: 36

Met Glu Trp Thr Trp Arg Val Leu Phe Leu Val Ala Ala Ala Thr Gly
1               5                   10                  15

Ala His Ser

<210> SEQ ID NO 37
<211> LENGTH: 20
<212> TYPE: PRT
<213> ORGANISM: Artificial Sequence
```

-continued

```
<220> FEATURE:
<223> OTHER INFORMATION: Leader Sequence

<400> SEQUENCE: 37

Met Glu Thr Pro Ala Gln Leu Leu Phe Leu Leu Leu Leu Trp Leu Pro
1               5                   10                  15

Asp Thr Thr Gly
            20

<210> SEQ ID NO 38
<211> LENGTH: 20
<212> TYPE: PRT
<213> ORGANISM: Artificial Sequence
<220> FEATURE:
<223> OTHER INFORMATION: Leader Sequence

<400> SEQUENCE: 38

Met Glu Thr Pro Ala Gln Leu Leu Phe Leu Leu Leu Leu Trp Leu Pro
1               5                   10                  15

Asp Thr Thr Gly
            20

<210> SEQ ID NO 39
<211> LENGTH: 19
<212> TYPE: PRT
<213> ORGANISM: Artificial Sequence
<220> FEATURE:
<223> OTHER INFORMATION: Leader Sequence

<400> SEQUENCE: 39

Met Lys His Leu Trp Phe Phe Leu Leu Leu Val Ala Ala Pro Arg Trp
1               5                   10                  15

Val Leu Ser

<210> SEQ ID NO 40
<211> LENGTH: 19
<212> TYPE: PRT
<213> ORGANISM: Artificial Sequence
<220> FEATURE:
<223> OTHER INFORMATION: Leader Sequence

<400> SEQUENCE: 40

Met Glu Trp Ser Trp Val Phe Leu Phe Phe Leu Ser Val Thr Thr Gly
1               5                   10                  15

Val His Ser

<210> SEQ ID NO 41
<211> LENGTH: 444
<212> TYPE: PRT
<213> ORGANISM: Artificial Sequence
<220> FEATURE:
<223> OTHER INFORMATION: IgG protein sequence

<400> SEQUENCE: 41

Glu Val Lys Leu Gln Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Tyr Ile Ser Asn Gly Gly Gly Ser Thr Tyr Tyr Pro Asp Thr Val
    50                  55                  60
```

```
Lys Gly Arg Phe Thr Ile Ser Arg Asp Asn Ala Lys Asn Thr Leu Tyr
65                  70                  75                  80

Leu Gln Met Ser Arg Leu Lys Ser Glu Asp Thr Ala Met Tyr Tyr Cys
                85                  90                  95

Ala Arg His Gly Gly Tyr Tyr Ala Met Asp Tyr Trp Gly Gln Gly Thr
            100                 105                 110

Thr Val Thr Val Ser Ser Ala Lys Thr Thr Ala Pro Ser Val Tyr Pro
        115                 120                 125

Leu Ala Pro Val Cys Gly Asp Thr Thr Gly Ser Ser Val Thr Leu Gly
        130                 135                 140

Cys Leu Val Lys Gly Tyr Phe Pro Glu Pro Val Thr Leu Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Thr Ser Ser Thr
                180                 185                 190

Trp Pro Ser Gln Ser Ile Thr Cys Asn Val Ala His Pro Ala Ser Ser
                195                 200                 205

Thr Lys Val Asp Lys Lys Ile Glu Pro Arg Gly Pro Thr Ile Lys Pro
        210                 215                 220

Cys Pro Pro Cys Lys Cys Pro Ala Pro Asn Leu Leu Gly Gly Pro Ser
225                 230                 235                 240

Val Phe Ile Phe Pro Pro Lys Ile Lys Asp Val Leu Met Ile Ser Leu
                245                 250                 255

Ser Pro Ile Val Thr Cys Val Val Val Asp Val Ser Glu Asp Asp Pro
                260                 265                 270

Asp Val Gln Ile Ser Trp Phe Val Asn Asn Val Glu Val His Thr Ala
            275                 280                 285

Gln Thr Gln Thr His Arg Glu Asp Tyr Asn Ser Thr Leu Arg Val Val
        290                 295                 300

Ser Ala Leu Pro Ile Gln His Gln Asp Trp Met Ser Gly Lys Glu Phe
305                 310                 315                 320

Lys Cys Lys Val Asn Asn Lys Asp Leu Pro Ala Pro Ile Glu Arg Thr
                325                 330                 335

Ile Ser Lys Pro Lys Gly Ser Val Arg Ala Pro Gln Val Tyr Val Leu
                340                 345                 350

Pro Pro Pro Glu Glu Glu Met Thr Lys Lys Gln Val Thr Leu Thr Cys
                355                 360                 365

Met Val Thr Asp Phe Met Pro Glu Asp Ile Tyr Val Glu Trp Thr Asn
        370                 375                 380

Asn Gly Lys Thr Glu Leu Asn Tyr Lys Asn Thr Glu Pro Val Leu Asp
385                 390                 395                 400

Ser Asp Gly Ser Tyr Phe Met Tyr Ser Lys Leu Arg Val Glu Lys Lys
                405                 410                 415

Asn Trp Val Glu Arg Asn Ser Tyr Ser Cys Ser Val Val His Glu Gly
            420                 425                 430

Leu His Asn His His Thr Thr Lys Ser Phe Ser Arg
        435                 440
```

<210> SEQ ID NO 42
<211> LENGTH: 457
<212> TYPE: PRT
<213> ORGANISM: Artificial Sequence
<220> FEATURE:
<223> OTHER INFORMATION: IgG protein sequence

<400> SEQUENCE: 42

Gln Val Gln Leu Val Gln Ser Gly Ala Glu Val Lys Lys Pro Gly Ala
1               5                   10                  15

Ser Val Lys Val Ser Cys Gln Ala Ser Gly Tyr Arg Phe Ser Asn Phe
                20                  25                  30

Val Ile His Trp Val Arg Gln Ala Pro Gly Gln Arg Phe Glu Trp Met
            35                  40                  45

Gly Trp Ile Asn Pro Tyr Asn Gly Asn Lys Glu Phe Ser Ala Lys Phe
        50                  55                  60

Gln Asp Arg Val Thr Phe Thr Ala Asp Thr Ser Ala Asn Thr Ala Tyr
65                  70                  75                  80

Met Glu Leu Arg Ser Leu Arg Ser Ala Asp Thr Ala Val Tyr Tyr Cys
                85                  90                  95

Ala Arg Val Gly Pro Tyr Ser Trp Asp Asp Ser Pro Gln Asp Asn Tyr
            100                 105                 110

Tyr Met Asp Val Trp Gly Lys Gly Thr Thr Val Ile Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Ala Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu

```
                    405                     410                     415

Tyr Ser Lys Leu Thr Val Asp Lys Ser Arg Trp Gln Gln Gly Asn Val
                420                     425                     430

Phe Ser Cys Ser Val Met His Glu Ala Leu His Asn His Tyr Thr Gln
            435                     440                     445

Lys Ser Leu Ser Leu Ser Pro Gly Lys
    450                     455

<210> SEQ ID NO 43
<211> LENGTH: 443
<212> TYPE: PRT
<213> ORGANISM: Artificial Sequence
<220> FEATURE:
<223> OTHER INFORMATION: IgG protein sequence

<400> SEQUENCE: 43

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Tyr Met Tyr Trp Val Arg Gln Ala Pro Gly Gln Gly Leu Glu Trp Met
            35                  40                  45

Gly Gly Ile Asn Pro Ser Asn Gly Thr Asn Phe Asn Glu Lys Phe Lys
    50                  55                  60

Asn Arg Val Thr Leu Thr Thr Asp Ser Ser Thr Thr Thr Ala Tyr Met
65                  70                  75                  80

Glu Leu Lys Ser Leu Gln Phe Asp Asp Thr Ala Val Tyr Tyr Cys Ala
                85                  90                  95

Arg Arg Asp Tyr Arg Phe Asp Met Gly Phe Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
```

```
305                     310                     315                     320

Lys Val Ser Asn Lys Gly Leu Pro Ser Ser Ile Glu Lys Thr Ile Ser
                325                     330                     335

Lys Ala Lys Gly Gln Pro Arg Glu Pro Gln Val Tyr Thr Leu Pro Pro
                340                     345                     350

Ser Gln Glu Glu Met Thr Lys Asn Gln Val Ser Leu Thr Cys Leu Val
                355                     360                     365

Lys Gly Phe Tyr Pro Ser Asp Ile Ala Val Glu Trp Glu Ser Asn Gly
        370                     375                     380

Gln Pro Glu Asn Asn Tyr Lys Thr Thr Pro Pro Val Leu Asp Ser Asp
385                     390                     395                     400

Gly Ser Phe Phe Leu Tyr Ser Arg Leu Thr Val Asp Lys Ser Arg Trp
                405                     410                     415

Gln Gln Gly Asn Val Phe Ser Cys Ser Val Met His Glu Ala Leu His
                420                     425                     430

Asn His Tyr Thr Gln Lys Ser Leu Ser Leu Ser
        435                     440
```

<210> SEQ ID NO 44
<211> LENGTH: 13
<212> TYPE: PRT
<213> ORGANISM: Artificial Sequence
<220> FEATURE:
<223> OTHER INFORMATION: Charged Zipper Hinge

<400> SEQUENCE: 44

```
Thr His Thr Cys Pro Pro Cys Pro Ala Pro Glu Leu Leu
1               5                   10
```

<210> SEQ ID NO 45
<211> LENGTH: 13
<212> TYPE: PRT
<213> ORGANISM: Artificial Sequence
<220> FEATURE:
<223> OTHER INFORMATION: Charged Zipper Hinge

<400> SEQUENCE: 45

```
Thr His Thr Cys Pro Pro Cys Pro Ala Pro Glu Leu Leu
1               5                   10
```

<210> SEQ ID NO 46
<211> LENGTH: 13
<212> TYPE: PRT
<213> ORGANISM: Artificial Sequence
<220> FEATURE:
<223> OTHER INFORMATION: Charged Zipper Hinge

<400> SEQUENCE: 46

```
Thr His Thr Cys Pro Pro Cys Asp Asp Asp Asp Asp Cys
1               5                   10
```

<210> SEQ ID NO 47
<211> LENGTH: 13
<212> TYPE: PRT
<213> ORGANISM: Artificial Sequence
<220> FEATURE:
<223> OTHER INFORMATION: Charged Zipper Hinge

<400> SEQUENCE: 47

```
Thr His Thr Cys Pro Pro Cys Lys Lys Lys Lys Lys Cys
1               5                   10
```

<210> SEQ ID NO 48
<211> LENGTH: 13
<212> TYPE: PRT
<213> ORGANISM: Artificial Sequence
<220> FEATURE:
<223> OTHER INFORMATION: Charged Zipper Hinge

<400> SEQUENCE: 48

Thr His Thr Cys Pro Pro Cys Pro Asp Asp Asp Asp Cys
1               5                   10

<210> SEQ ID NO 49
<211> LENGTH: 13
<212> TYPE: PRT
<213> ORGANISM: Artificial Sequence
<220> FEATURE:
<223> OTHER INFORMATION: Charged Zipper Hinge

<400> SEQUENCE: 49

Thr His Thr Cys Pro Pro Cys Pro Lys Lys Lys Lys Cys
1               5                   10

<210> SEQ ID NO 50
<211> LENGTH: 13
<212> TYPE: PRT
<213> ORGANISM: Artificial Sequence
<220> FEATURE:
<223> OTHER INFORMATION: Charged Zipper Hinge

<400> SEQUENCE: 50

Thr His Thr Cys Pro Pro Cys Pro Asp Pro Asp Asp Cys
1               5                       10

<210> SEQ ID NO 51
<211> LENGTH: 13
<212> TYPE: PRT
<213> ORGANISM: Artificial Sequence
<220> FEATURE:
<223> OTHER INFORMATION: Charged Zipper Hinge

<400> SEQUENCE: 51

Thr His Thr Cys Pro Pro Cys Pro Lys Pro Lys Lys Cys
1               5                       10

<210> SEQ ID NO 52
<211> LENGTH: 13
<212> TYPE: PRT
<213> ORGANISM: Artificial Sequence
<220> FEATURE:
<223> OTHER INFORMATION: Charged Zipper Hinge

<400> SEQUENCE: 52

Thr His Thr Cys Pro Pro Cys Pro Asp Pro Asp Leu Cys
1               5                       10

<210> SEQ ID NO 53
<211> LENGTH: 13
<212> TYPE: PRT
<213> ORGANISM: Artificial Sequence
<220> FEATURE:
<223> OTHER INFORMATION: Charged Zipper Hinge

<400> SEQUENCE: 53

Thr His Thr Cys Pro Pro Cys Pro Lys Pro Lys Leu Cys
1               5                       10

<210> SEQ ID NO 54

```
<211> LENGTH: 13
<212> TYPE: PRT
<213> ORGANISM: Artificial Sequence
<220> FEATURE:
<223> OTHER INFORMATION: Charged Zipper Hinge

<400> SEQUENCE: 54

Thr His Thr Cys Pro Pro Cys Pro Asp Pro Asp Leu Leu
1               5                   10

<210> SEQ ID NO 55
<211> LENGTH: 13
<212> TYPE: PRT
<213> ORGANISM: Artificial Sequence
<220> FEATURE:
<223> OTHER INFORMATION: Charged Zipper Hinge

<400> SEQUENCE: 55

Thr His Thr Cys Pro Pro Cys Pro Lys Pro Lys Leu Leu
1               5                   10

<210> SEQ ID NO 56
<211> LENGTH: 13
<212> TYPE: PRT
<213> ORGANISM: Artificial Sequence
<220> FEATURE:
<223> OTHER INFORMATION: Charged Zipper Hinge

<400> SEQUENCE: 56

Thr His Thr Cys Pro Pro Cys Pro Asp Pro Glu Leu Leu
1               5                   10

<210> SEQ ID NO 57
<211> LENGTH: 13
<212> TYPE: PRT
<213> ORGANISM: Artificial Sequence
<220> FEATURE:
<223> OTHER INFORMATION: Charged Zipper Hinge

<400> SEQUENCE: 57

Thr His Thr Cys Pro Pro Cys Pro Lys Pro Leu Leu Leu
1               5                   10

<210> SEQ ID NO 58
<211> LENGTH: 13
<212> TYPE: PRT
<213> ORGANISM: Artificial Sequence
<220> FEATURE:
<223> OTHER INFORMATION: Charged Zipper Hinge

<400> SEQUENCE: 58

Thr His Asp Cys Pro Pro Cys Pro Asp Pro Asp Leu Leu
1               5                   10

<210> SEQ ID NO 59
<211> LENGTH: 13
<212> TYPE: PRT
<213> ORGANISM: Artificial Sequence
<220> FEATURE:
<223> OTHER INFORMATION: Charged Zipper Hinge

<400> SEQUENCE: 59

Thr His Lys Cys Pro Pro Cys Pro Lys Pro Lys Leu Leu
1               5                   10

<210> SEQ ID NO 60
<211> LENGTH: 13
```

```
<212> TYPE: PRT
<213> ORGANISM: Artificial Sequence
<220> FEATURE:
<223> OTHER INFORMATION: Charged Zipper Hinge

<400> SEQUENCE: 60

Thr Asp Thr Cys Pro Pro Cys Pro Asp Pro Asp Leu Leu
1               5                   10

<210> SEQ ID NO 61
<211> LENGTH: 13
<212> TYPE: PRT
<213> ORGANISM: Artificial Sequence
<220> FEATURE:
<223> OTHER INFORMATION: Charged Zipper Hinge

<400> SEQUENCE: 61

Thr Lys Thr Cys Pro Pro Cys Pro Lys Pro Lys Leu Leu
1               5                   10

<210> SEQ ID NO 62
<211> LENGTH: 13
<212> TYPE: PRT
<213> ORGANISM: Artificial Sequence
<220> FEATURE:
<223> OTHER INFORMATION: Charged Zipper Hinge

<400> SEQUENCE: 62

Thr Asp Asp Cys Pro Pro Cys Pro Asp Pro Asp Leu Leu
1               5                   10

<210> SEQ ID NO 63
<211> LENGTH: 13
<212> TYPE: PRT
<213> ORGANISM: Artificial Sequence
<220> FEATURE:
<223> OTHER INFORMATION: Charged Zipper Hinge

<400> SEQUENCE: 63

Thr Lys Lys Cys Pro Pro Cys Pro Lys Pro Lys Leu Leu
1               5                   10

<210> SEQ ID NO 64
<211> LENGTH: 13
<212> TYPE: PRT
<213> ORGANISM: Artificial Sequence
<220> FEATURE:
<223> OTHER INFORMATION: Charged Zipper Hinge

<400> SEQUENCE: 64

Thr His Thr Cys Pro Pro Cys Pro Ala Pro Asp Asp Leu
1               5                   10

<210> SEQ ID NO 65
<211> LENGTH: 13
<212> TYPE: PRT
<213> ORGANISM: Artificial Sequence
<220> FEATURE:
<223> OTHER INFORMATION: Charged Zipper Hinge

<400> SEQUENCE: 65

Thr His Thr Cys Pro Pro Cys Pro Lys Pro Glu Leu Leu
1               5                   10

<210> SEQ ID NO 66
<211> LENGTH: 13
<212> TYPE: PRT
```

```
<213> ORGANISM: Artificial Sequence
<220> FEATURE:
<223> OTHER INFORMATION: Charged Zipper Hinge

<400> SEQUENCE: 66

Thr His Thr Cys Pro Pro Cys Pro Ala Pro Asp Asp Leu
1               5               10

<210> SEQ ID NO 67
<211> LENGTH: 13
<212> TYPE: PRT
<213> ORGANISM: Artificial Sequence
<220> FEATURE:
<223> OTHER INFORMATION: Charged Zipper Hinge

<400> SEQUENCE: 67

Thr His Thr Cys Pro Pro Cys Pro His Pro Glu Leu Leu
1               5               10

<210> SEQ ID NO 68
<211> LENGTH: 13
<212> TYPE: PRT
<213> ORGANISM: Artificial Sequence
<220> FEATURE:
<223> OTHER INFORMATION: Charged Zipper Hinge

<400> SEQUENCE: 68

Ile Lys Pro Cys Pro Pro Cys Pro Asp Pro Asp Leu Leu
1               5               10

<210> SEQ ID NO 69
<211> LENGTH: 13
<212> TYPE: PRT
<213> ORGANISM: Artificial Sequence
<220> FEATURE:
<223> OTHER INFORMATION: Charged Zipper Hinge

<400> SEQUENCE: 69

Ile Lys Pro Cys Pro Pro Cys Pro Lys Pro Lys Leu Leu
1               5               10

<210> SEQ ID NO 70
<211> LENGTH: 10
<212> TYPE: PRT
<213> ORGANISM: Artificial Sequence
<220> FEATURE:
<223> OTHER INFORMATION: Charged Zipper Hinge

<400> SEQUENCE: 70

Cys Pro Pro Cys Pro Asp Pro Asp Leu Leu
1               5               10

<210> SEQ ID NO 71
<211> LENGTH: 10
<212> TYPE: PRT
<213> ORGANISM: Artificial Sequence
<220> FEATURE:
<223> OTHER INFORMATION: Charged Zipper Hinge

<400> SEQUENCE: 71

Cys Pro Pro Cys Pro Lys Pro Lys Leu Leu
1               5               10

<210> SEQ ID NO 72
<211> LENGTH: 28
<212> TYPE: PRT
<213> ORGANISM: Artificial Sequence
```

<220> FEATURE:
<223> OTHER INFORMATION: Charged Zipper Hinge

<400> SEQUENCE: 72

Lys Lys Ile Glu Pro Arg Gly Pro Thr Ile Lys Pro Cys Pro Pro Cys
1               5                   10                  15

Lys Cys Pro Ala Pro Asn Leu Leu Gly Gly Pro Ser
            20                  25

<210> SEQ ID NO 73
<211> LENGTH: 27
<212> TYPE: PRT
<213> ORGANISM: Artificial Sequence
<220> FEATURE:
<223> OTHER INFORMATION: Charged Zipper Hinge

<400> SEQUENCE: 73

Lys Lys Ala Glu Pro Lys Ser Cys Asp Lys Thr His Thr Cys Pro Pro
1               5                   10                  15

Cys Pro Ala Pro Glu Leu Leu Gly Gly Pro Ser
            20                  25

<210> SEQ ID NO 74
<211> LENGTH: 24
<212> TYPE: PRT
<213> ORGANISM: Artificial Sequence
<220> FEATURE:
<223> OTHER INFORMATION: Charged Zipper Hinge

<400> SEQUENCE: 74

Lys Arg Val Glu Ser Lys Tyr Gly Pro Pro Cys Pro Pro Cys Pro Ala
1               5                   10                  15

Pro Glu Phe Leu Gly Gly Pro Ser
            20

<210> SEQ ID NO 75
<211> LENGTH: 28
<212> TYPE: PRT
<213> ORGANISM: Artificial Sequence
<220> FEATURE:
<223> OTHER INFORMATION: Charged Zipper Hinge

<400> SEQUENCE: 75

Lys Lys Ile Glu Pro Arg Gly Pro Thr Ile Lys Pro Cys Pro Pro Cys
1               5                   10                  15

Lys Cys Pro Ala Pro Asn Leu Leu Gly Gly Pro Ser
            20                  25

<210> SEQ ID NO 76
<211> LENGTH: 27
<212> TYPE: PRT
<213> ORGANISM: Artificial Sequence
<220> FEATURE:
<223> OTHER INFORMATION: Charged Zipper Hinge

<400> SEQUENCE: 76

Lys Lys Ala Glu Pro Lys Ser Cys Asp Lys Thr His Thr Cys Pro Pro
1               5                   10                  15

Cys Pro Ala Pro Glu Leu Leu Gly Gly Pro Ser
            20                  25

<210> SEQ ID NO 77
<211> LENGTH: 28
<212> TYPE: PRT

-continued

```
<213> ORGANISM: Artificial Sequence
<220> FEATURE:
<223> OTHER INFORMATION: Charged Zipper Hinge

<400> SEQUENCE: 77

Lys Lys Ile Glu Pro Arg Gly Pro Thr Ile Lys Pro Cys Pro Pro Cys
1               5                   10                  15

Lys Cys Pro Ala Pro Asn Leu Leu Gly Gly Pro Ser
                20                  25
```